US009006252B2

(12) United States Patent
Hsieh et al.

(10) Patent No.: US 9,006,252 B2
(45) Date of Patent: Apr. 14, 2015

(54) FUSED MULTICYCLIC COMPOUNDS AS PROTEIN KINASE INHIBITORS

(75) Inventors: Hsing-Pang Hsieh, Miaoli County (TW); Selvaraj Mohane Coumar, Pondicherry (IN); Yu-Sheng Chao, Monmouth Junction, NJ (US)

(73) Assignee: National Health Research Institutes, Miaoli County (TW)

(*) Notice: Subject to any disclaimer, the term of this patent is extended or adjusted under 35 U.S.C. 154(b) by 914 days.

(21) Appl. No.: 12/564,218

(22) Filed: Sep. 22, 2009

(65) Prior Publication Data

US 2010/0081675 A1    Apr. 1, 2010

Related U.S. Application Data

(60) Provisional application No. 61/100,490, filed on Sep. 26, 2008.

(51) Int. Cl.

| | | |
|---|---|---|
| C07D 239/94 | (2006.01) |
| C07D 413/12 | (2006.01) |
| C07D 403/12 | (2006.01) |
| C07D 411/12 | (2006.01) |
| A61K 31/4365 | (2006.01) |
| A61K 31/517 | (2006.01) |
| A61K 31/519 | (2006.01) |
| C07D 401/12 | (2006.01) |
| C07D 417/12 | (2006.01) |
| C07D 417/14 | (2006.01) |
| C12N 9/99 | (2006.01) |
| C07D 498/04 | (2006.01) |
| C07D 215/20 | (2006.01) |
| C07D 215/26 | (2006.01) |
| C07D 471/04 | (2006.01) |
| C07D 495/04 | (2006.01) |
| C07D 491/04 | (2006.01) |
| C07D 495/14 | (2006.01) |
| C07D 513/04 | (2006.01) |
| C07D 487/04 | (2006.01) |
| C07D 473/34 | (2006.01) |

(52) U.S. Cl.
CPC ............ A61K 31/4365 (2013.01); A61K 31/517 (2013.01); A61K 31/519 (2013.01); C07D 239/94 (2013.01); C07D 401/12 (2013.01); C07D 403/12 (2013.01); C07D 417/12 (2013.01); C07D 417/14 (2013.01); C07D 471/04 (2013.01); C07D 487/04 (2013.01); C07D 491/04 (2013.01); C07D 495/04 (2013.01); C07D 495/14 (2013.01); C07D 498/04 (2013.01); C07D 513/04 (2013.01); C12N 9/99 (2013.01)

(58) Field of Classification Search
CPC ... A61K 31/517; C07D 401/12; C07D 239/94
USPC ............... 544/283, 284, 293, 287; 514/266.2, 514/266.21, 266.23, 266.4, 266.3
See application file for complete search history.

(56) References Cited

U.S. PATENT DOCUMENTS

| | | | | |
|---|---|---|---|---|
| 5,326,766 | A | * | 7/1994 | Dreikorn et al. ............ 514/266.2 |
| 5,411,963 | A | * | 5/1995 | Dreikorn et al. ............ 514/266.3 |
| 6,127,541 | A | * | 10/2000 | Onoda et al. ................... 544/251 |
| 2002/0193389 | A1 | * | 12/2002 | Pamukcu et al. .............. 514/267 |
| 2004/0053908 | A1 | | 3/2004 | Funahashi et al. |
| 2004/0242883 | A1 | | 12/2004 | Boschelli et al. |
| 2004/0259888 | A1 | | 12/2004 | Bischoff et al. |
| 2005/0004142 | A1 | | 1/2005 | Adams et al. |
| 2005/0153989 | A1 | | 7/2005 | Grotzfeld et al. |
| 2005/0165029 | A1 | | 7/2005 | Patel et al. |
| 2005/0227992 | A1 | | 10/2005 | Hurley et al. |
| 2006/0035908 | A1 | | 2/2006 | Lew et al. |
| 2006/0040961 | A1 | | 2/2006 | Buchanan et al. |
| 2007/0027166 | A1 | | 2/2007 | Oslob et al. |

FOREIGN PATENT DOCUMENTS

| | | | |
|---|---|---|---|
| DE | 10141212 | | 3/2003 |
| JP | 11-130750 | * | 5/1999 |
| WO | WO 02/32872 | | 4/2002 |

(Continued)

OTHER PUBLICATIONS

JP 11-130750 English abstract, 1 page, May 1999.*
Wu et al. (Huaxue Wuli Xuebao, 2005, 18(6), pp. 836-940).*
Wu et al., Huaxue Wuli Xuebao, 2005, 18(6), pp. 936-940.*
Bauser et al. "Discovery and optimization of 2-aryl oxazolo-pyrimidines as adenosine kinase inhibitors using liquid phase parallel synthesis." Bioorganic & Medicinal Chemistry Letters 14 (2004), pp. 1997-2000.

(Continued)

Primary Examiner — Susanna Moore
(74) Attorney, Agent, or Firm — Cesari and McKenna, LLP

(57) ABSTRACT

Fused multicyclic compounds of formula (I):

$$X-Y-\underset{n}{\overset{R' \; R''}{\mid}}-A-B-\underset{Z}{\overset{\parallel}{C}}-D \quad (I)$$

wherein R', R", X, Y, Z, A, B, C, D, and n are defined herein. Also disclosed are a method for inhibiting protein kinase (e.g., Aurora kinase) activity and a method for treating a protein kinase mediated disorder (e.g., cancer) with these compounds.

23 Claims, No Drawings

(56) References Cited

FOREIGN PATENT DOCUMENTS

| WO | WO03/018589 | 3/2003 |
|---|---|---|
| WO | WO 03/022852 | 3/2003 |
| WO | WO2005/067546 | 7/2005 |
| WO | WO2005/092896 | 10/2005 |
| WO | WO2006/004658 | 1/2006 |
| WO | WO2006/036266 | 4/2006 |
| WO | WO 2006/080043 | 8/2006 |
| WO | WO2007/013964 | 2/2007 |
| WO | WO2007/053343 | 5/2007 |

OTHER PUBLICATIONS

International Search Report and Written Opinion issued in International Application No. PCT/US2009/057768, dated May 11, 2010, 15 pages.

Oslob, J.D., et al. "Discovery of a potent and selective Aurora kinase inhibitor" *Bioorganic & Medicinal Chemistry Letters*, Pergamon, Elsevier Science, GB, vol. 18, No. 17 (Sep. 1, 2008) pp. 4880-4884.

Monge et al., "New 4-Amino-7,8-dimethoxy-5H-pyrimido[5,4-b]indole Derivatives: Synthesis and Studies as Inhibitors of Phosphodiesterases," Arch. Pharma 326:879-885 (1993).

* cited by examiner

FUSED MULTICYCLIC COMPOUNDS AS PROTEIN KINASE INHIBITORS

CROSS-REFERENCE TO RELATED APPLICATION

This application claims the benefit of the priority pursuant to 35 U.S.C. §119(e) of U.S. Provisional Patent Application No. 61/100,490, filed Sep. 26, 2008. The content of the prior application is incorporated herein by its entirety.

BACKGROUND

Protein kinases play important roles in cellular signal pathways that regulate various cell functions such as differentiation, proliferation, migration, and apoptosis. Deregulation of protein kinases is implicated in a number of diseases including cancer. Thus protein kinases are attractive therapeutic targets in cancer treatment.

Aurora kinases, belonging to the serine/threonine subclass of kinases, are involved in the regulation of mitosis. Three isoforms A, B and C are known. Aurora A is involved in centrosome maturation and separation, bi-polar spindle assembly and mitotic entry; Aurora B and C are essential for accurate chromosome segregation and cytokinesis. The deregulated Aurora kinase activity has been linked to genetic instability, defects in centrosome function, spindle assembly, chromosome alignment, and cytokinesis, all of which can lead to tumorigenesis. For example, both Aurora A and B levels are up-regulated in various cancers, including breast and colorectal cancers. Thus, it is of great interest to develop Aurora kinase inhibitors as anti-cancer drugs.

SUMMARY

This invention is based on the discovery that certain fused multicyclic compounds can be used to inhibit activity of protein kinase (e.g., Aurora kinase), which allows these compounds to be applied in treating protein kinase mediated disorders such as cancer.

In one aspect, this invention relates to a fused multicyclic compound of formula (I):

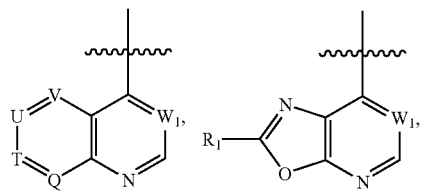

(I)

In formula (I), X is selected from the group consisting of

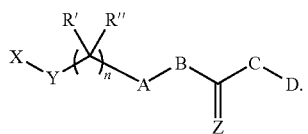

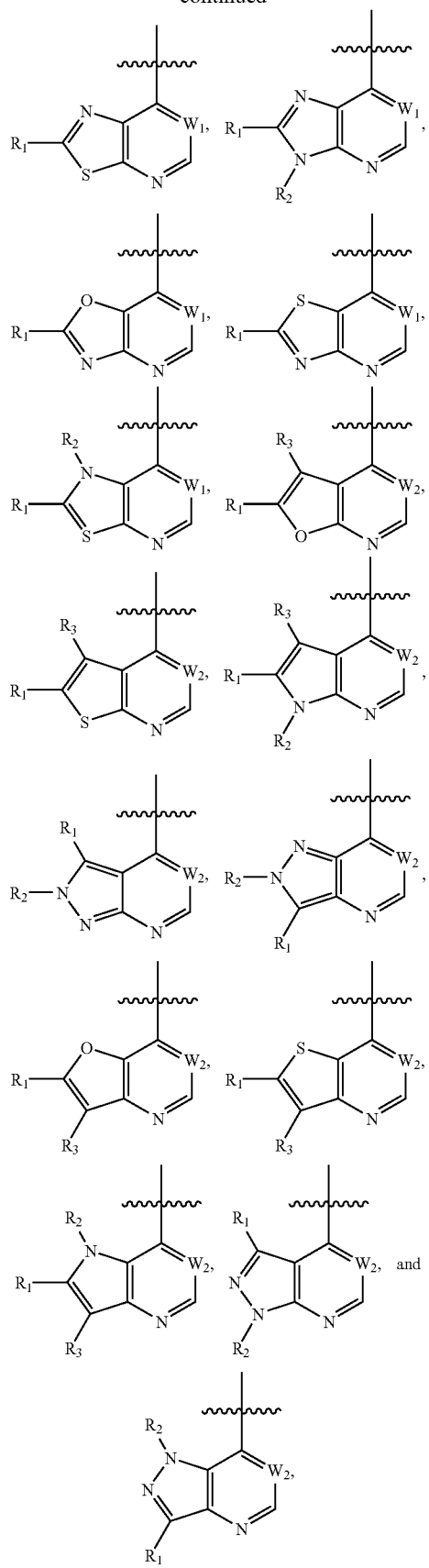

in which each of $R_1$, $R_2$, and $R_3$, independently, is H, alkyl, alkenyl, alkynyl, aryl, heteroaryl, cycloalkyl, cycloalkenyl, heterocycloalkyl, heterocycloalkenyl, halo, cyano, nitro, $OR_a$, $OC(O)R_a$, $C(O)R_a$, $C(O)OR_a$, $C(O)NR_aR_b$, $NR_aR_b$, $NHC(O)R_a$, $NHC(O)NR_aR_b$, $NHC(S)R_a$, $NHC(O)OR_a$, $SO_3R_a$, or $SO_2NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl; or $R_1$ and $R_3$, together with the carbon atoms to which they are bonded, are cycloalkenyl, heterocycloalkenyl, aryl, or heteroaryl; each of Q, T, U, and V, independently, is N or $CR_3$; $W_1$ is N or $CR_4$, in which $R_4$ is H, cyano, halo, or $CONH_2$; and $W_2$ is $CR_5$ in which $R_5$ is H, cyano, halo, or $CONH_2$; each of Y and Z, independently, is O, S, or $NR_c$, in which $R_1$ is deleted, H, alkyl, alkenyl, alkynyl, aryl, heteroaryl, cycloalkyl, cycloalkenyl, heterocycloalkyl, heterocycloalkenyl, cyano, or $NO_2$; each of R' and R", independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl; A is arylene or heteroarylene; B is O, S or $NR_d$, in which $R_d$ is H, alkyl, alkenyl, or alkynyl; C is O, S, alkylene, or $NR_e$, in which $R_e$ is H, alkyl, alkenyl, or alkynyl; or B and C, together with the carbon atom to which they are bonded, are heterocycloalkyl or heterocycloalkenyl; D is H, alkyl, alkenyl, alkynyl, aryl, heteroaryl, cycloalkyl, cycloalkenyl, heterocycloalkyl, or heterocycloalkenyl; or C and D together are heterocycloalkyl, heterocycloalkenyl, aryl, or heteroaryl; or C, D, and Z together with the carbon atom to which they are bonded are heteroaryl; and n is 0, 1, 2, 3, or 4.

One subset of the above-described compounds includes those in which Z is O and each of B and C is NH. In these compounds, X can be

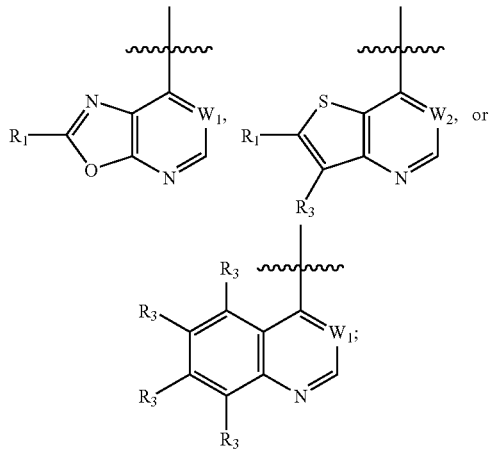

$W_1$ can be N or $CR_4$ in which $R_4$ is H, cyano, or Cl; $W_2$ can be $CR_5$ in which $R_5$ is H, cyano, or Cl; $R_1$ can be H, alkyl, alkynyl, aryl (e.g., phenyl optionally substituted with hydroxy or alkoxy), or heteroaryl; each of the $R_3$ groups, independently, can be H, alkyl, alkynyl, halo, cyano, nitro, $OR_a$, or $NR_aR_b$, in which each of $R_a$ and $R_b$, independently, is H, alkyl, alkenyl, alkynyl, cycloalkyl, aryl, or heteroaryl; each of R' and R" can be H; Y can be NH; A can be phenyl or thiazolyl; D can be alkyl, aryl, heteroaryl, or cycloalkyl; or n can be 2.

Another subset of the compounds includes those in which X is

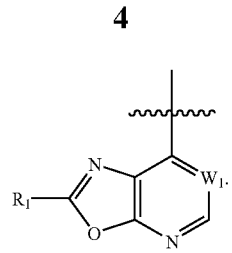

In these compounds, $R_1$ can be H, alkyl, alkynyl, aryl (e.g., phenyl optionally substituted with hydroxy or alkoxy), or heteroaryl; $W_1$ can be N; Y can be NH; Z can be O; A can be phenyl or thiazolyl; each of B and C can be NH; D can be alkyl, aryl, heteroaryl, or cycloalkyl; or n can be 2.

Yet another subset of the compounds includes those in which X is

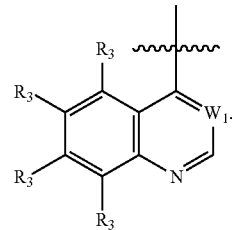

In these compounds, each of the $R_3$ groups, independently, can be H, alkyl, alkynyl, halo, cyano, nitro, $OR_a$, or $NR_cR_d$, in which each of $R_c$ and $R_d$, independently, is H, alkyl (eg., alkyl optionally substituted with alkylamino), alkenyl, alkynyl, cycloalkyl, aryl (e.g., phenyl optionally substituted with hydroxy or alkoxy), or heteroaryl; $W_1$ can be N; Y can be NH; Z can be O; A can be phenyl or thiazolyl; each of B and C can be NH; D can be alkyl, aryl, heteroaryl, or cycloalkyl; or n can be 2.

Still another subset of the compounds includes those in which $W_2$ is $CR_5$, in which $R_5$ is H, cyano, or Cl. In these compounds, Y can be NH; Z can be O; A can be phenyl or thiazolyl; each of B and C can be NH; D can be alkyl, aryl, heteroaryl, or cycloalkyl; or n can be 2.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_{10}$). Examples of alkylene include, but are not limited to, methylene and ethylene. The term "alkenyl" refers to a straight or branched monovalent or bivalent hydrocarbon containing 2-20 carbon atoms (e.g., $C_2$-$C_{10}$) and one or more double bonds. Examples of alkenyl include, but are not limited to, ethenyl, propenyl, propenylene, allyl, and 1,4-butadienyl. The term "alkynyl" refers to a straight or branched monovalent or bivalent hydrocarbon containing 2-20 carbon atoms (e.g., $C_2$-$C_{10}$) and one or more triple bonds. Examples of alkynyl include, but are not limited to, ethynyl, ethynylene, 1-propynyl, 1- and 2-butynyl, and 1-methyl-2-butyryl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent or bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, 1,4-cyclohexylene, cycloheptyl, and cyclooctyl. The term "cycloalkenyl" refers to a monovalent or bivalent nonaromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a monovalent or bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, alkylamino, aryl, heteroaryl, alkylene, arylene, and heteroarylene mentioned above include both substituted and unsubstituted moieties. Possible substituents on alkylamino, cycloalkyl, heterocycloalkyl, cycloalkenyl, heterocycloalkenyl, aryl, arylene, heteroaryl, and heteroarylene include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O═), thioxo (S═), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, alkynyl, or alkylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The fused multicyclic compounds described above include the compounds themselves, as well as their salts, their solvates, and their prodrugs, if applicable. A salt, for example, can be formed between an anion and a positively charged group (e.g., amino) on a fused multicyclic compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a fused multicyclic compound. Suitable cations include sodium ion, potassium ion, magnesium ion, calcium ion, and an ammonium cation such as tetramethylammonium ion. The fused multicyclic compounds also include those salts containing quaternary nitrogen atoms. Examples of prodrugs include esters and other pharmaceutically acceptable derivatives, which, upon administration to a subject, are capable of providing active fused multicyclic compounds.

In another aspect, this invention relates to this invention relates to a method of inhibiting protein kinase (e.g., Aurora kinase) activity by contacting a cell expressing the protein kinase with an effective amount of one or more of the fused multicyclic compounds described above. The cell can be a tumor cell or a cell that over-expresses the protein kinase (e.g., Aurora kinase).

In still another aspect, this invention relates to a method of treating a protein kinase (e.g., Aurora kinase) mediated disorder such as cancer by administering to a subject in need thereof an effective amount of one or more of the fused multicyclic compounds described above.

Also within the scope of this invention is a pharmaceutical composition containing one or more of the above-described fused multicyclic compounds for use in treating a protein kinase mediated disorder (e.g., cancer), as well as this therapeutic use and use of the compounds for the manufacture of a medicament for treating the disorder.

The details of one or more embodiments of the invention are set forth in the description below. Other features, objects, and advantages of the invention will be apparent from the description and from the claims.

DETAILED DESCRIPTION

Shown below are exemplary compounds of this invention:

Compound 1

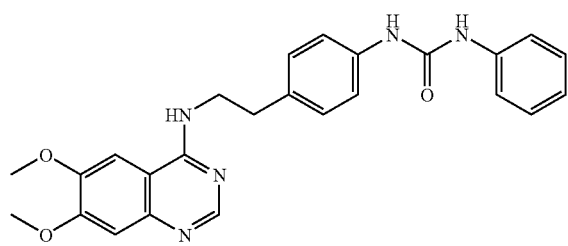

Compound 2

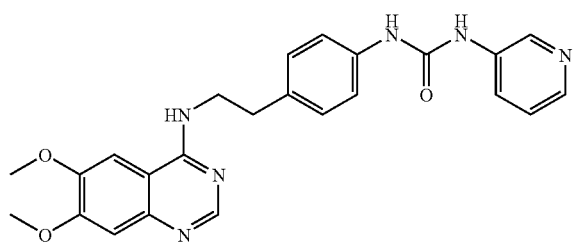

-continued
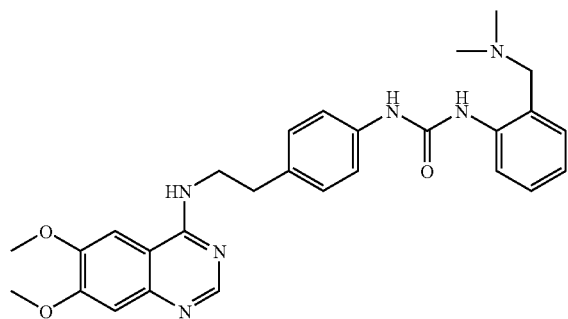
Compound 3
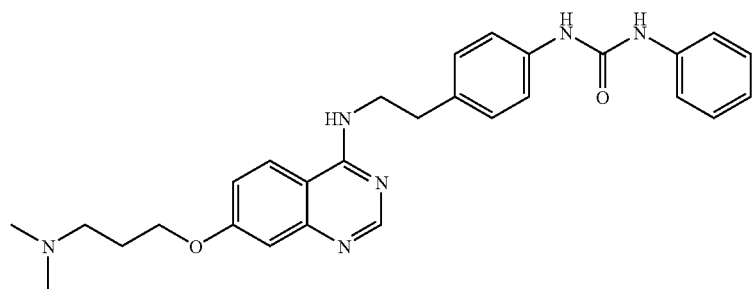
Compound 4
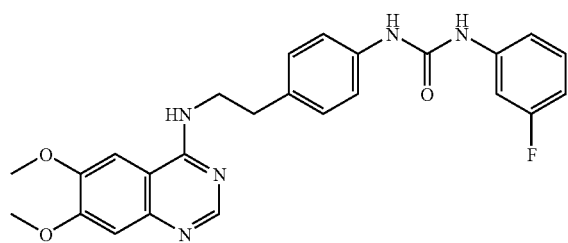
Compound 5
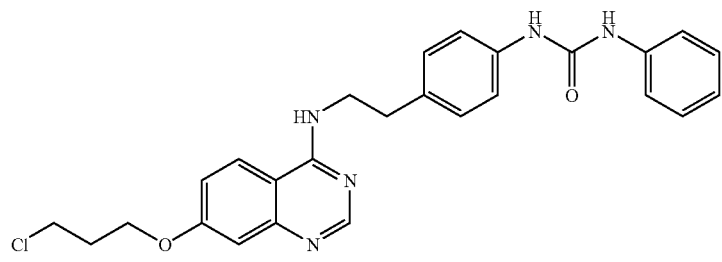
Compound 6
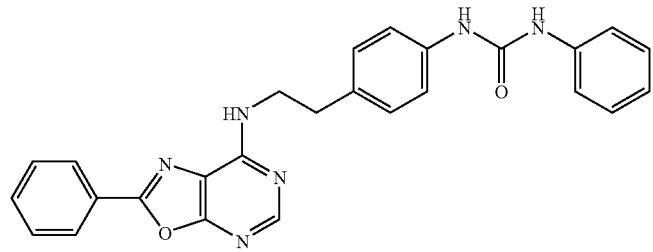
Compound 7
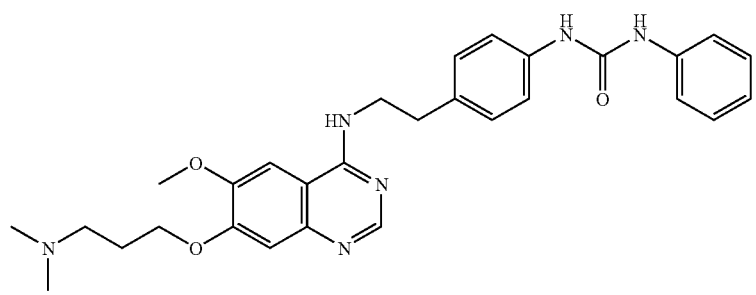
Compound 8

Compound 9
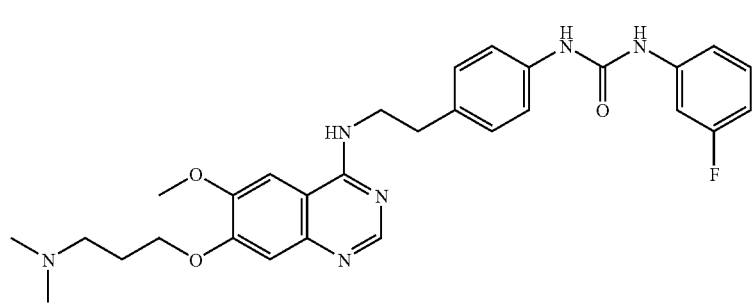
Compound 10
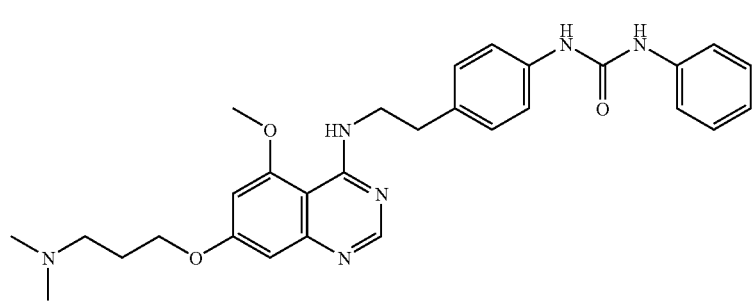
Compound 11
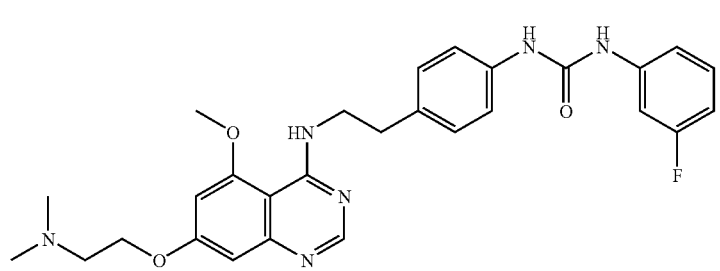
Compound 12
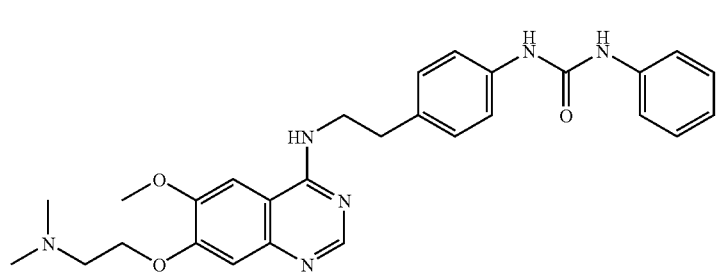
Compound 13
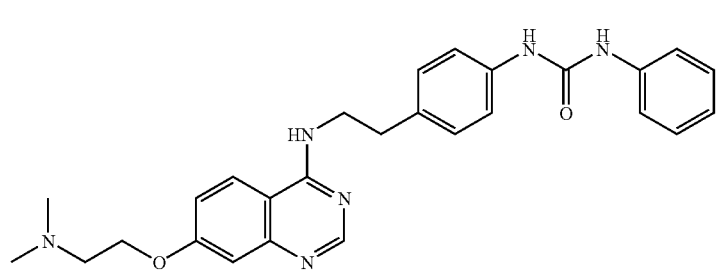
Compound 14
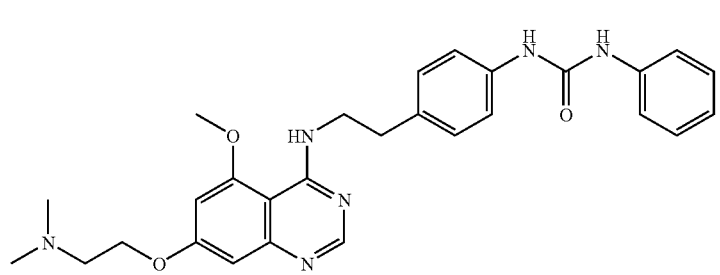

-continued
Compound 15
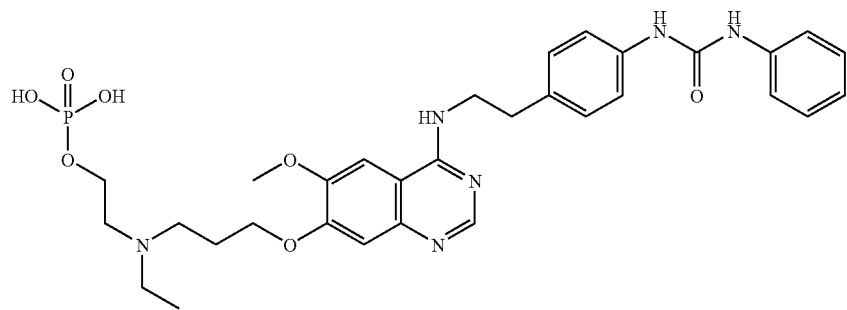
Compound 16
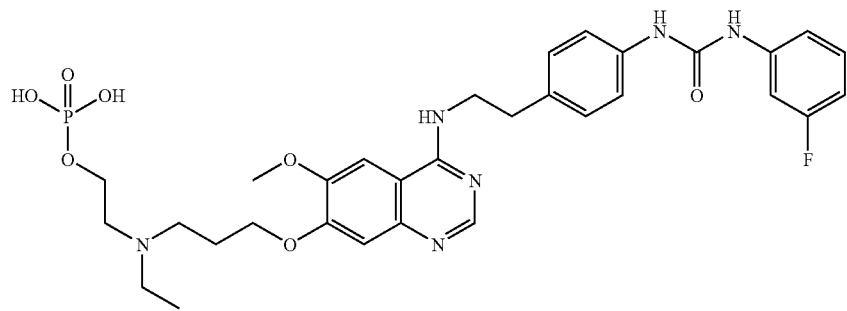
Compound 17
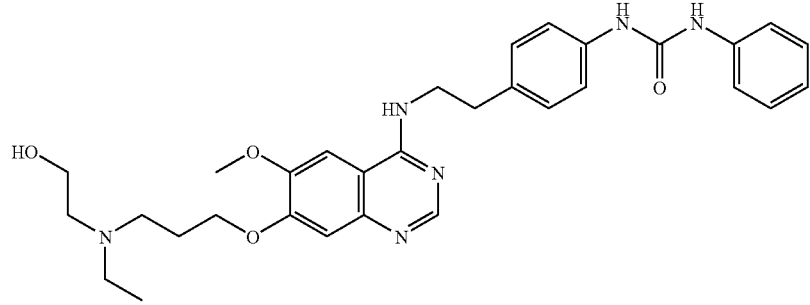
Compound 18
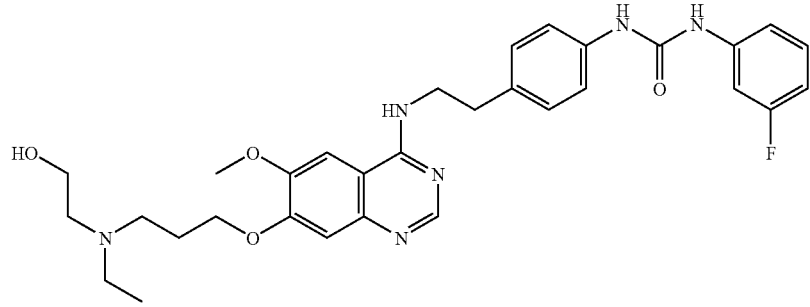
Compound 19
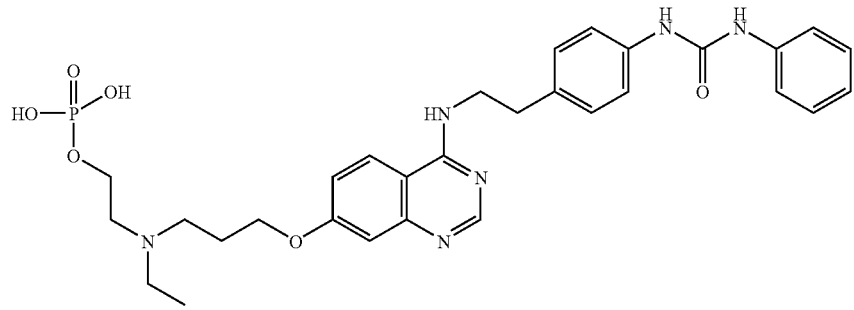

-continued
Compound 20
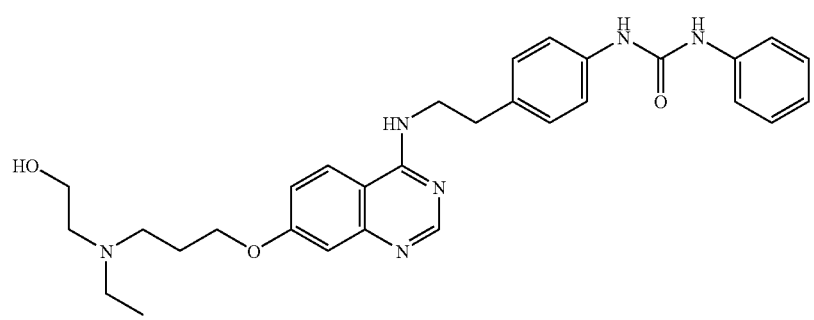
Compound 21
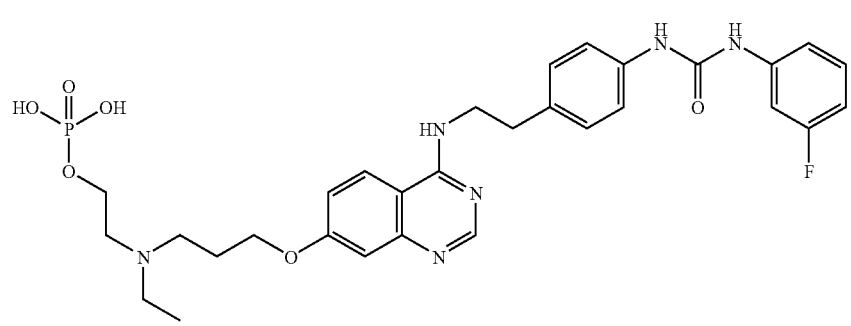
Compound 22
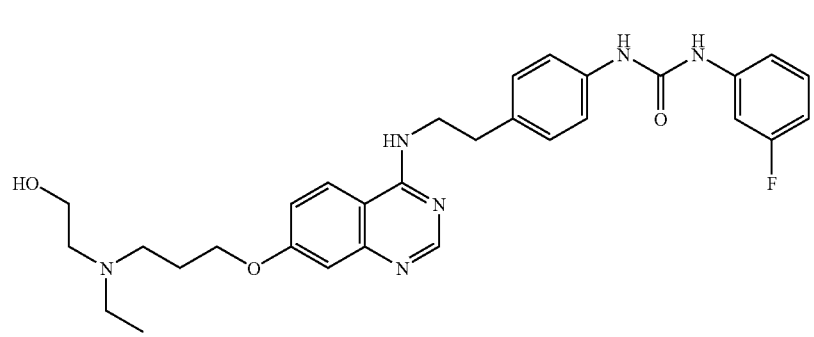
Compound 23
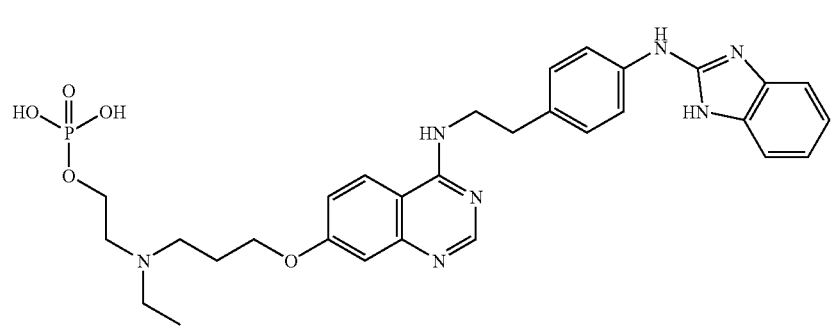
Compound 24
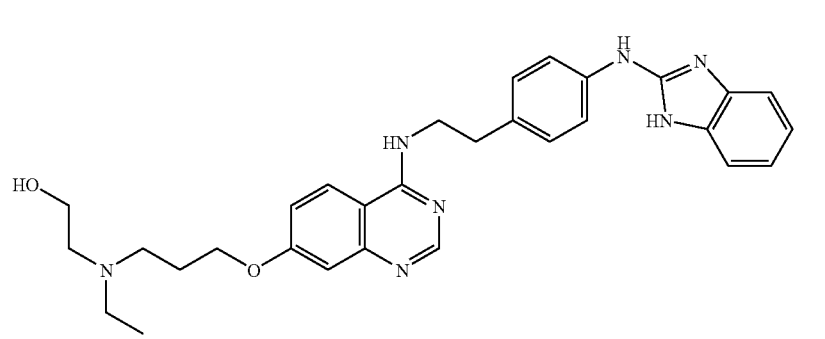

-continued
Compound 25
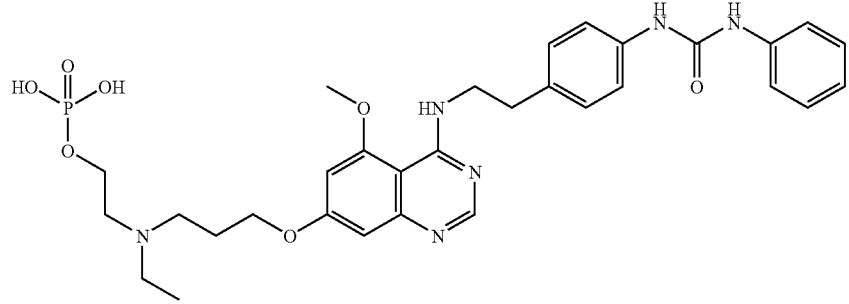
Compound 26
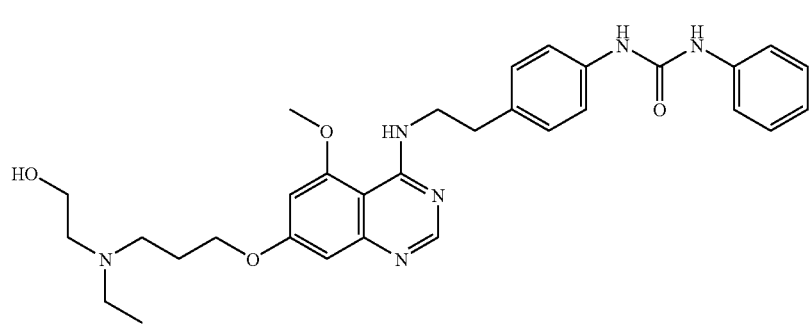
Compound 27
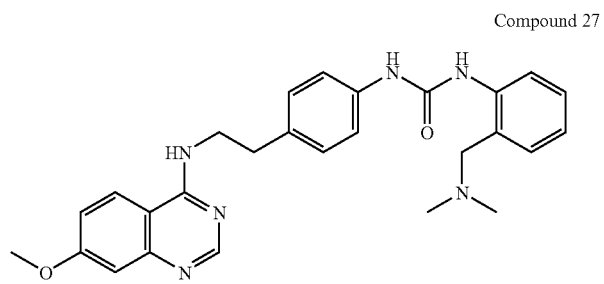
Compound 28
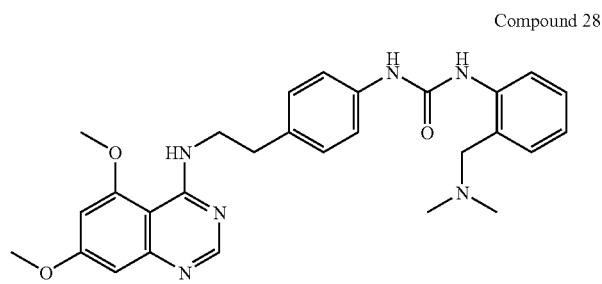
Compound 29
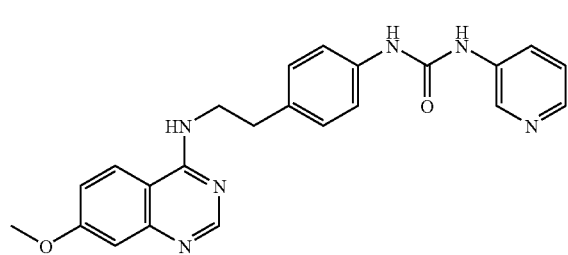
Compound 30
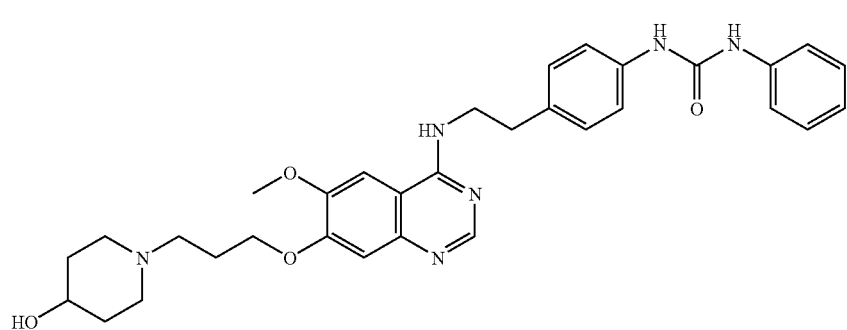

-continued
Compound 31
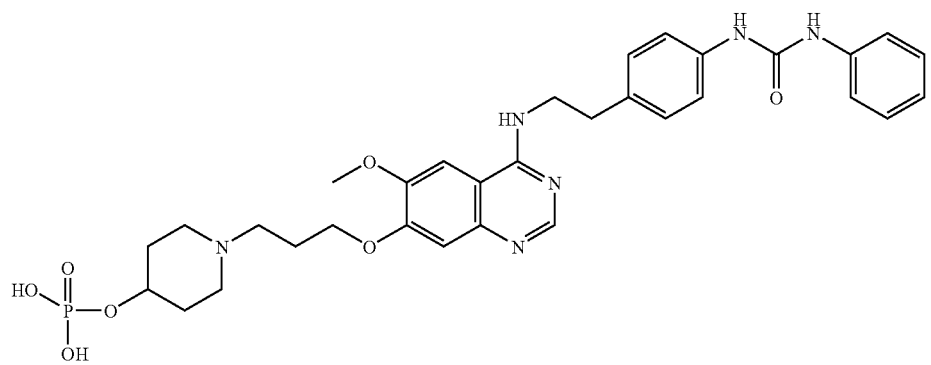
Compound 32
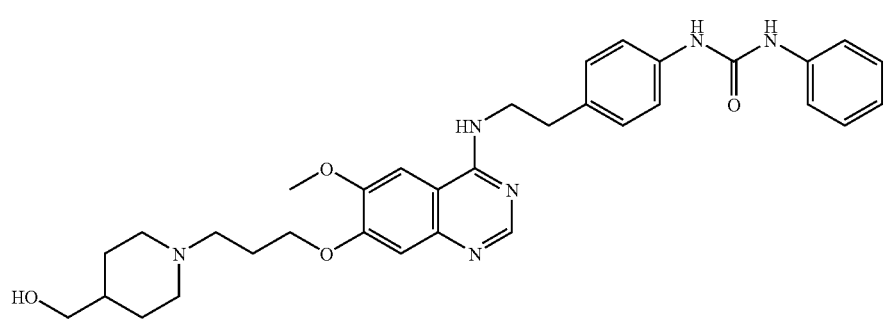
Compound 33
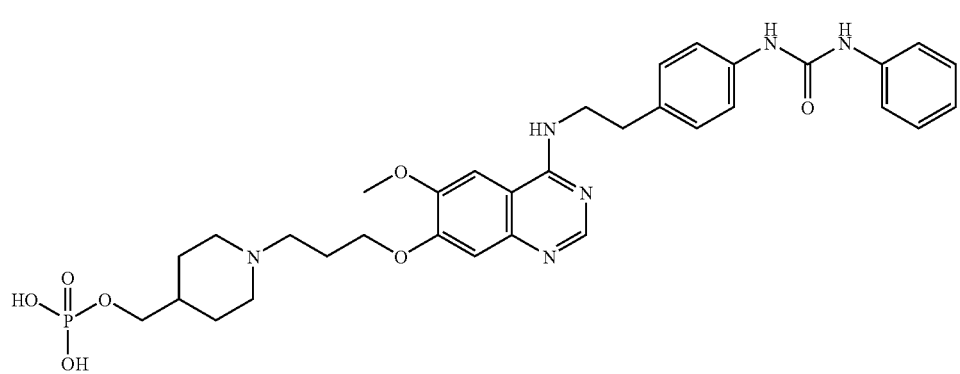
Compound 34
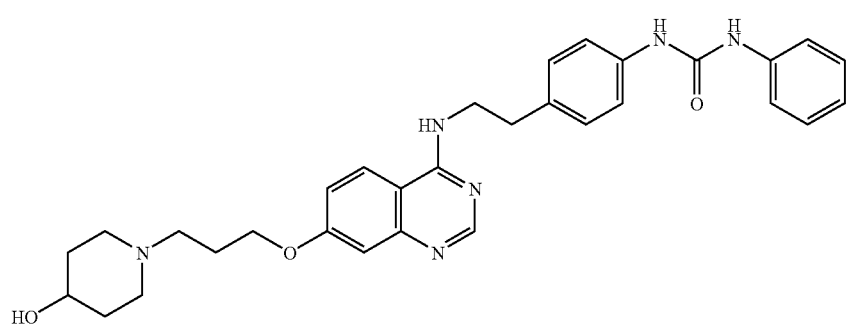

Compound 35
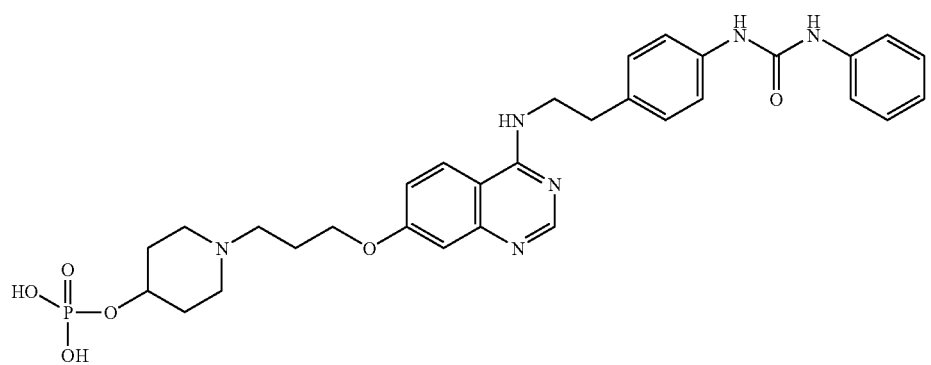
Compound 36
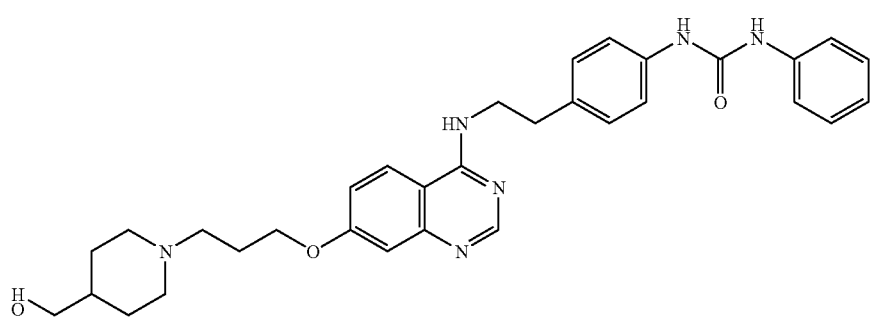
Compound 37
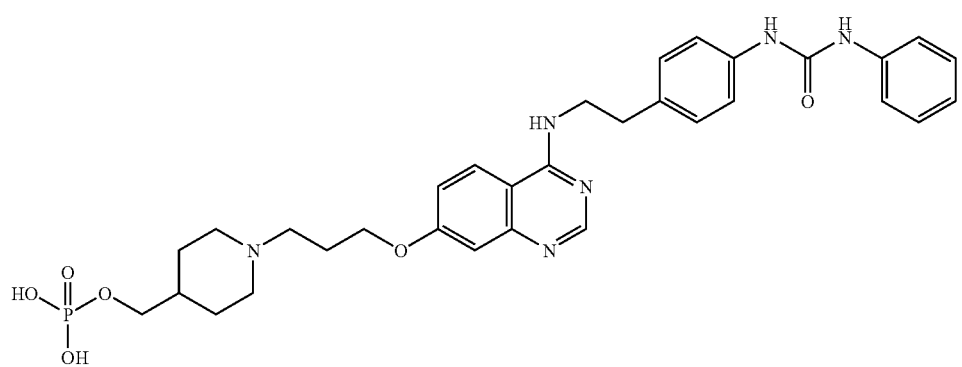
Compound 38
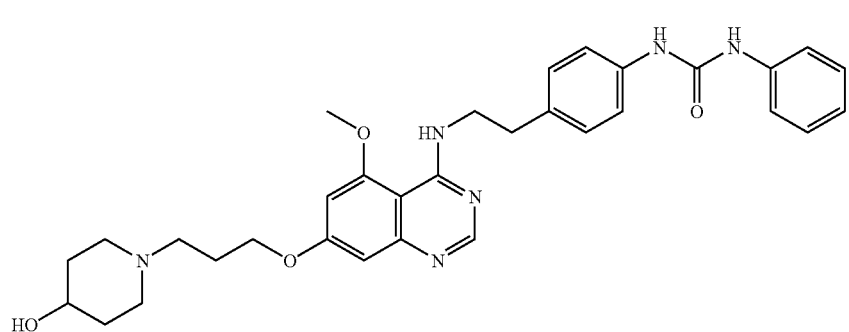

-continued
Compound 39
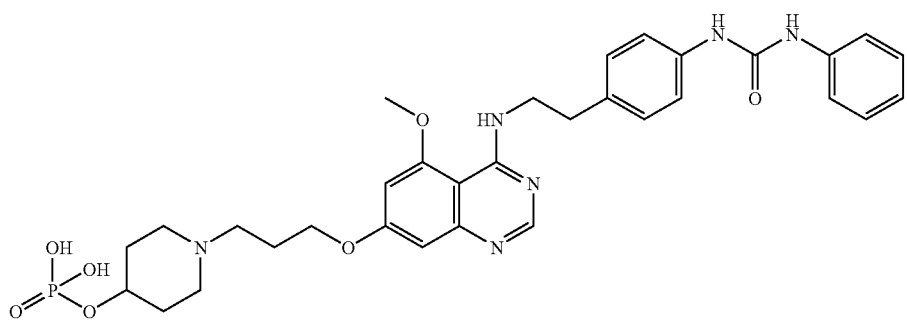
Compound 40
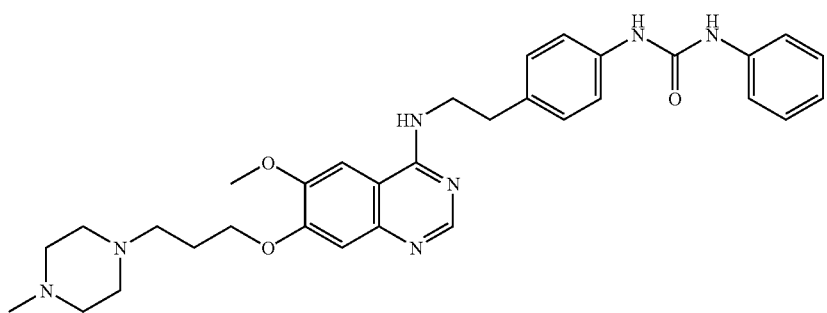
Compound 41
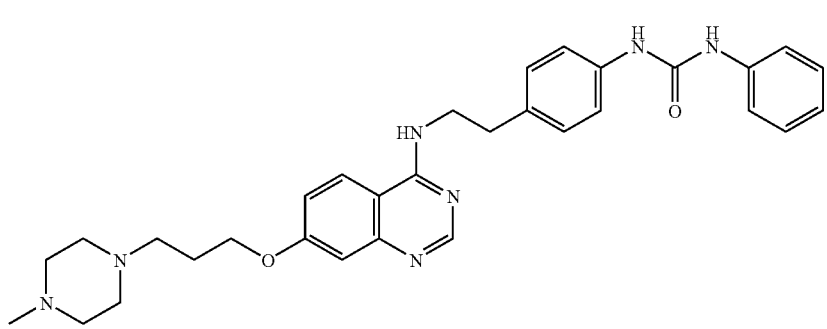
Compound 42
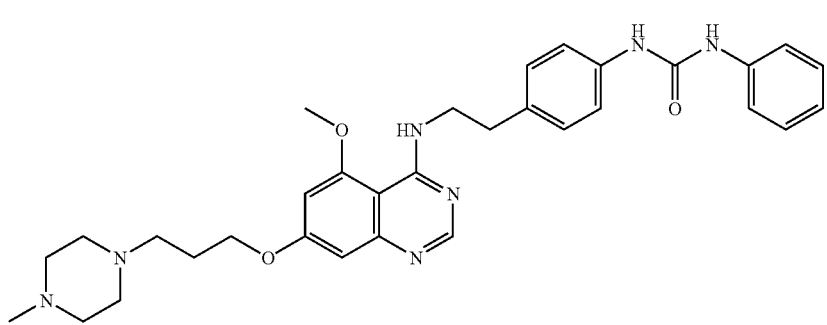
Compound 43
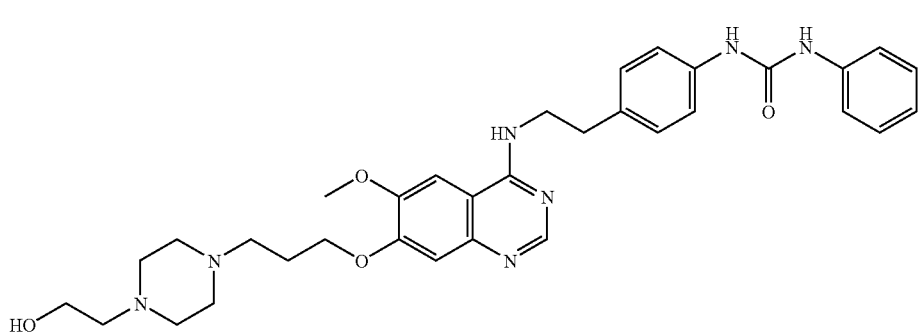

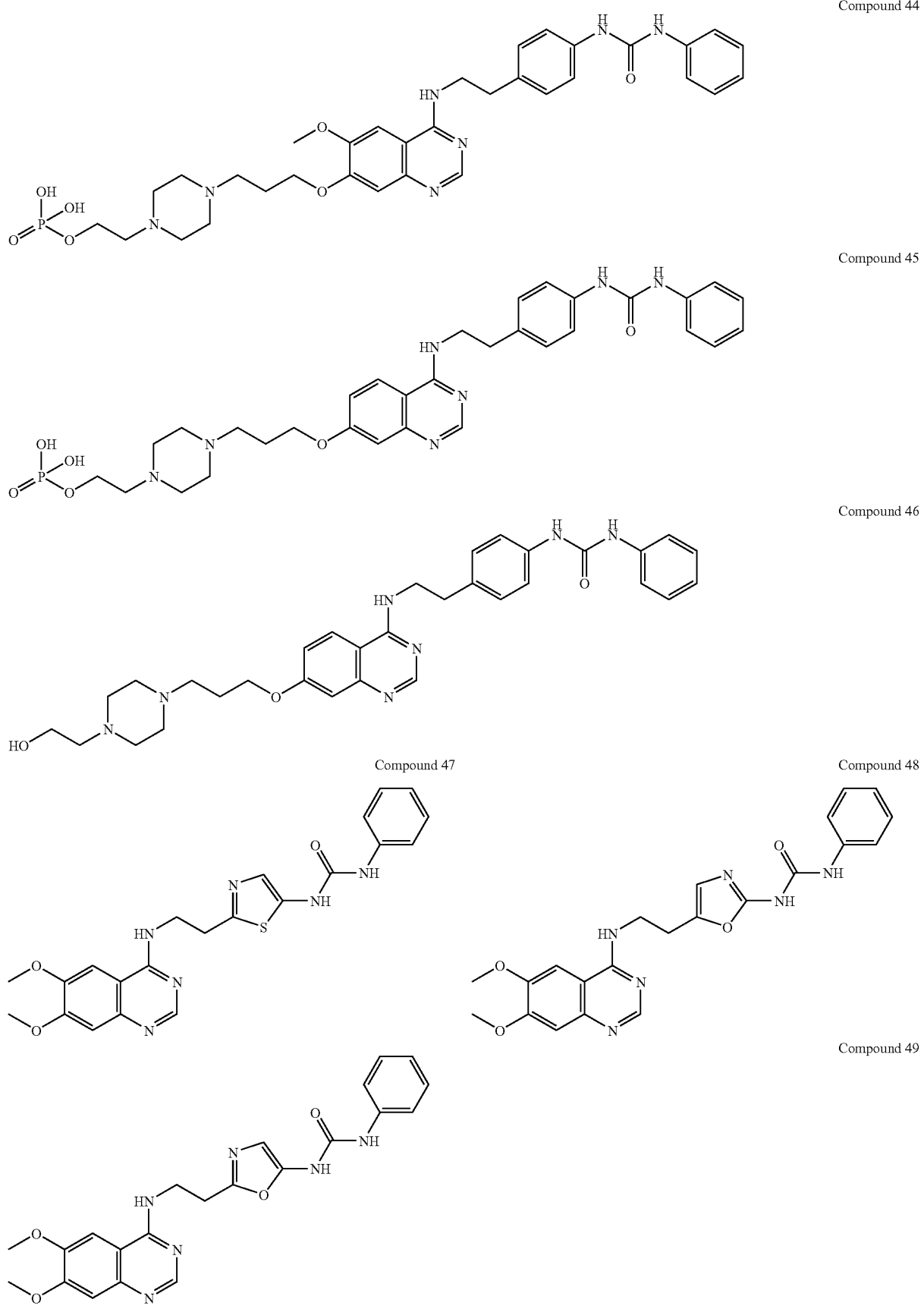

-continued
Compound 50
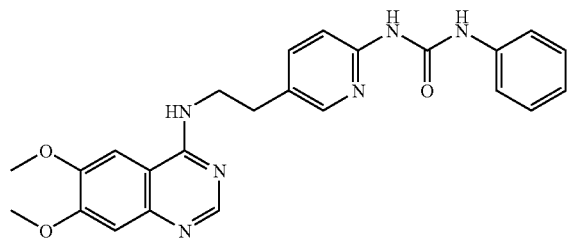
Compound 51
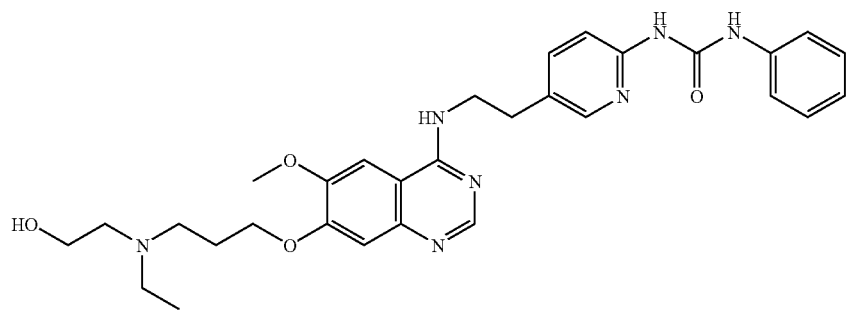
Compound 52
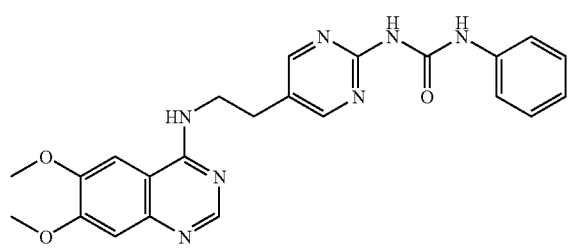
Compound 53
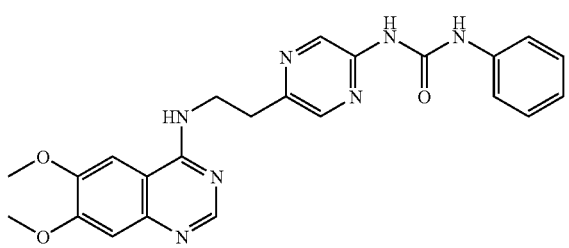
Compound 54
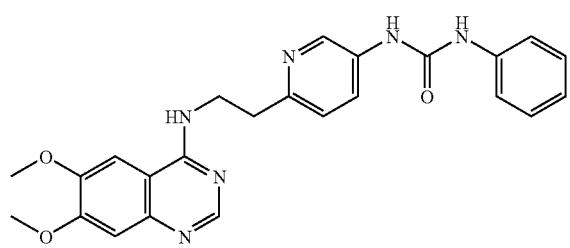
Compound 55
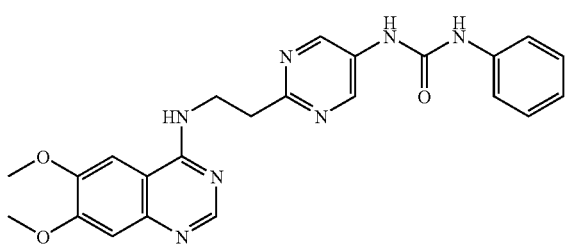
Compound 56
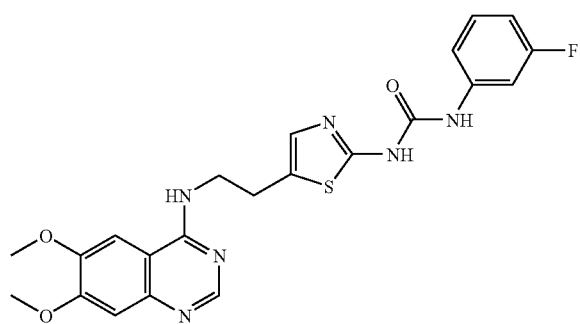
Compound 57
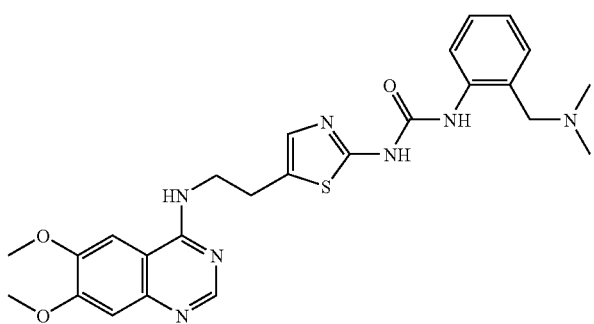

-continued
Compound 58
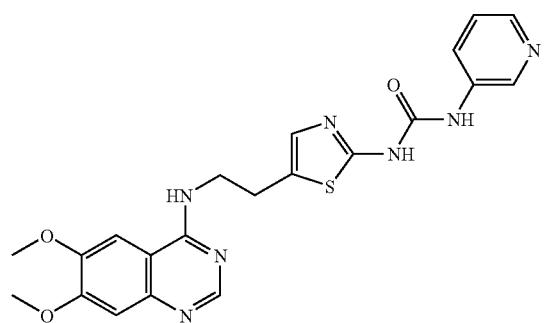
Compound 59
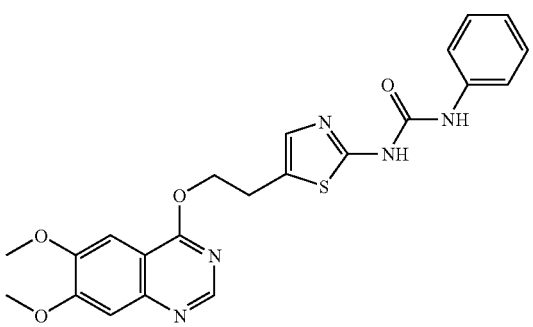
Compound 60
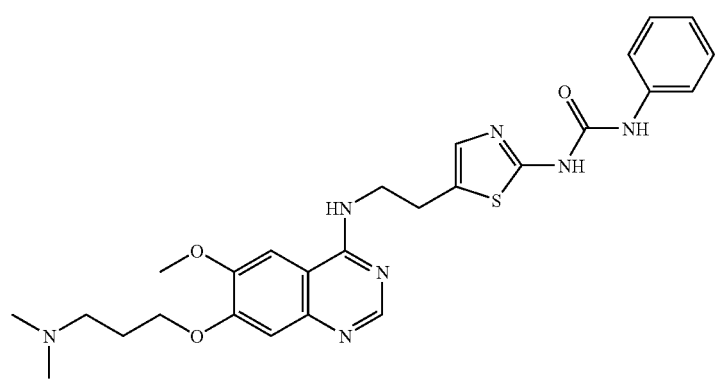
Compound 61
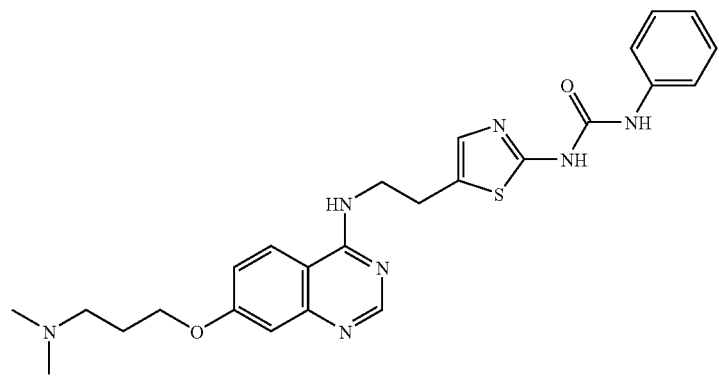
Compound 62
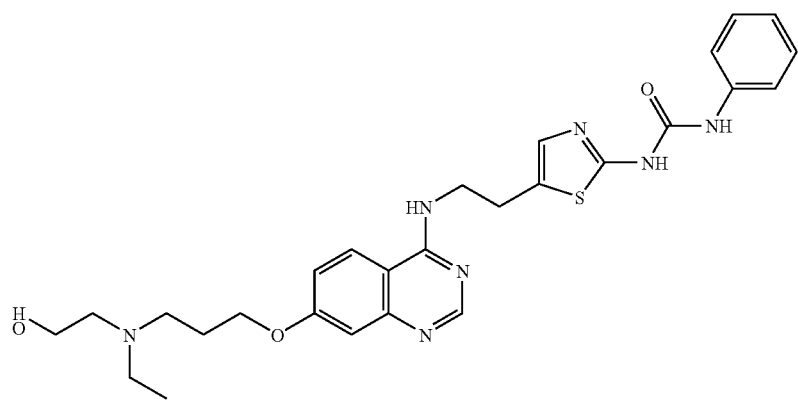

-continued
Compound 63
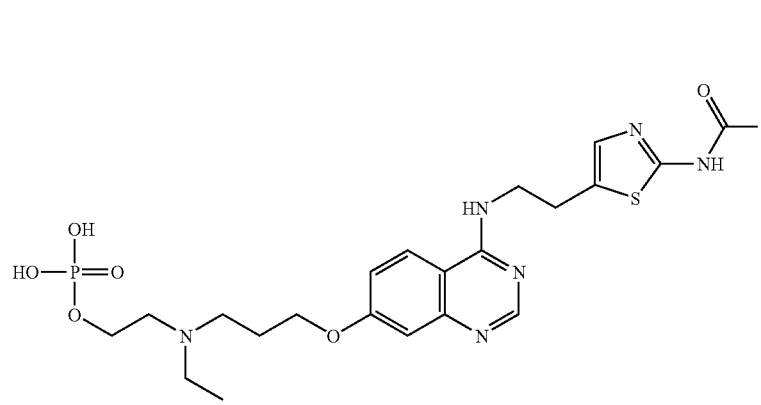
Compound 64
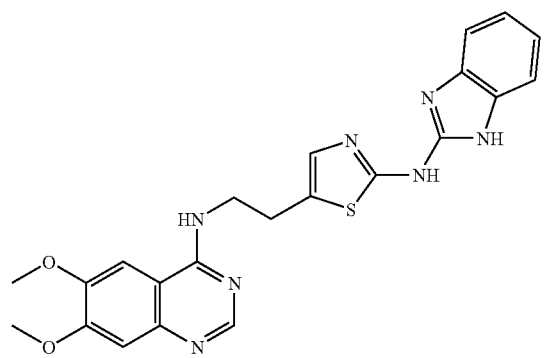
Compound 65
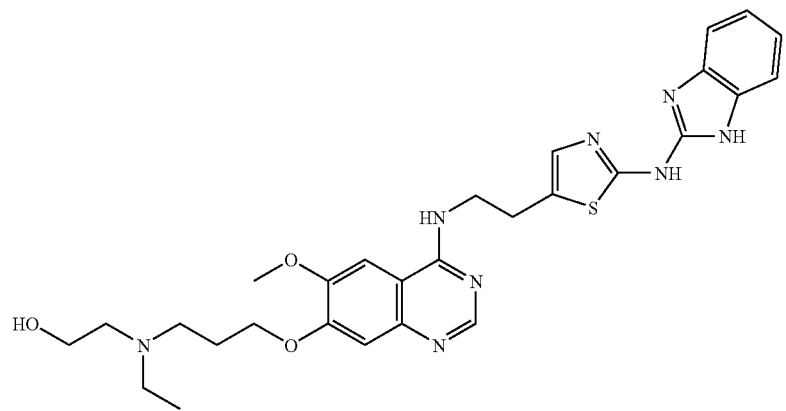
Compound 66
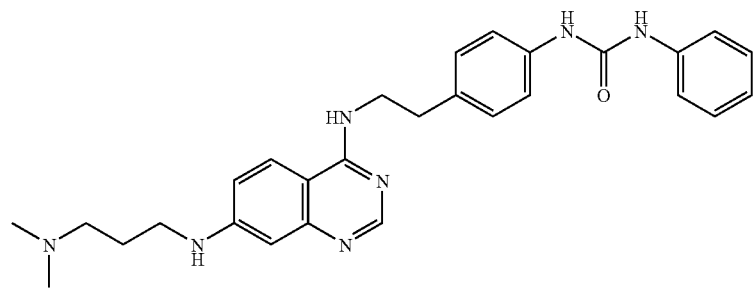

-continued
Compound 67
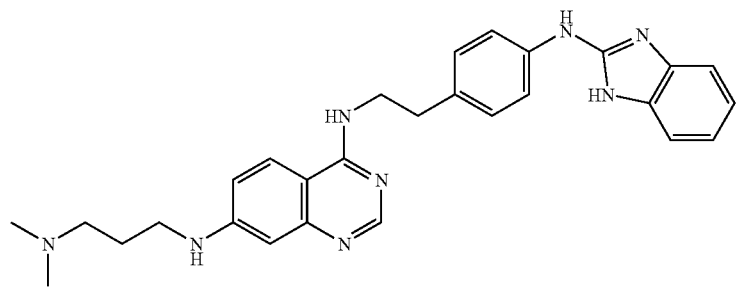
Compound 68
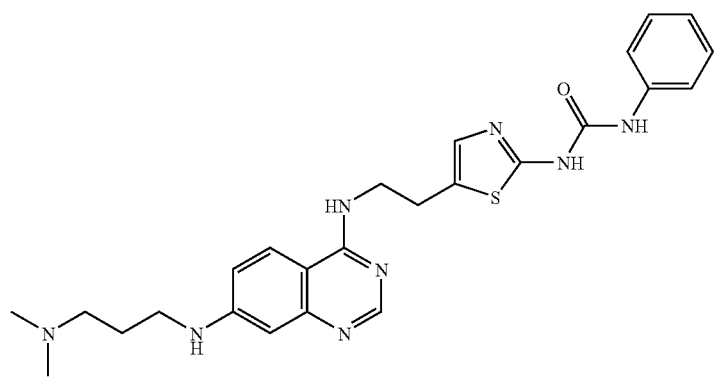
Compound 69
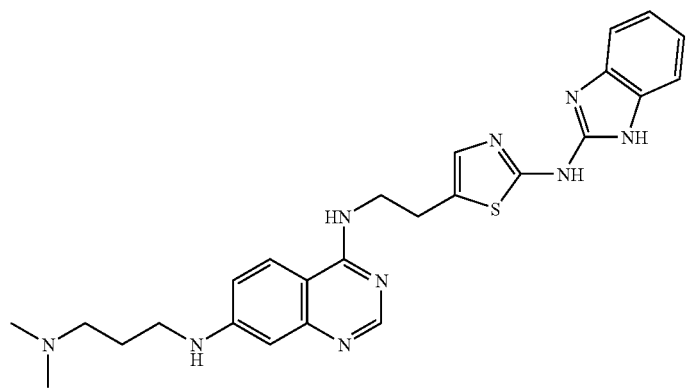
Compound 70
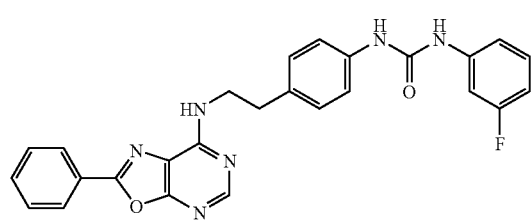
Compound 71
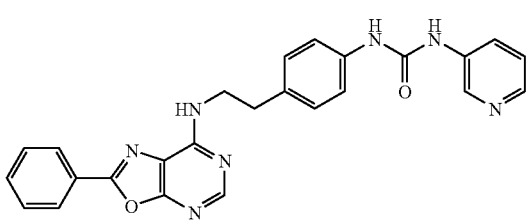
Compound 72
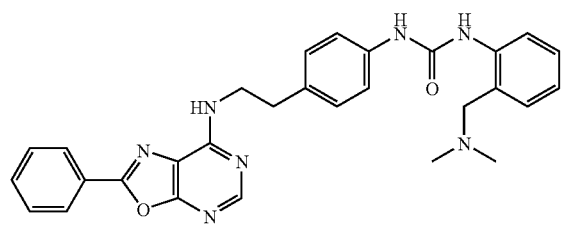

-continued
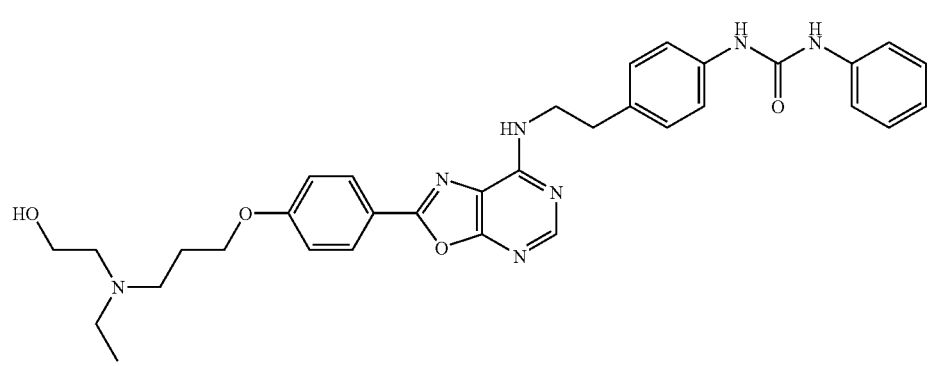
Compound 73
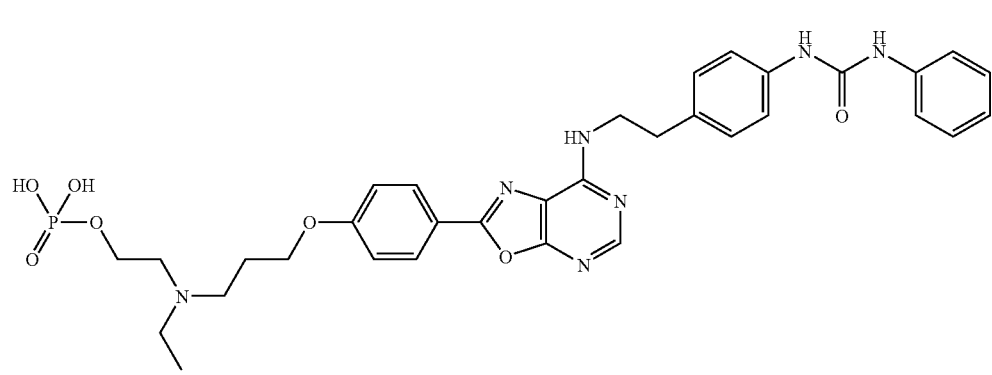
Compound 74
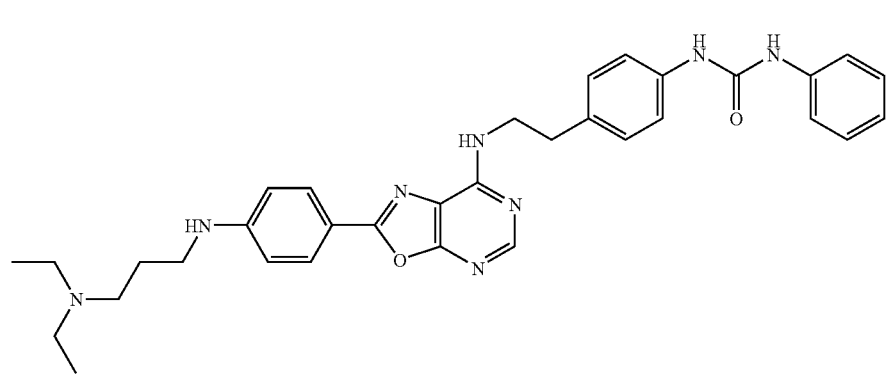
Compound 75
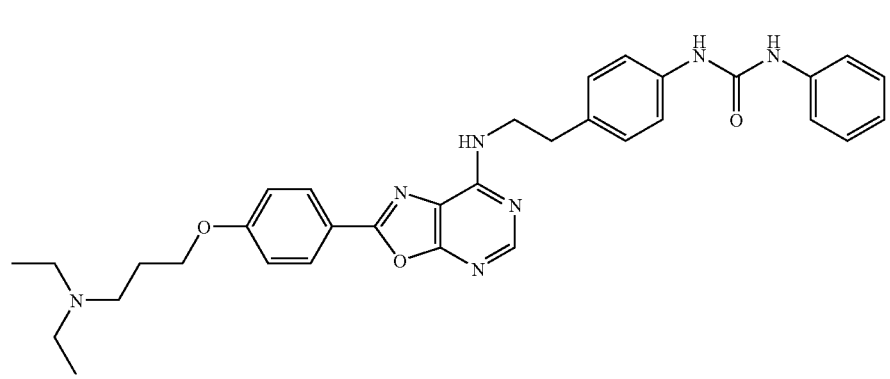
Compound 76

-continued
Compound 77
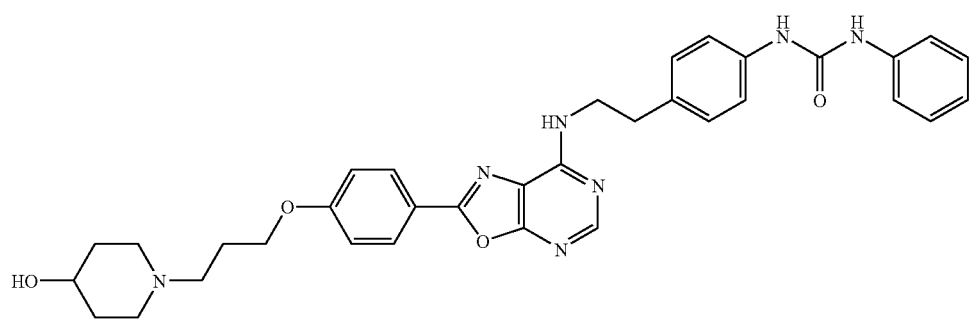
Compound 78
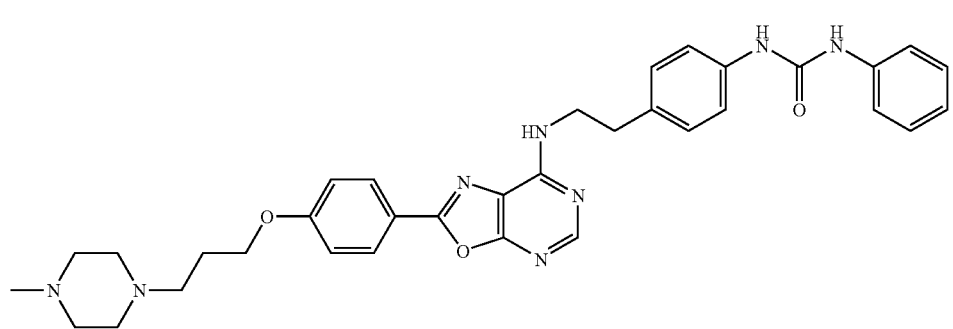
Compound 79
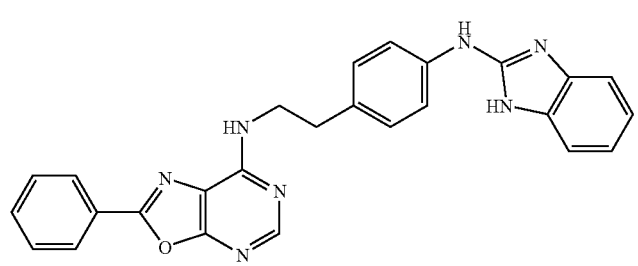
Compound 80
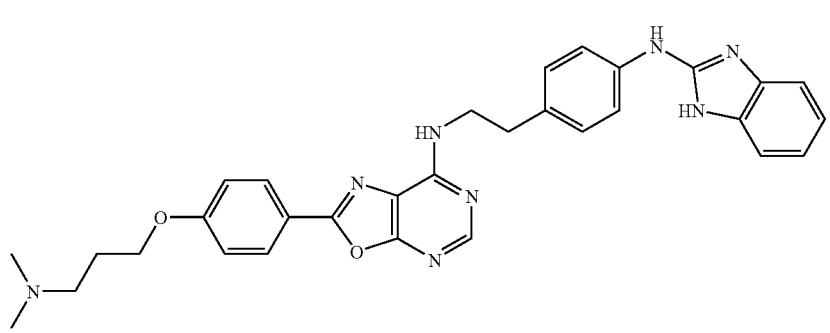
Compound 81
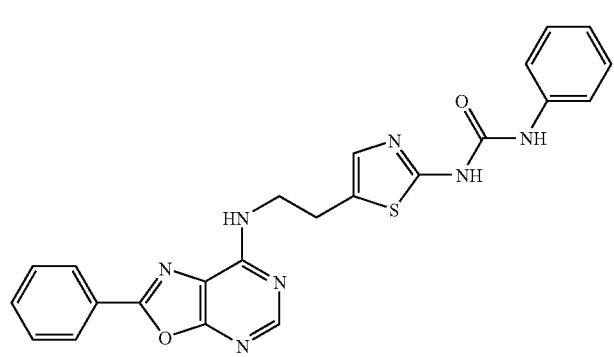

Compound 82
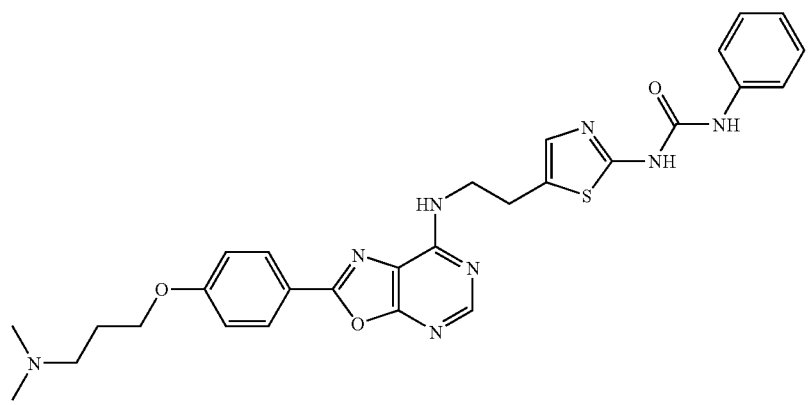
Compound 83
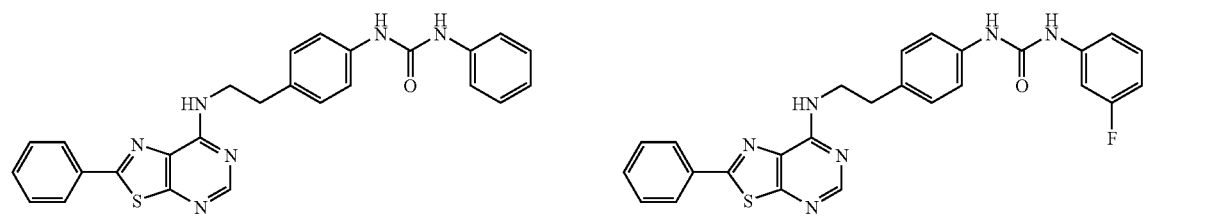
Compound 84
Compound 85
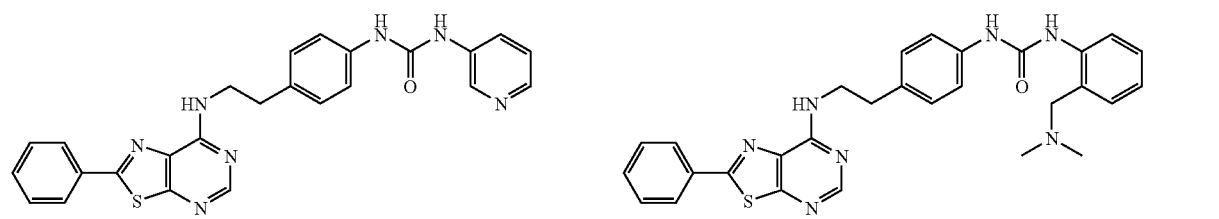
Compound 86
Compound 87
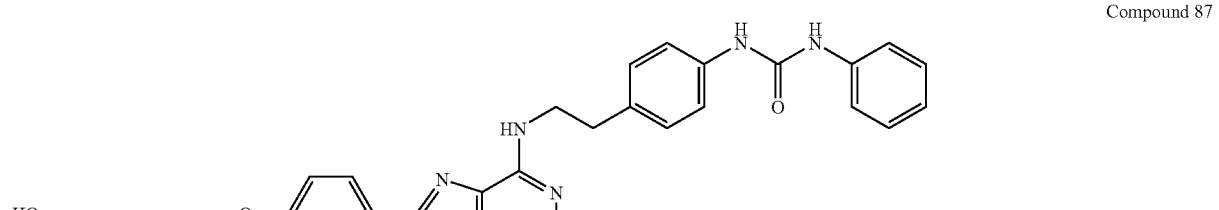
Compound 88
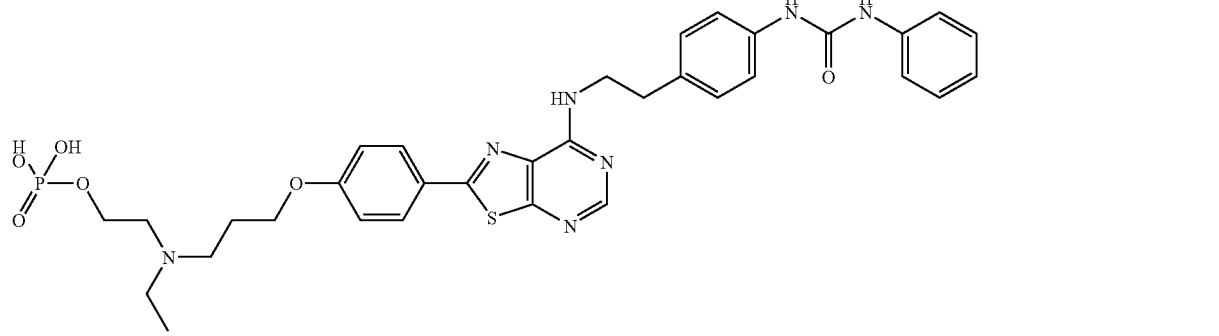

-continued
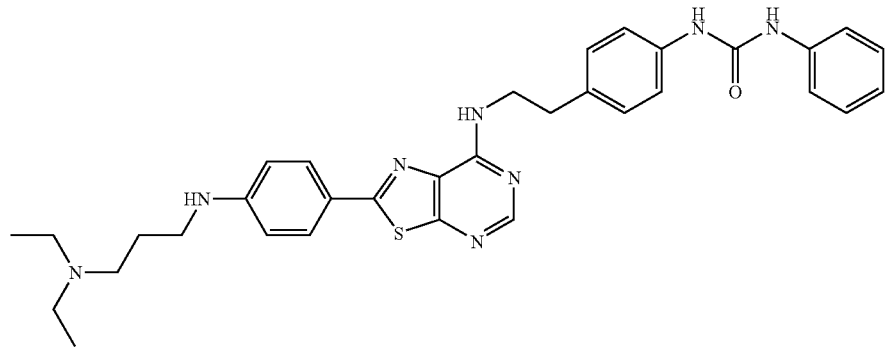
Compound 89
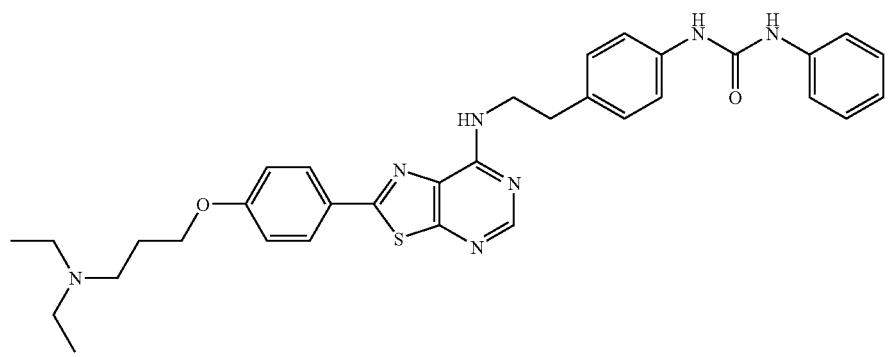
Compound 90
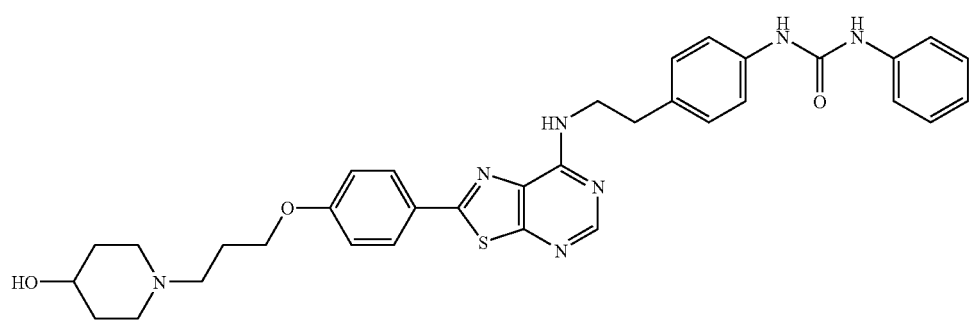
Compound 91
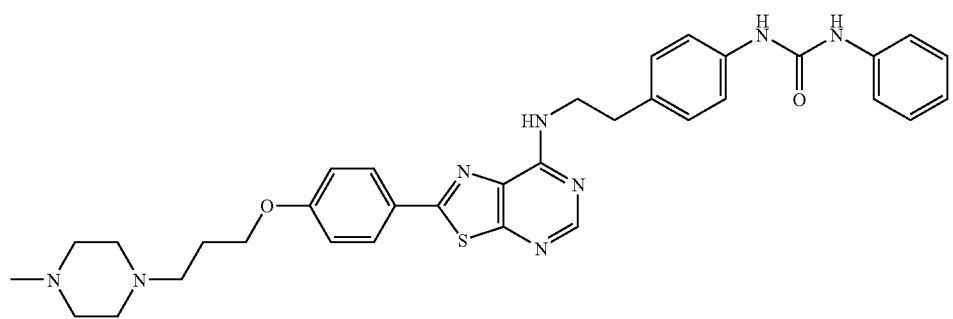
Compound 92
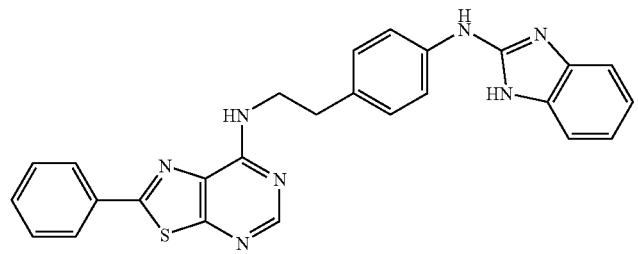
Compound 93

-continued
Compound 94
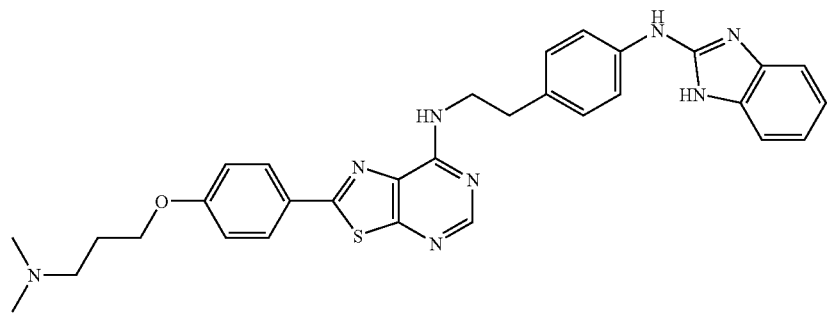
Compound 95
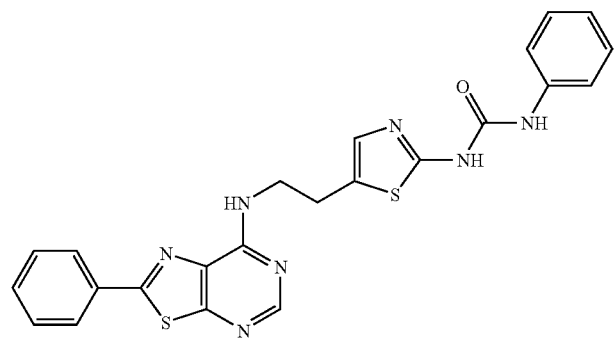
Compound 96
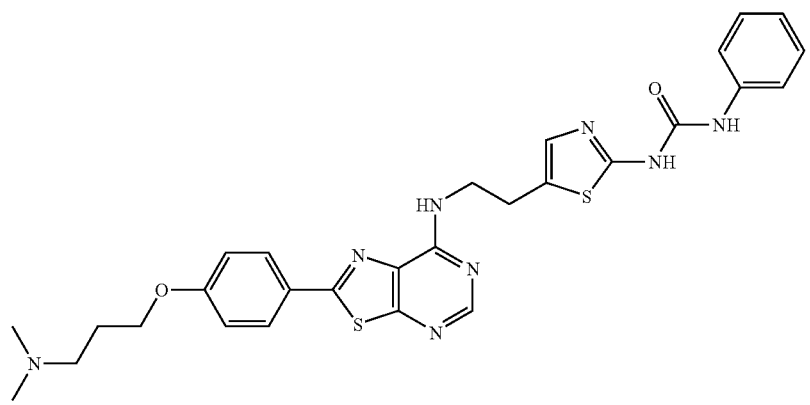
Compound 97
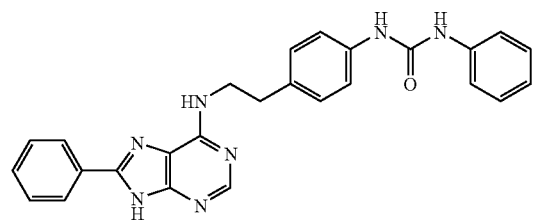
Compound 98
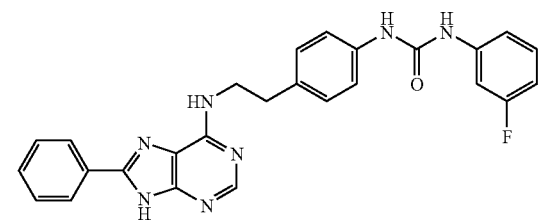
Compound 99
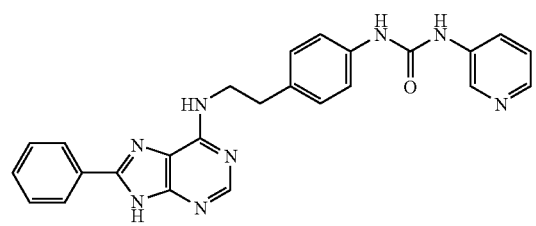
Compound 100
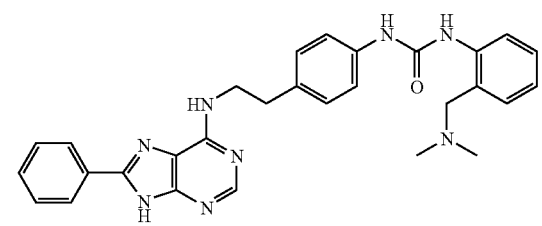

-continued
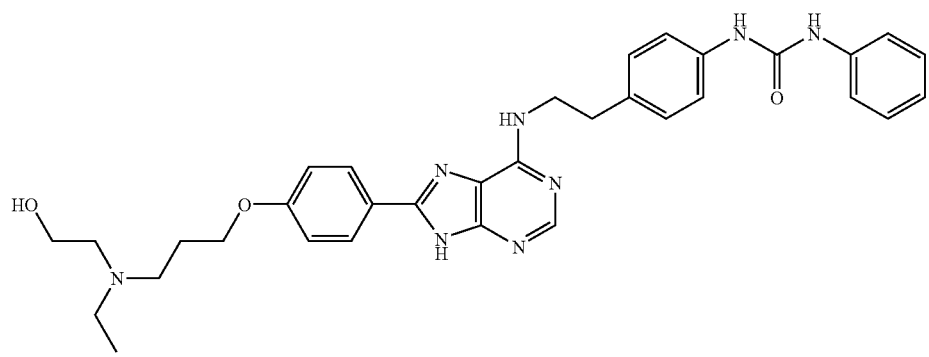
Compound 101
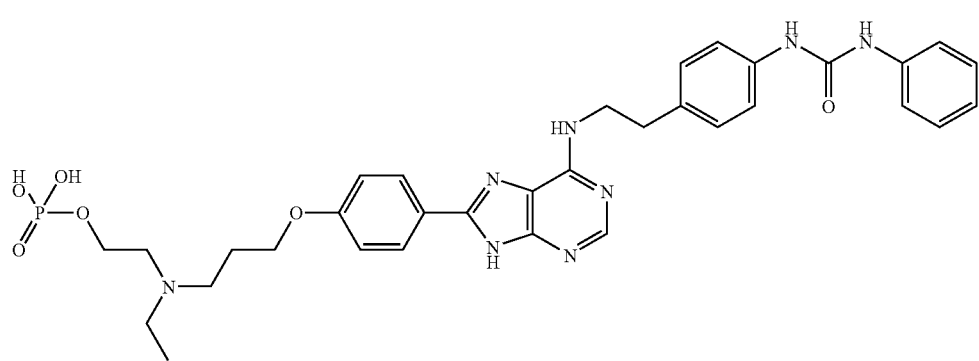
Compound 102
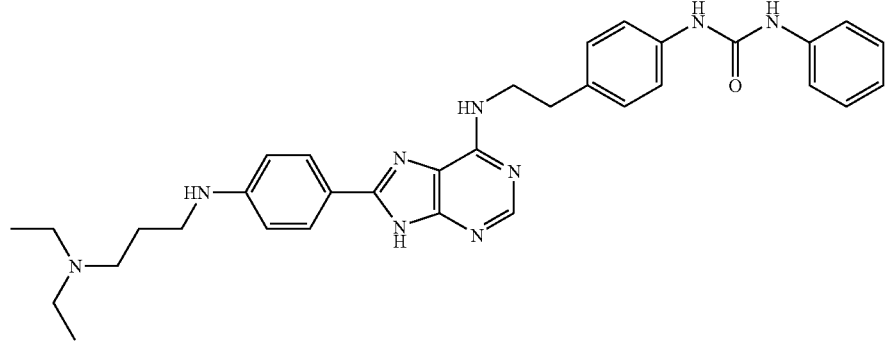
Compound 103
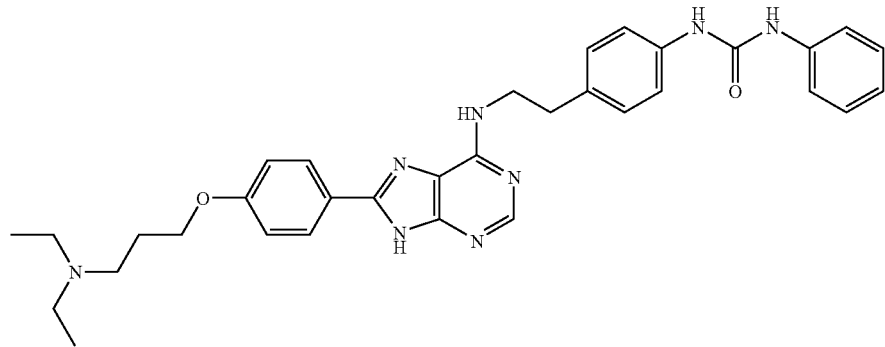
Compound 104

-continued
Compound 105
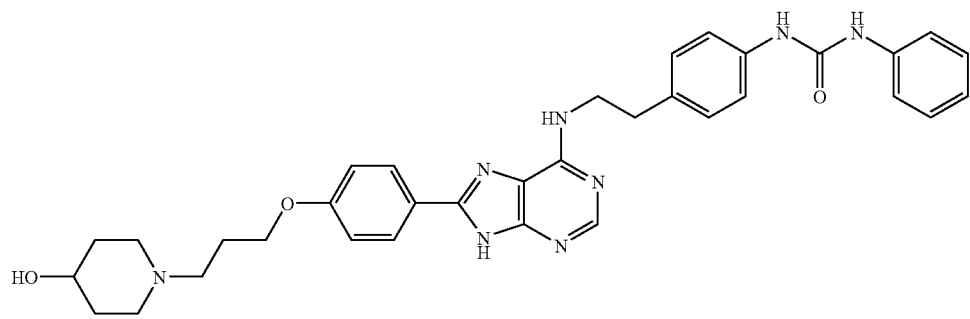
Compound 106
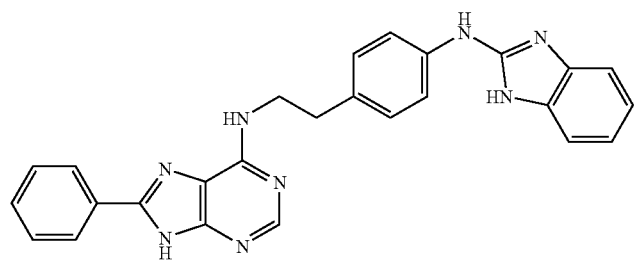
Compound 107
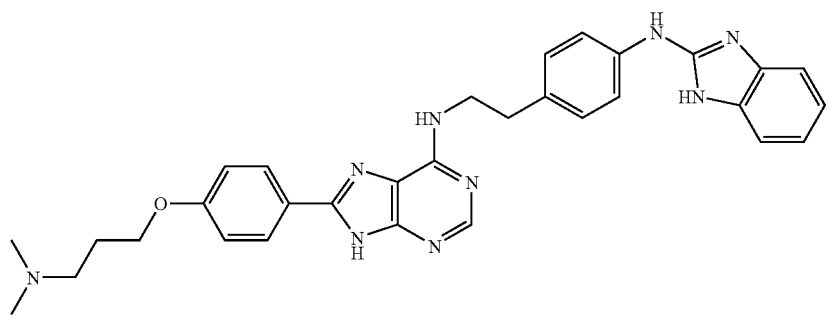
Compound 108
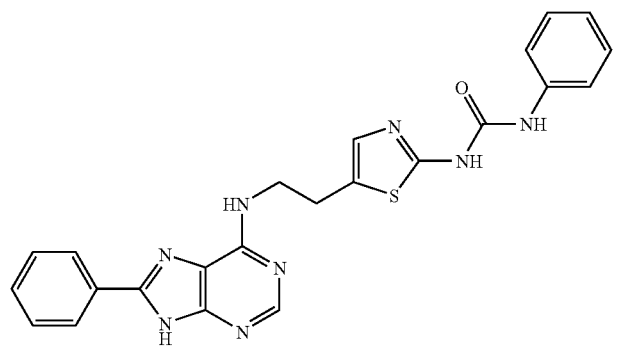
Compound 109
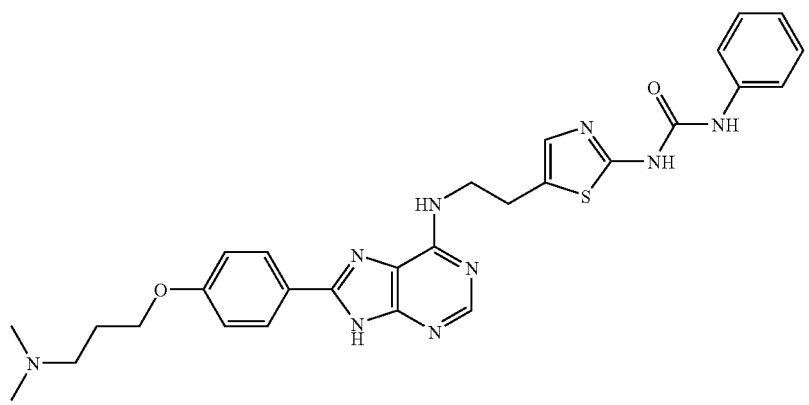

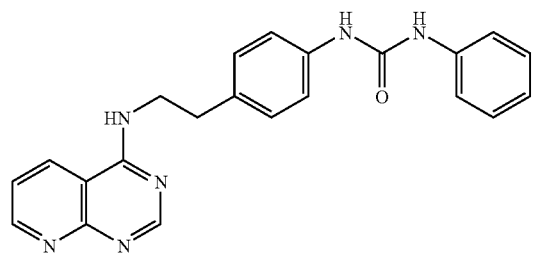
Compound 110
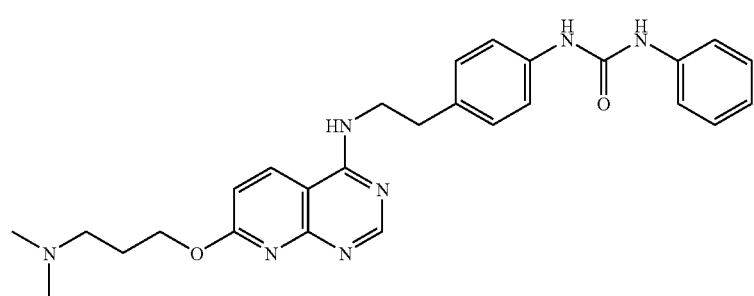
Compound 111
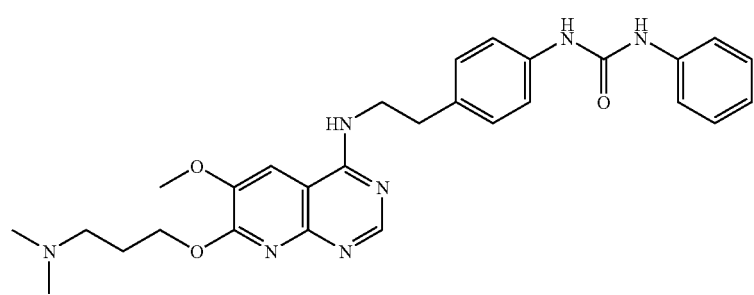
Compound 112
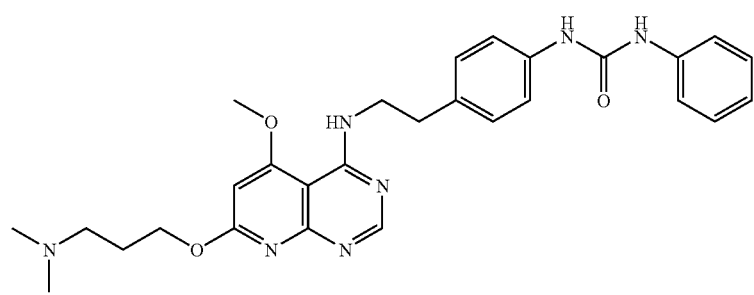
Compound 113
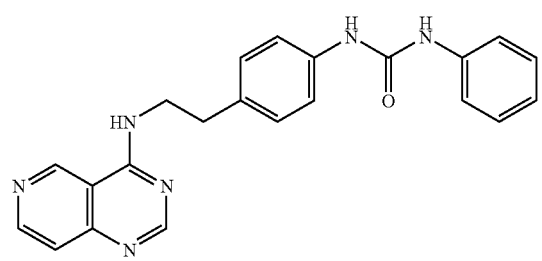
Compound 114

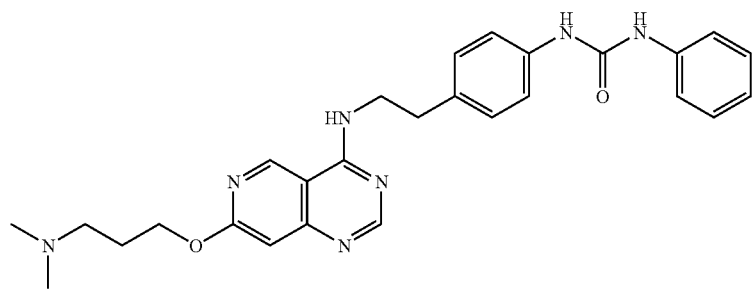
Compound 115
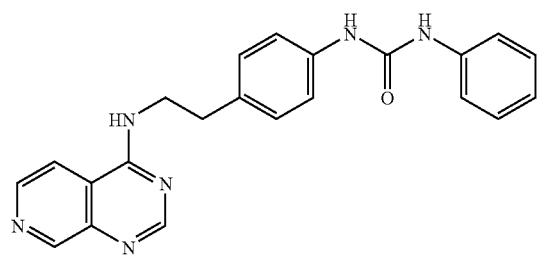
Compound 116
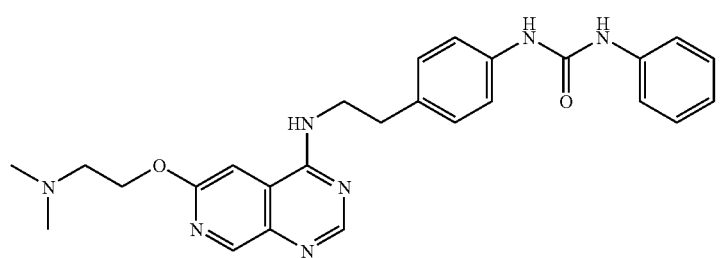
Compound 117
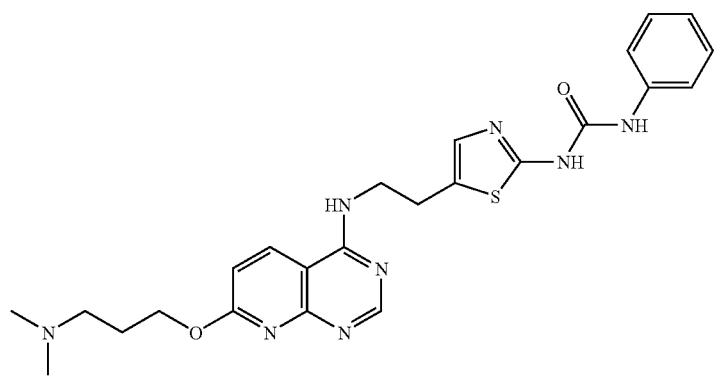
Compound 118
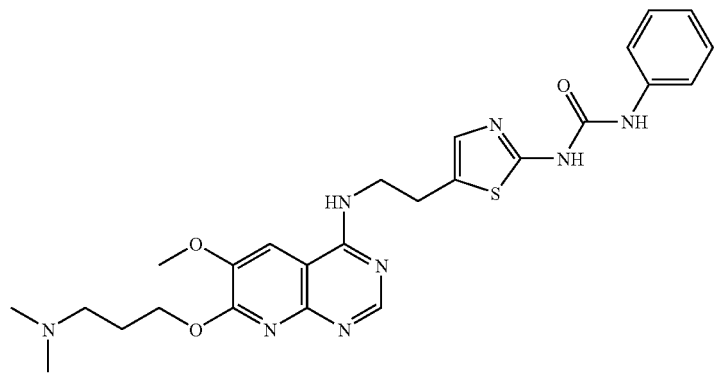
Compound 119

-continued
Compound 120
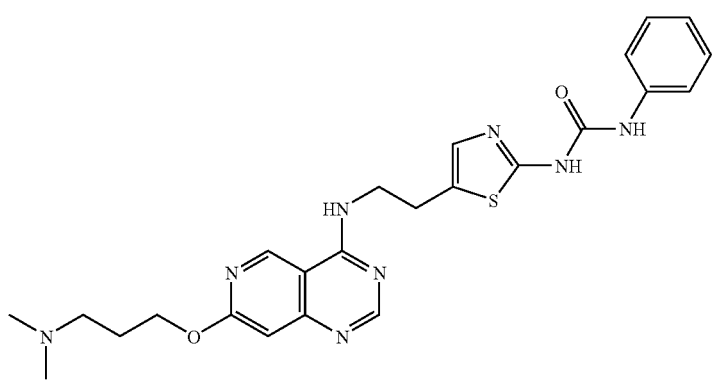
Compound 121
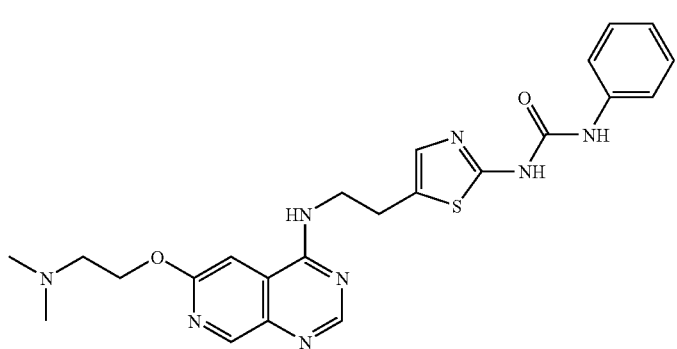
Compound 122
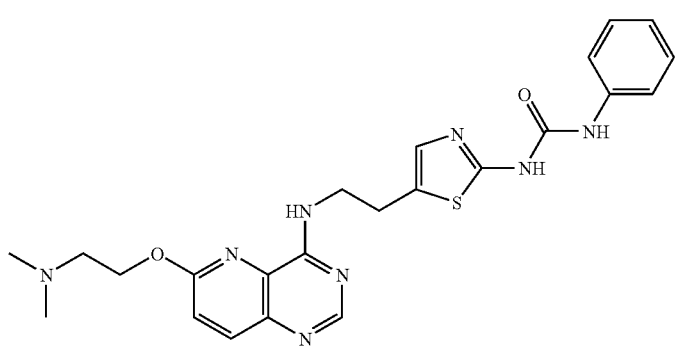
Compound 123
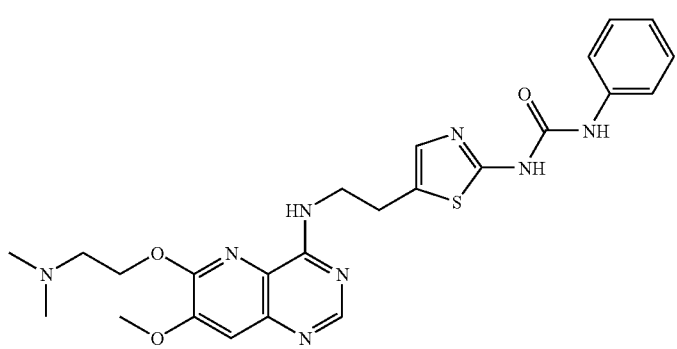

Compound 124
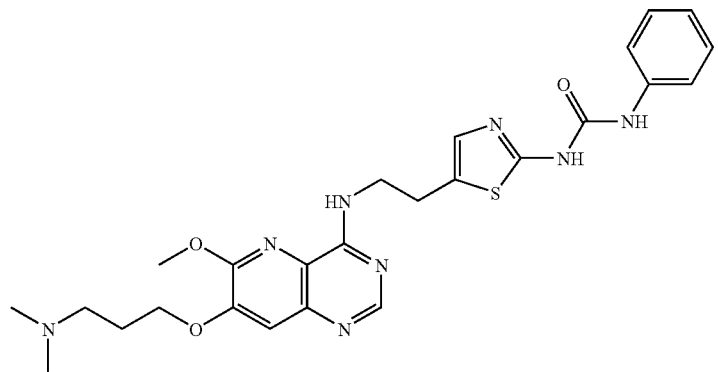
Compound 125
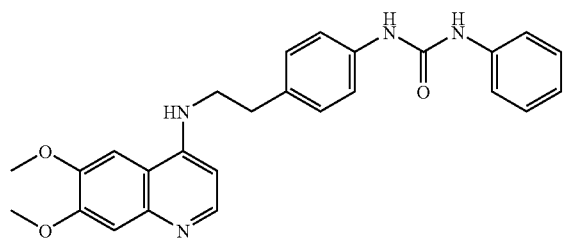
Compound 126
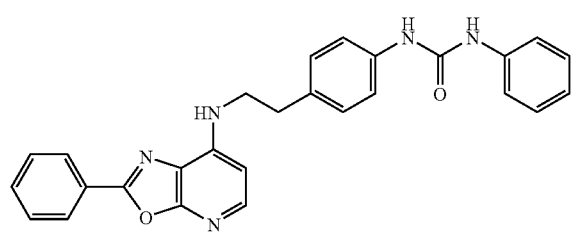
Compound 127
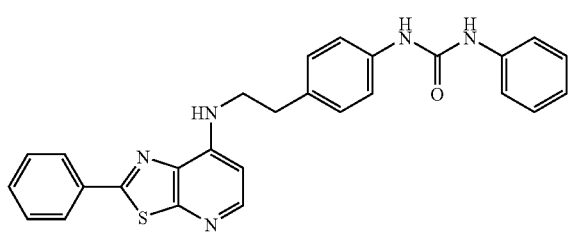
Compound 128
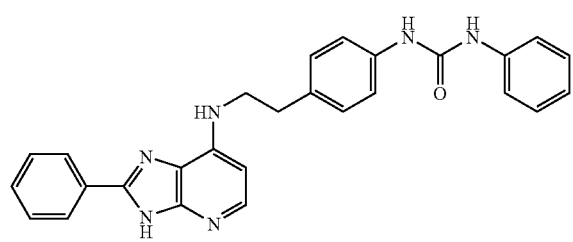
Compound 129
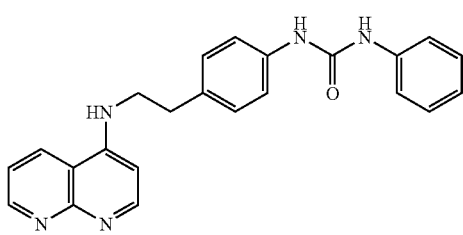
Compound 130
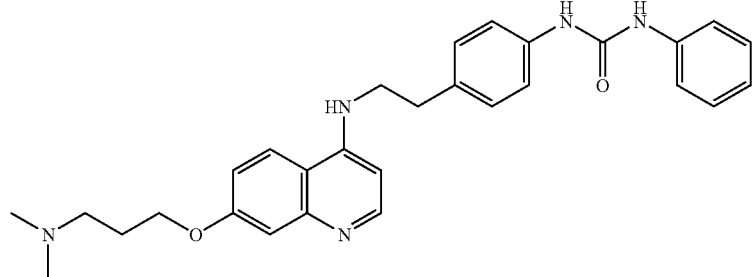

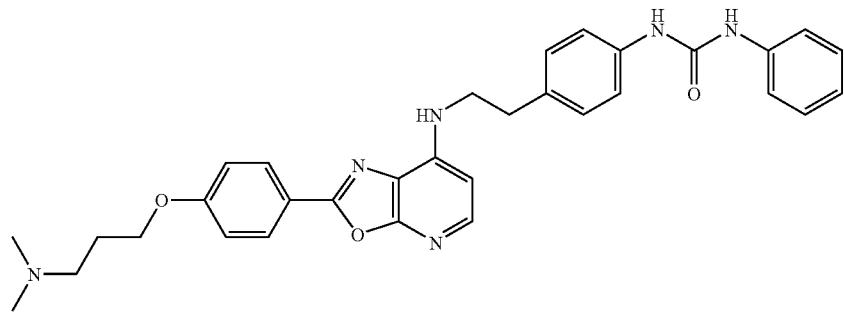
Compound 131
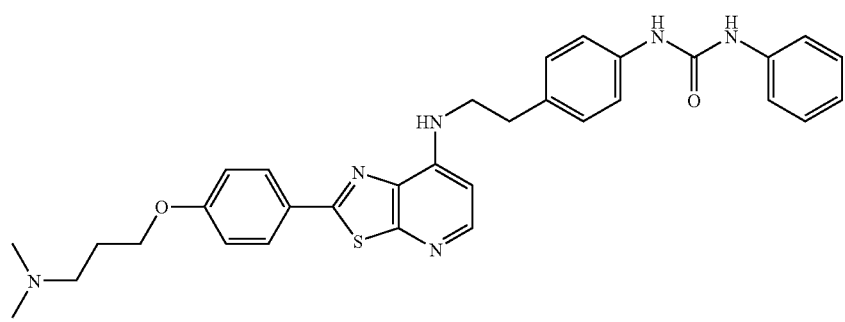
Compound 132
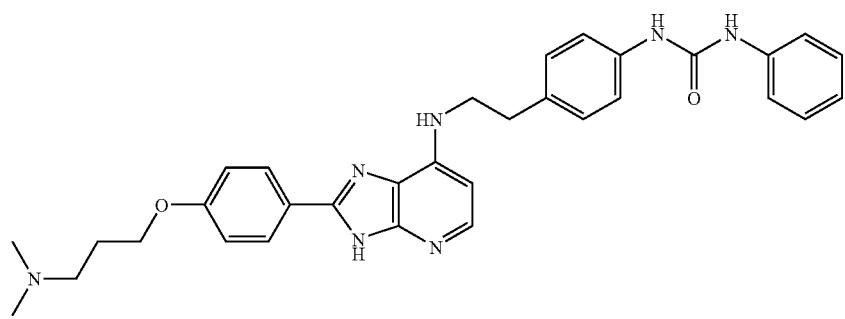
Compound 133
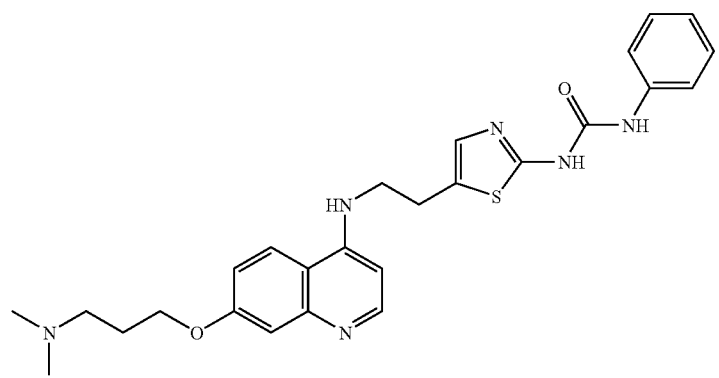
Compound 134

-continued
Compound 135
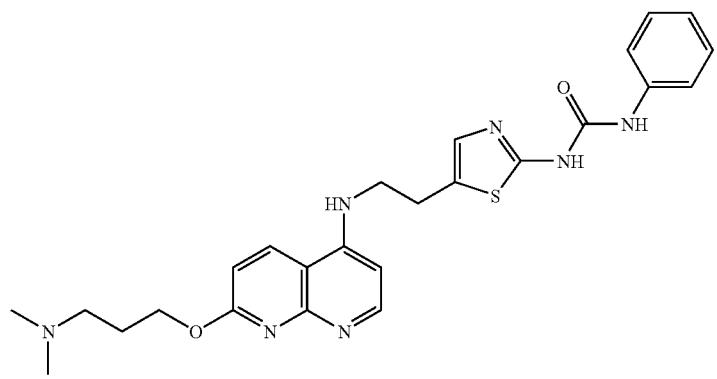
Compound 136
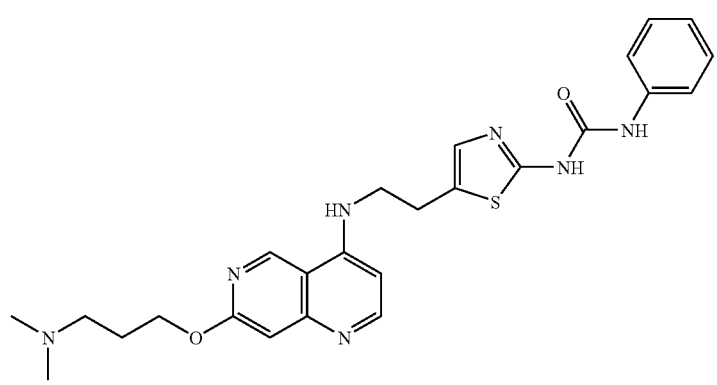
Compound 137
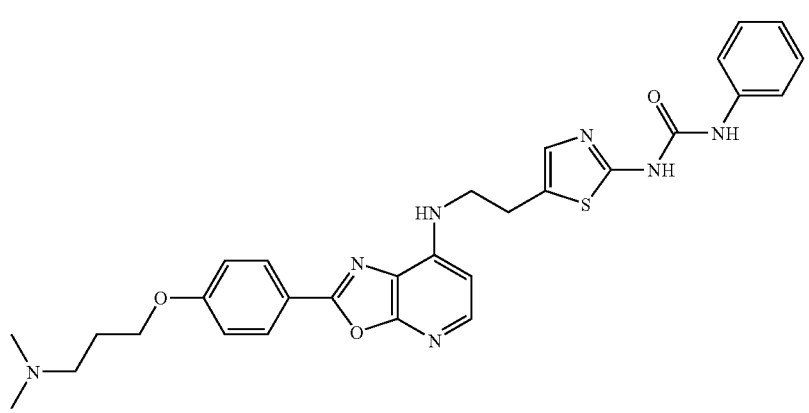
Compound 138
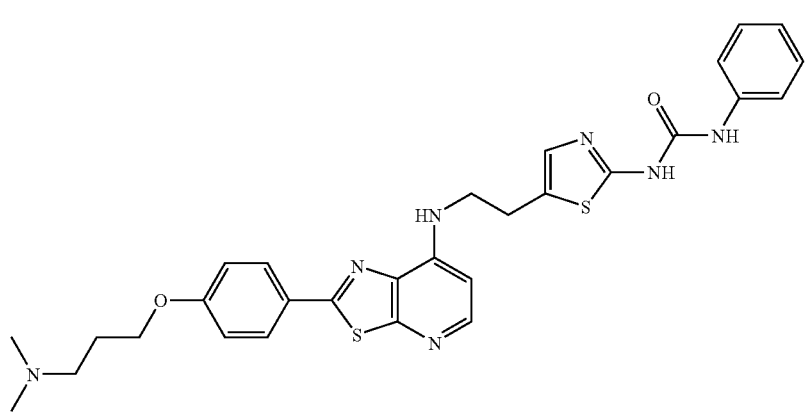

-continued
Compound 139
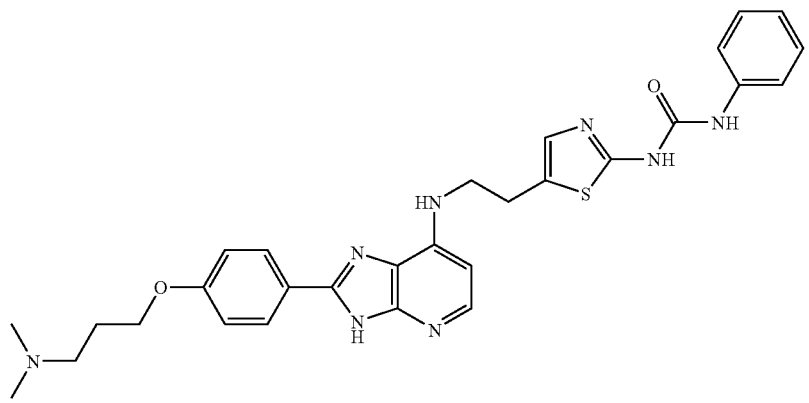
Compound 140
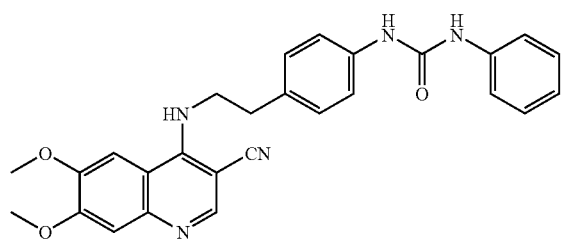
Compound 141
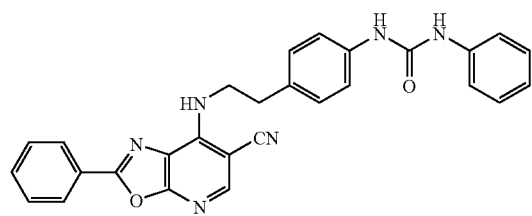
Compound 142
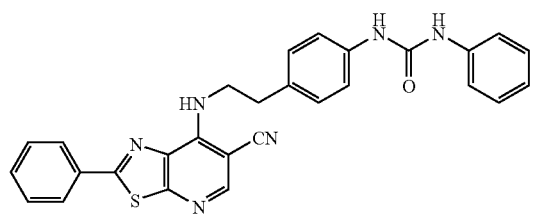
Compound 143
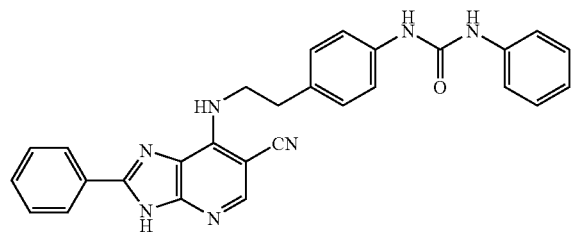
Compound 144
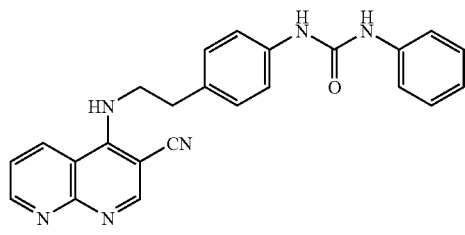
Compound 145
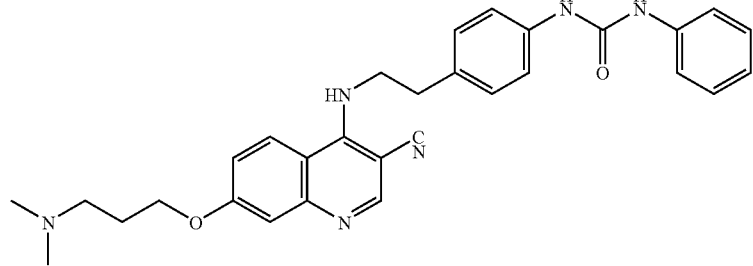

-continued
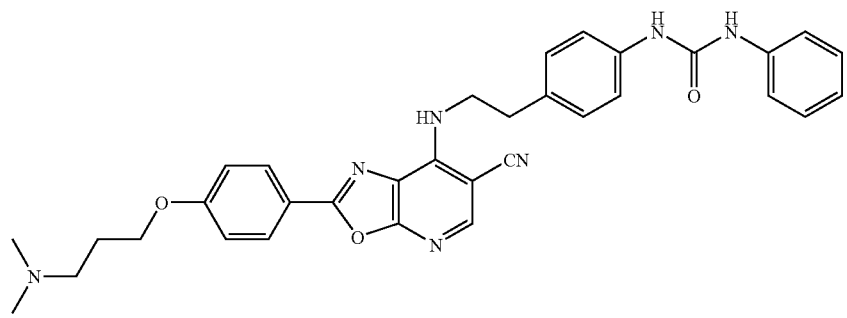
Compound 146
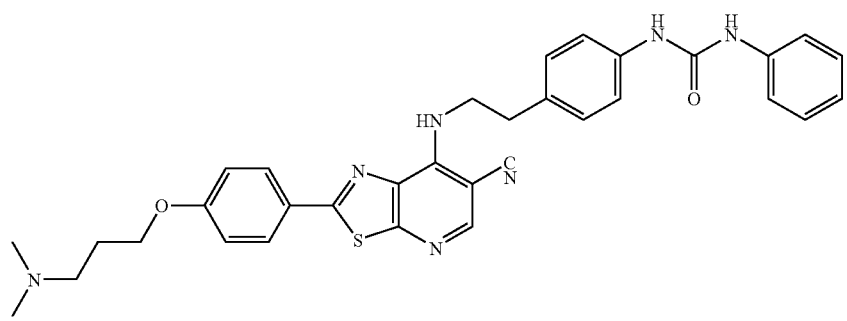
Compound 147
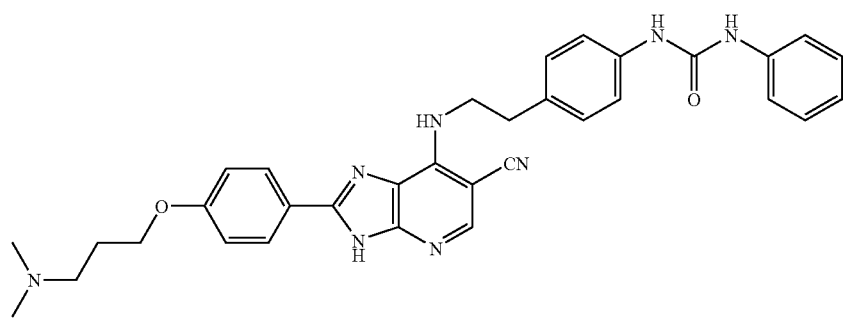
Compound 148
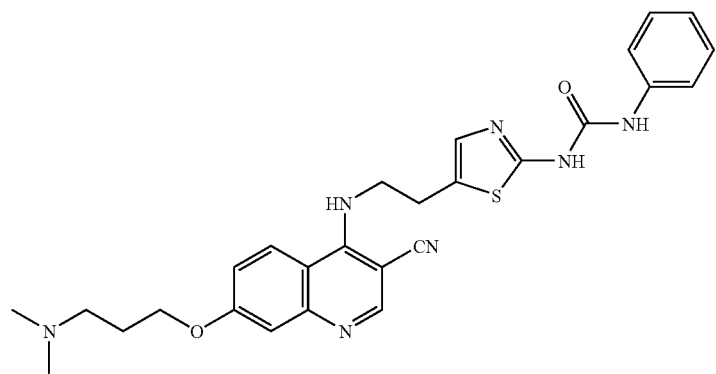
Compound 149

-continued
Compound 150
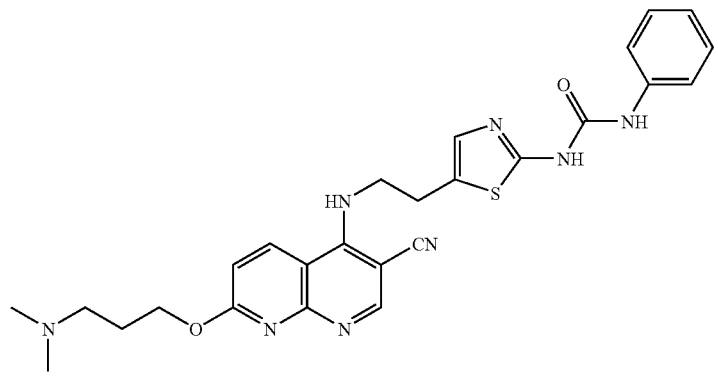
Compound 151
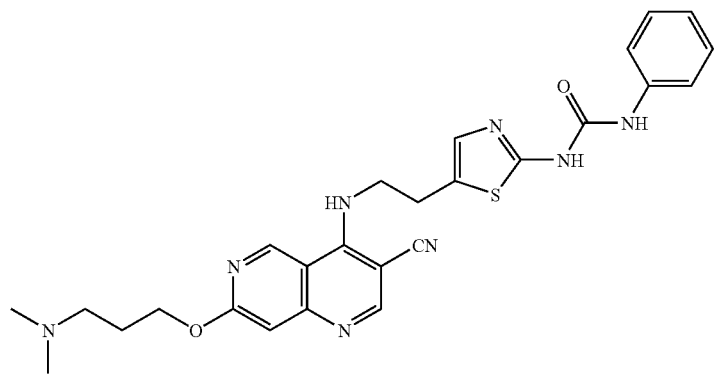
Compound 152
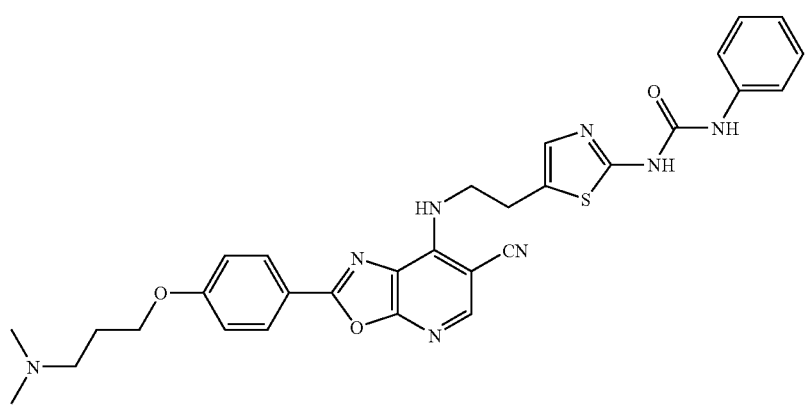
Compound 153
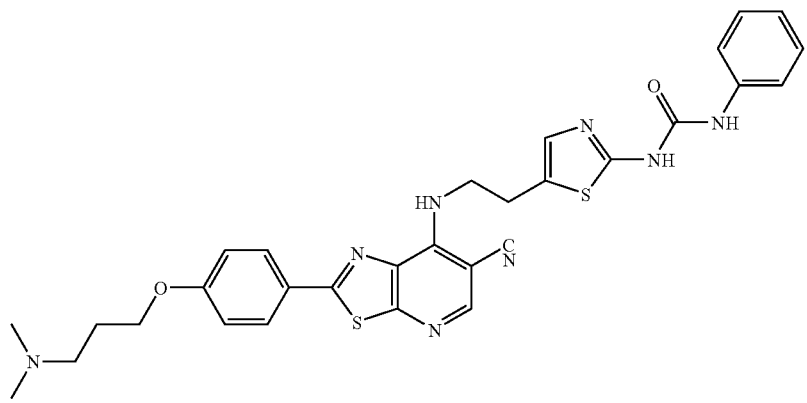

-continued
Compound 154
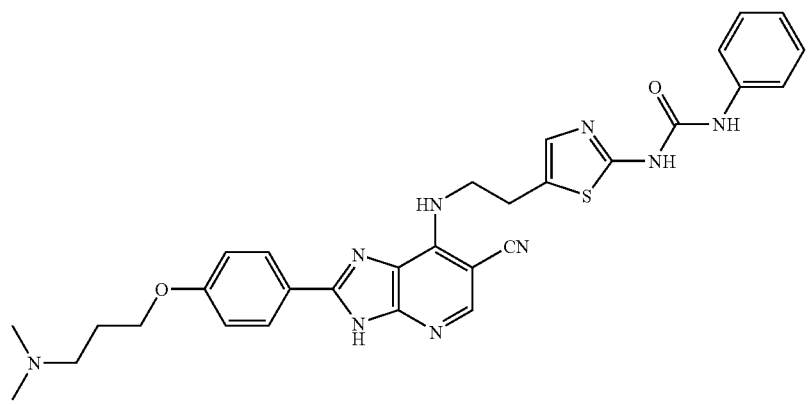
Compound 155
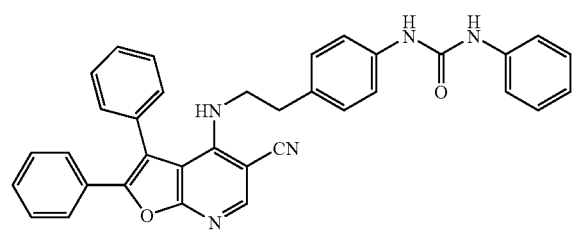
Compound 156
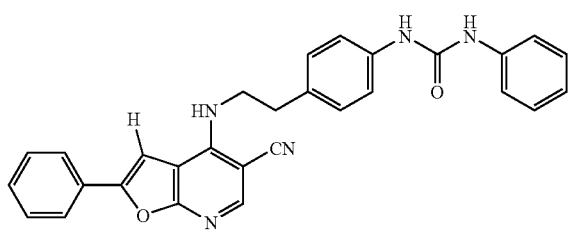
Compound 157
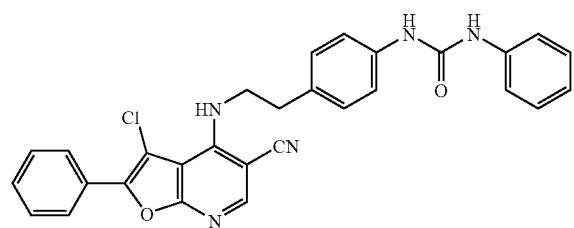
Compound 158
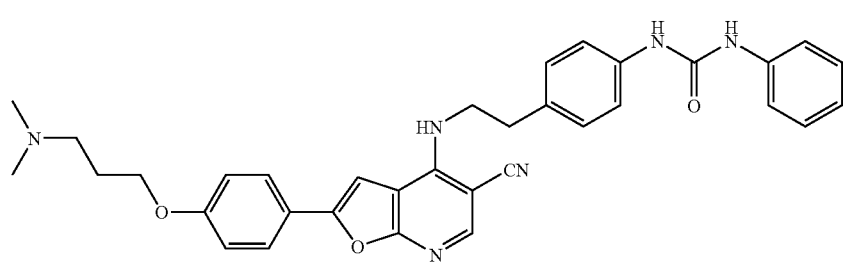
Compound 159
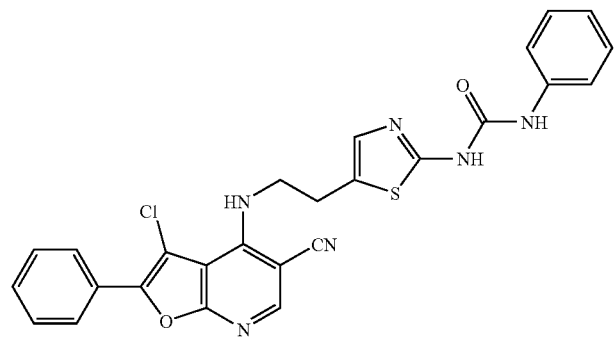

-continued
Compound 160
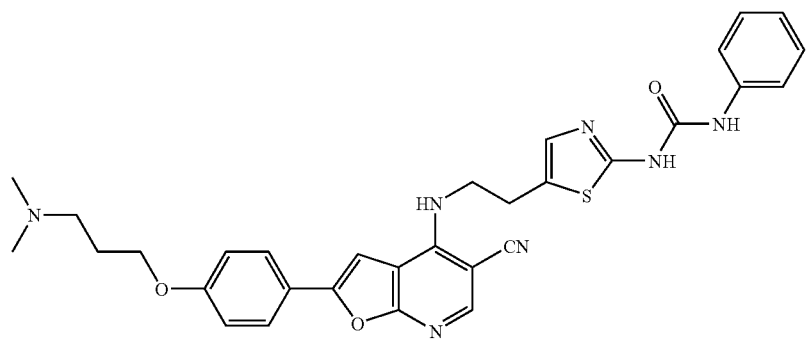
Compound 161
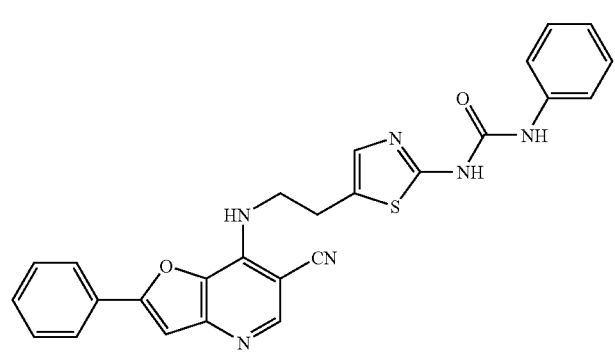
Compound 162
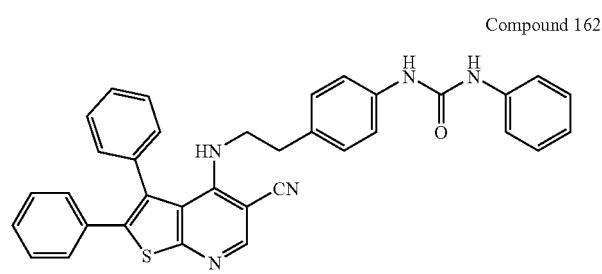
Compound 163
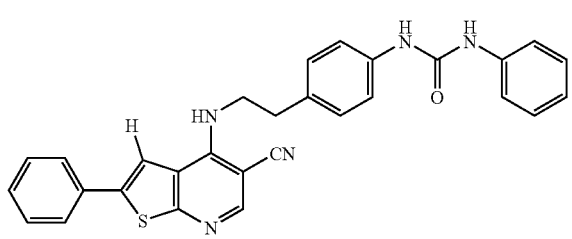
Compound 164
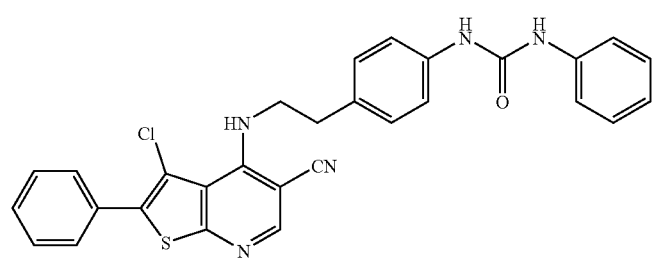
Compound 165
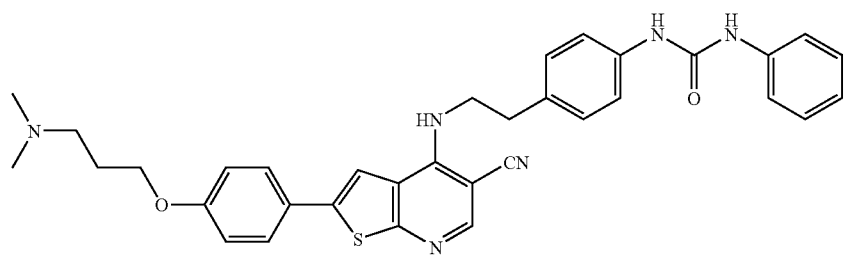

-continued
Compound 166
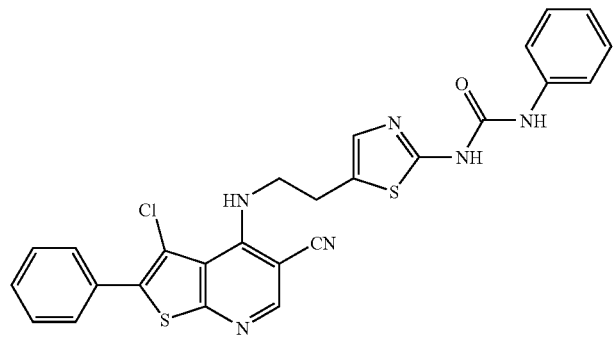
Compound 167
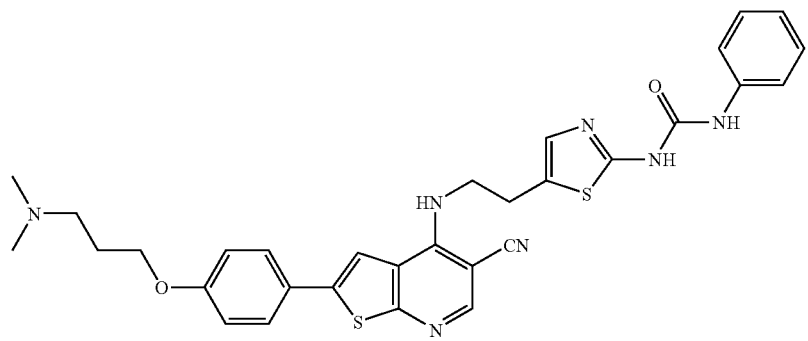
Compound 168
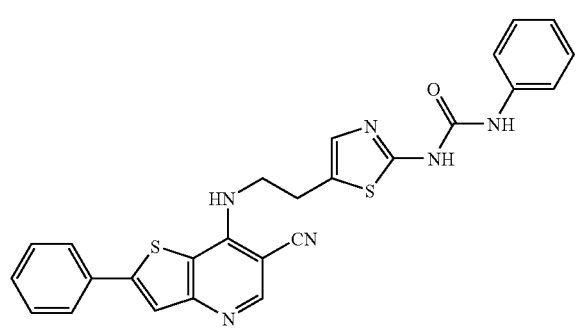
Compound 169
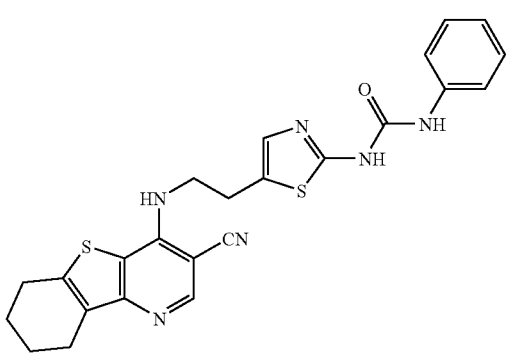
Compound 170
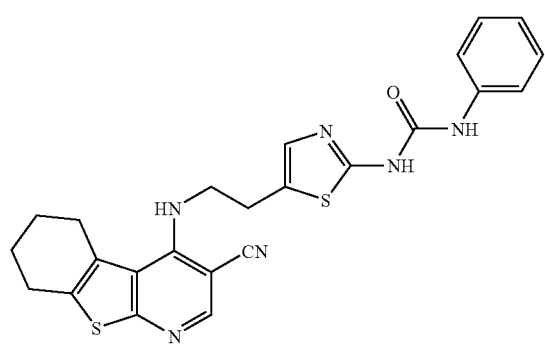

-continued
Compound 171
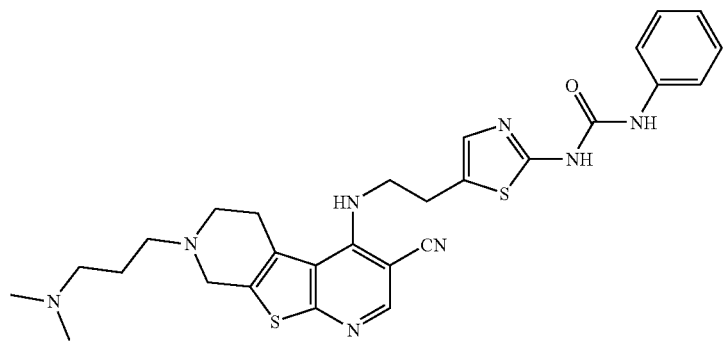
Compound 172
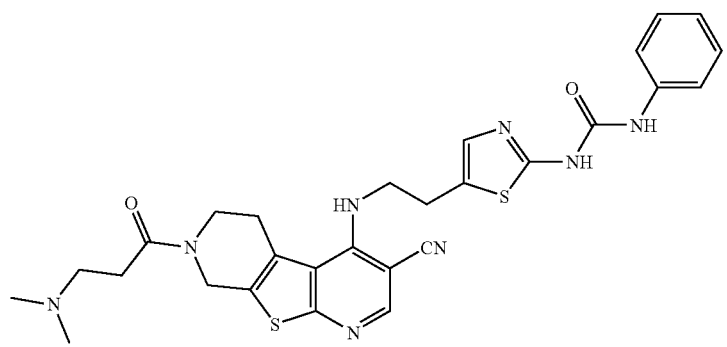
Compound 173
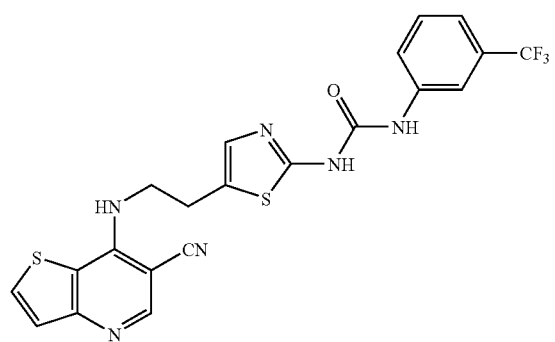
Compound 174
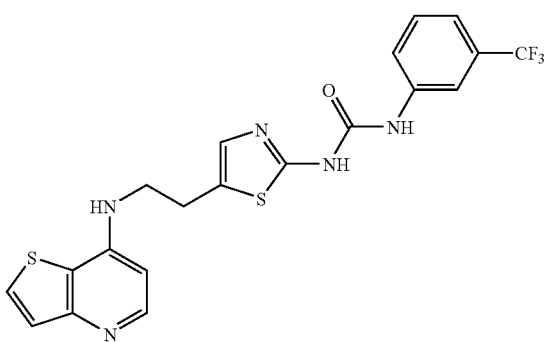
Compound 175
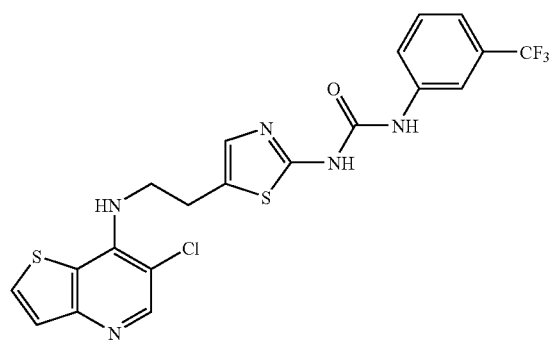
Compound 176
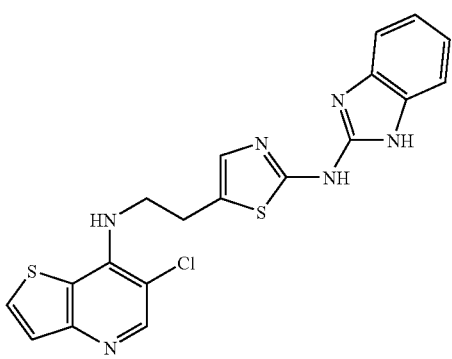

Compound 177
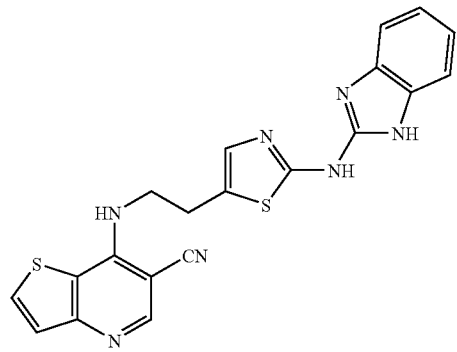
Compound 178
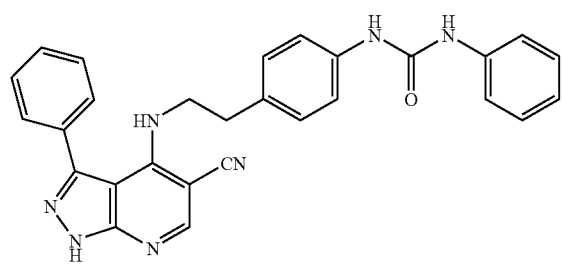
Compound 179
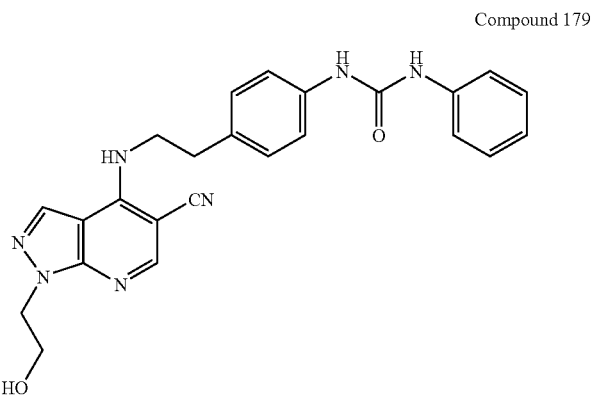
Compound 180
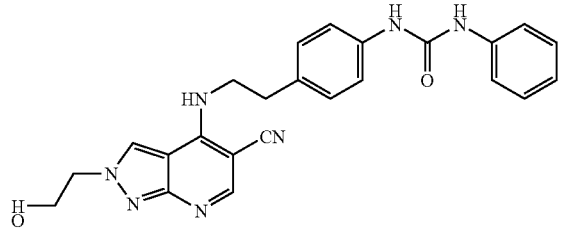
Compound 181
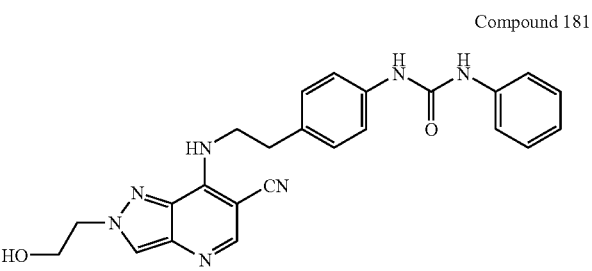
Compound 182
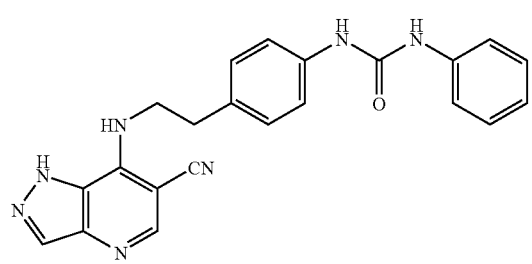
Compound 183
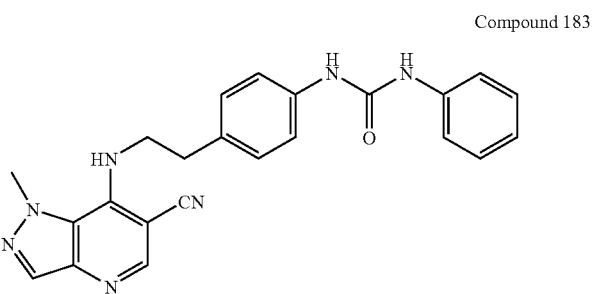
Compound 184
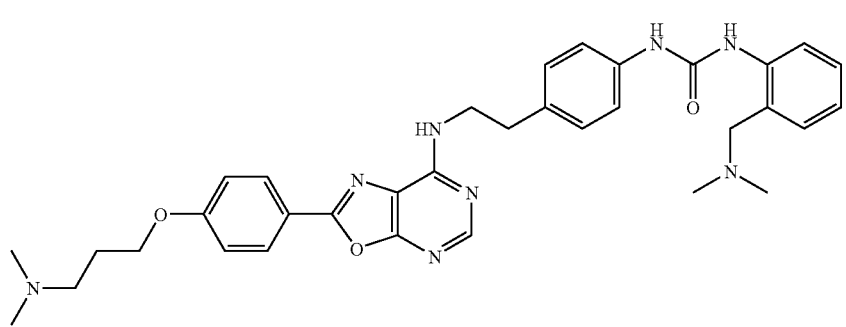

-continued
Compound 185
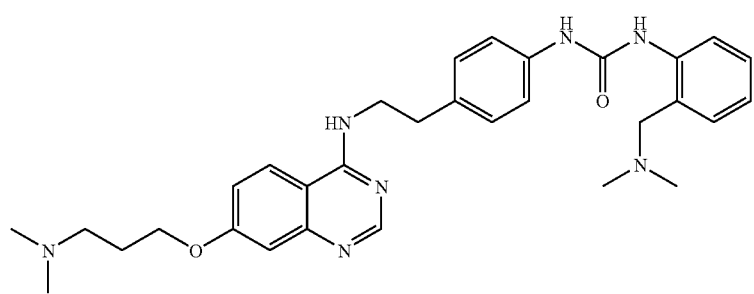
Compound 186
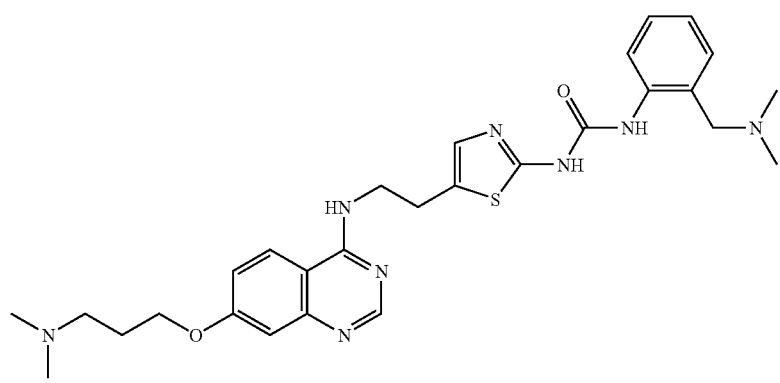
Compound 187
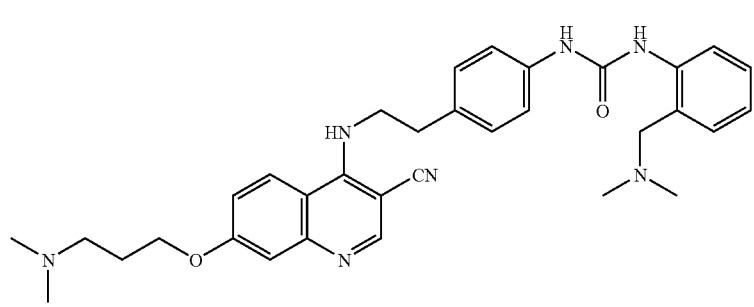
Compound 188
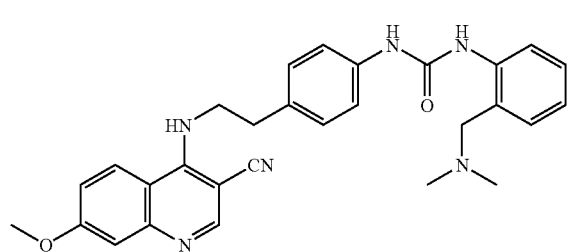
Compound 189
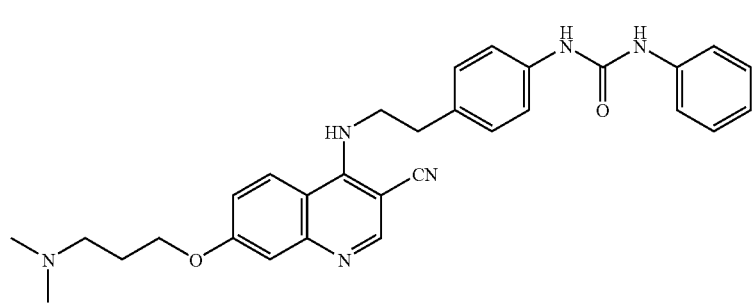

-continued
Compound 190
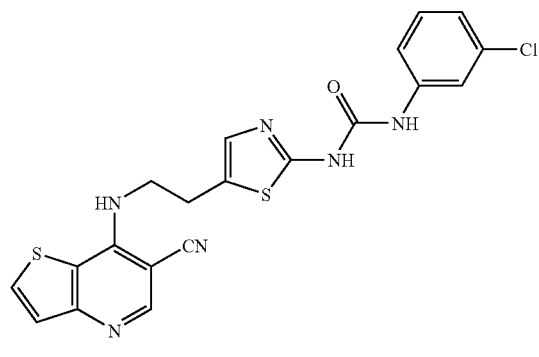
Compound 191
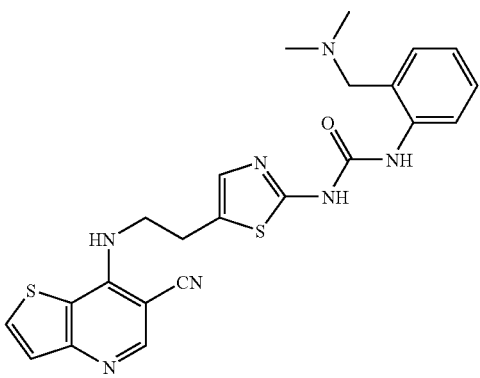
Compound 192
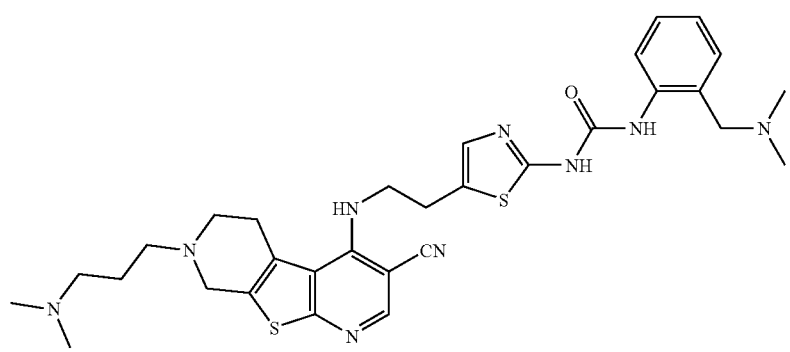
Compound 193
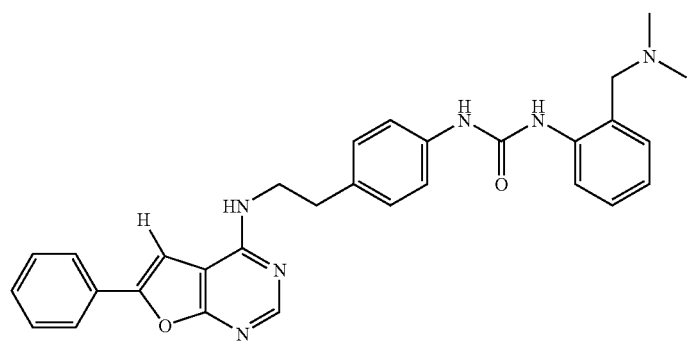
Compound 194
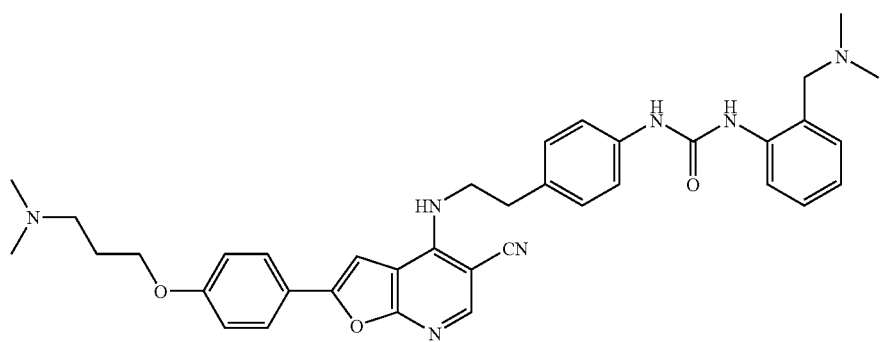

-continued
Compound 195
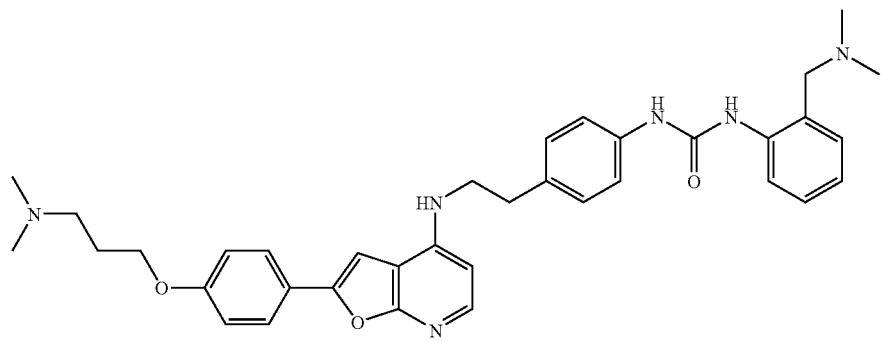
Compound 196
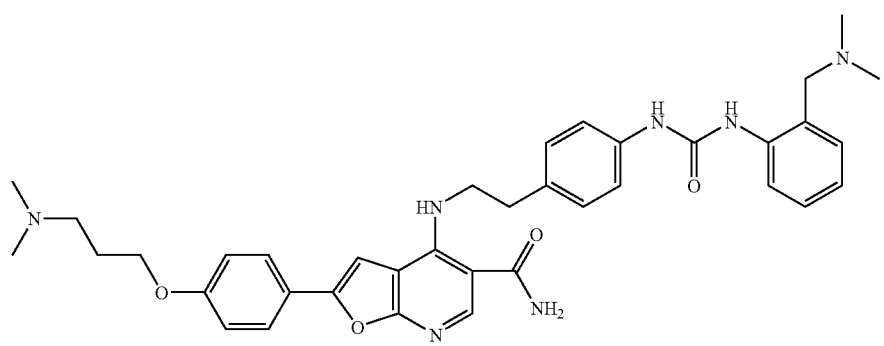
Compound 197
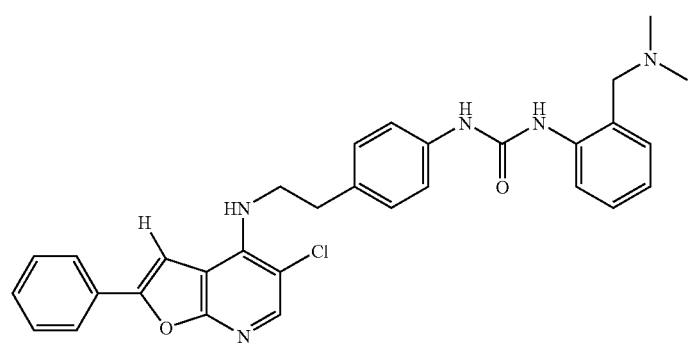
Compound 198
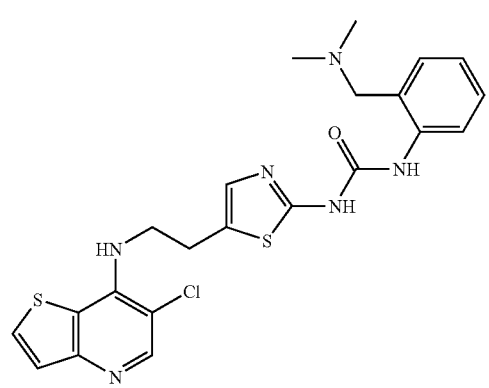
Compound 199
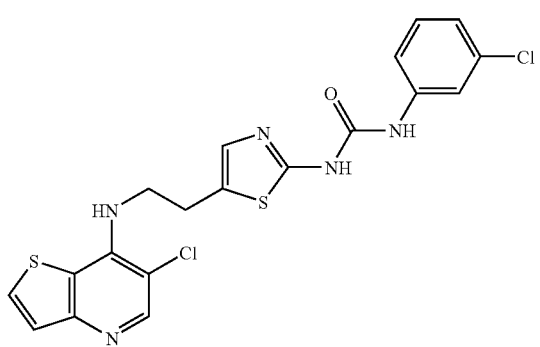

-continued
Compound 200
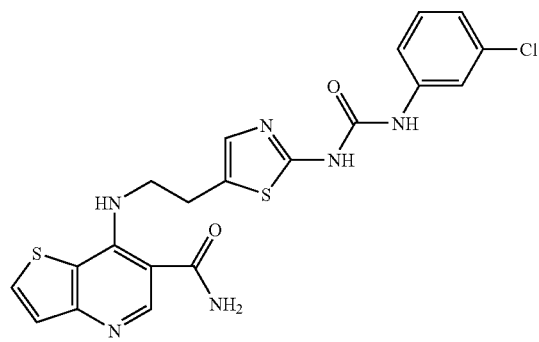
Compound 201
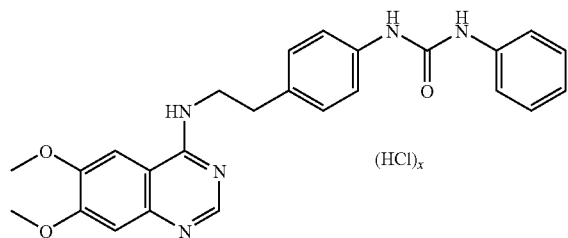
(HCl)x
Compound 202
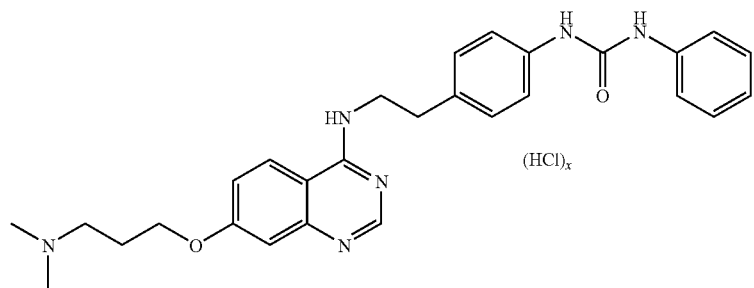
(HCl)x
Compound 203
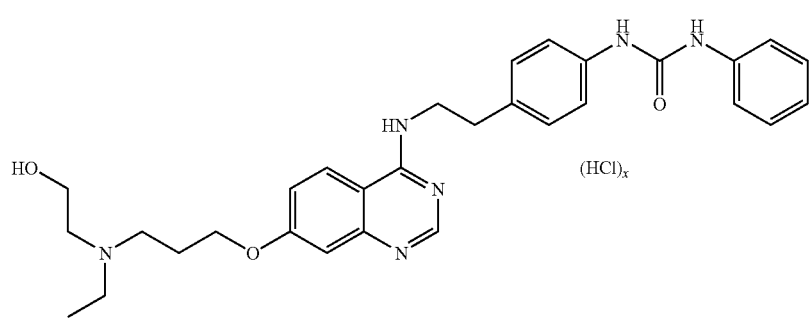
(HCl)x
Compound 204
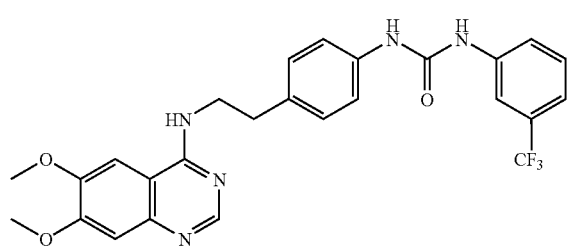
Compound 205
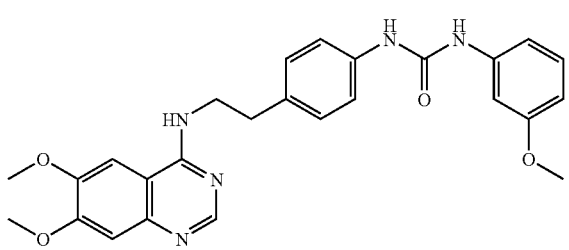

-continued
Compound 206
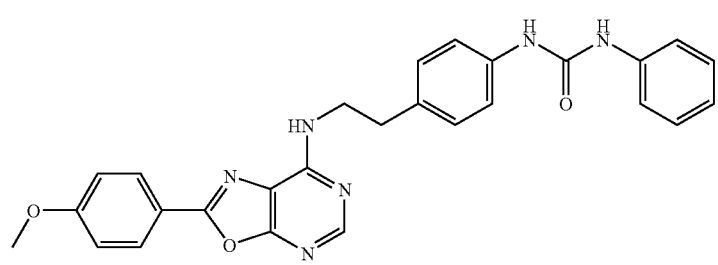
Compound 207
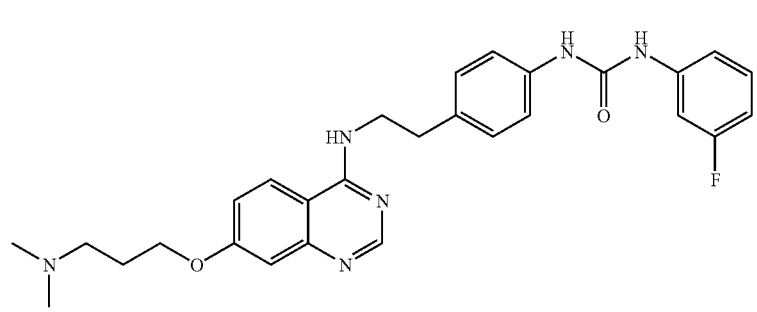
Compound 208
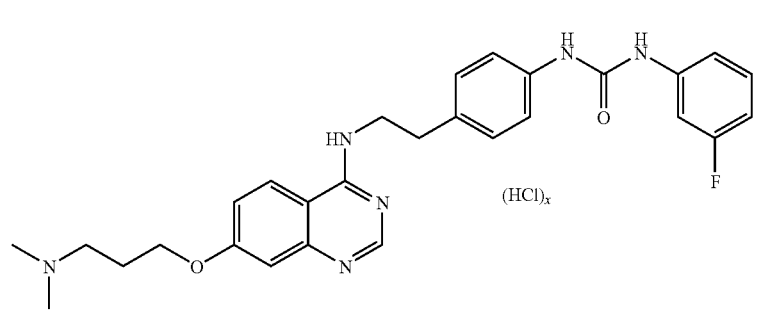
Compound 209
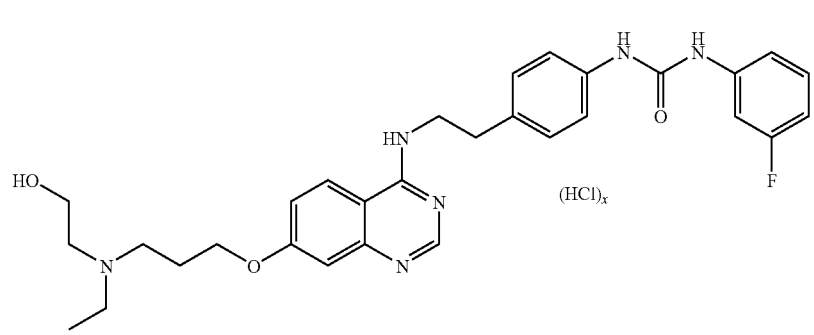
Compound 210
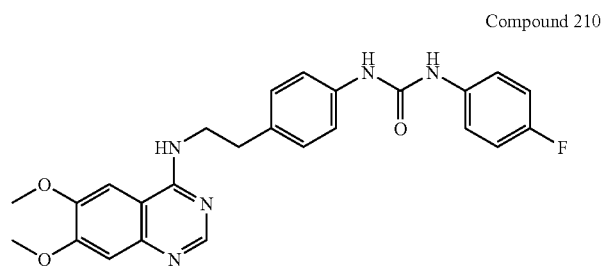
Compound 211
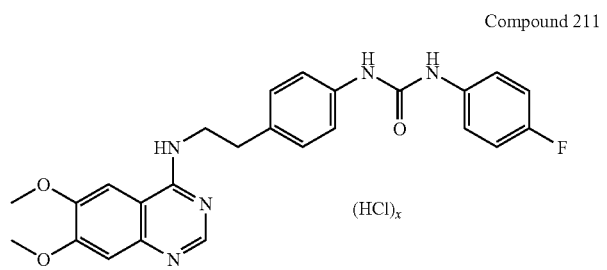

-continued
Compound 212
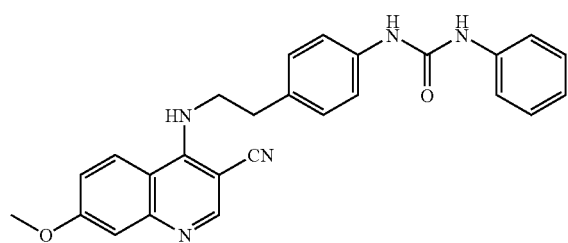
Compound 213
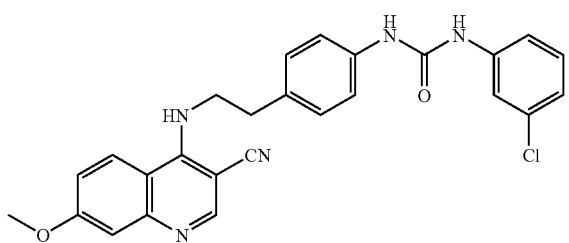
Compound 214
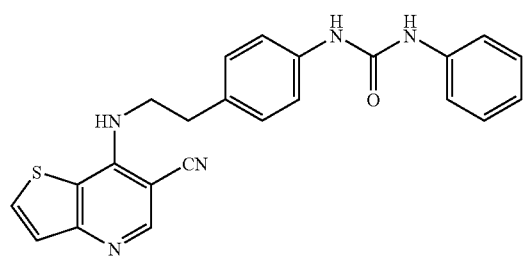
compound 215
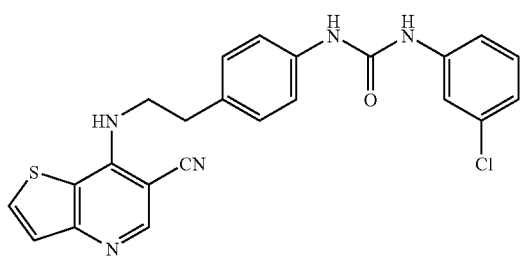
Compound 216
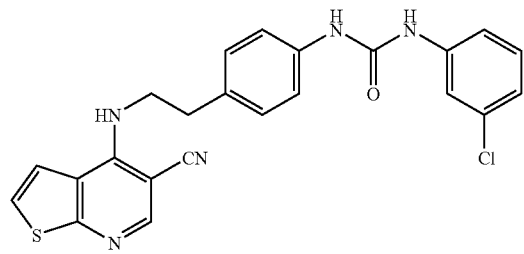
Compound 217
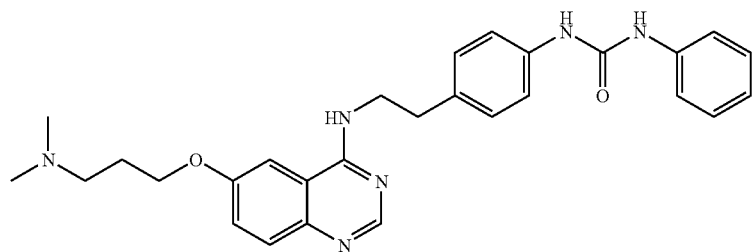
Compound 218
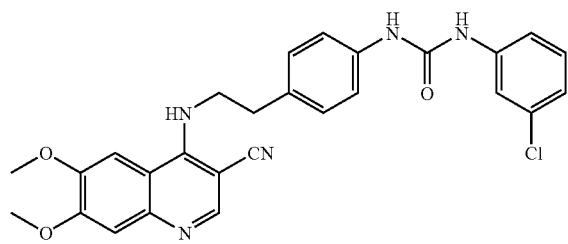
Compound 219
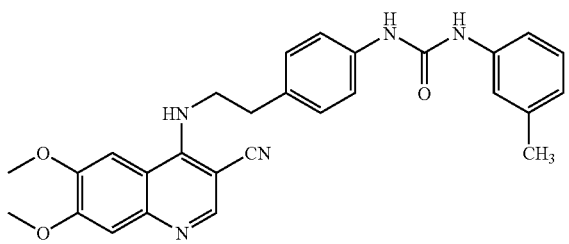
Compound 220
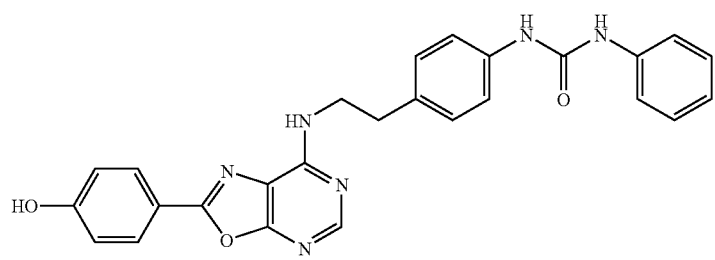

Compound 221
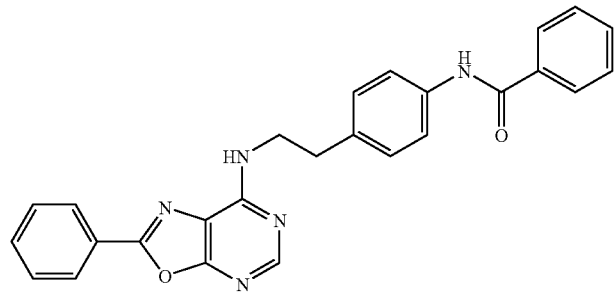
Compound 222
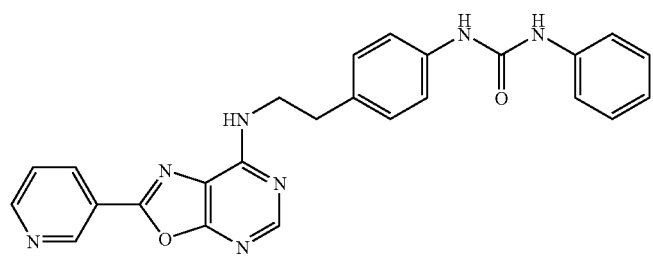
Compound 223
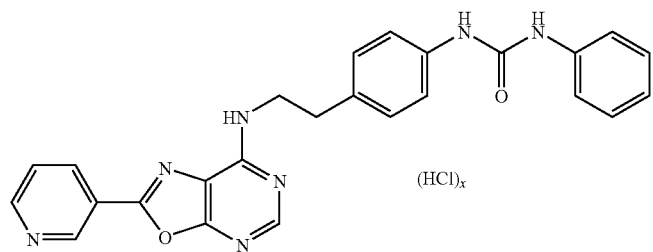
(HCl)x
Compound 224
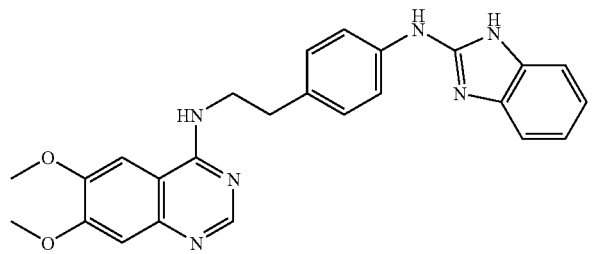
Compound 225
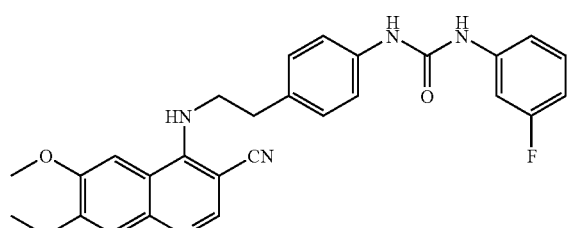
Compound 226
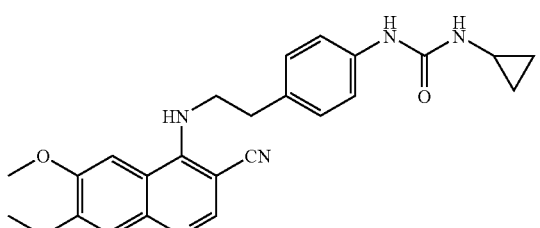
Compound 227
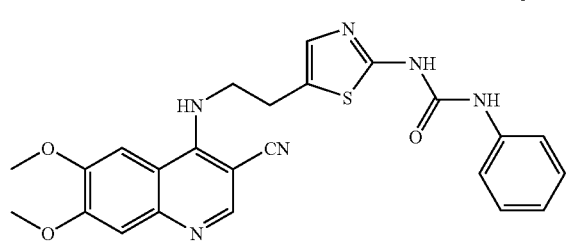
Compound 228
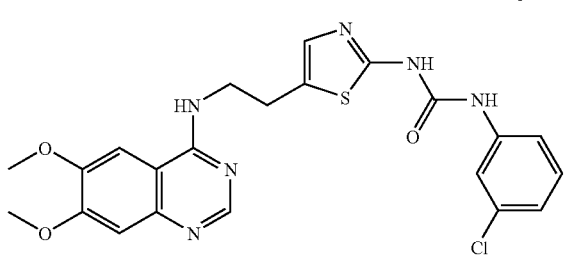

-continued
Compound 229
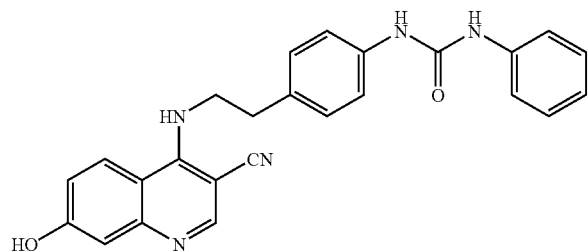
Compound 230
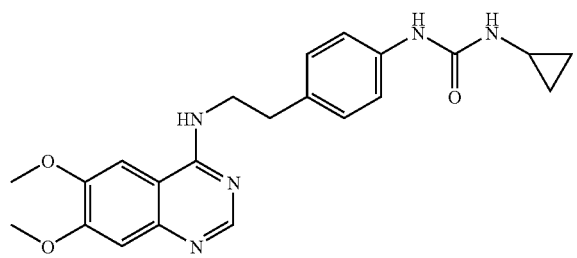
Compound 231
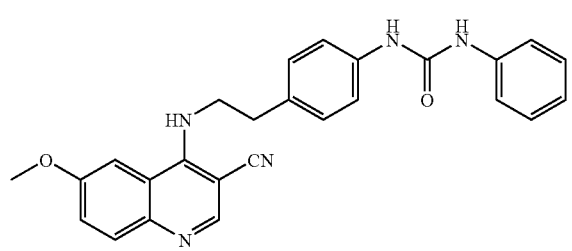
Compound 232
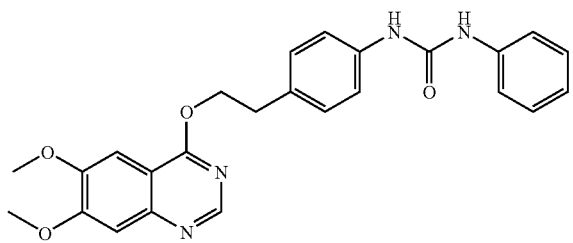
Compound 233
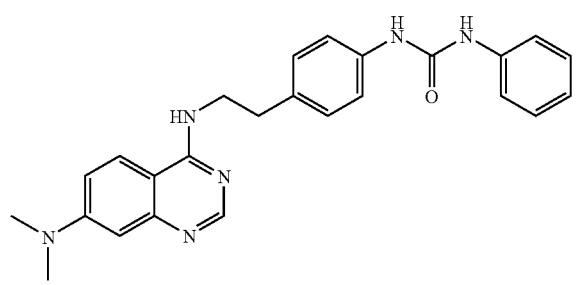
Compound 234
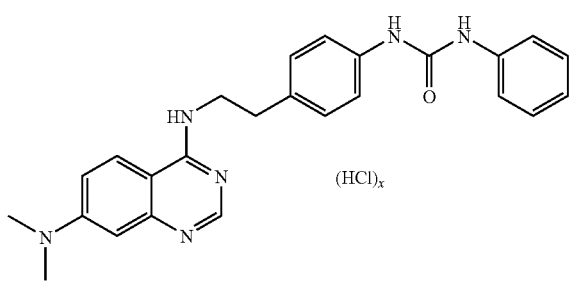
(HCl)$_x$
Compound 235
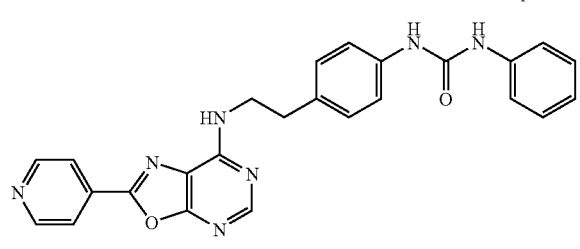
Compound 236
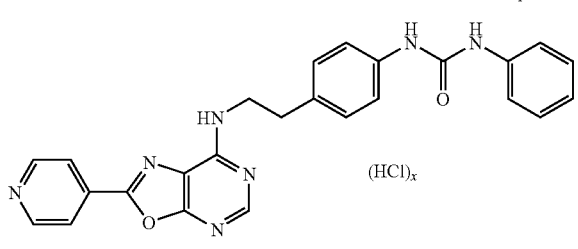
(HCl)$_x$
Compound 237
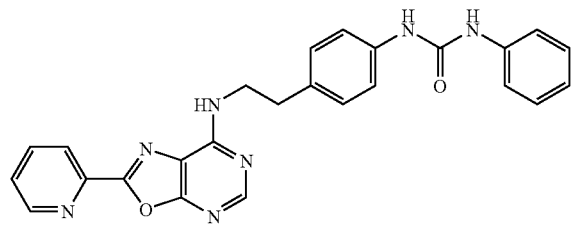
Compound 238
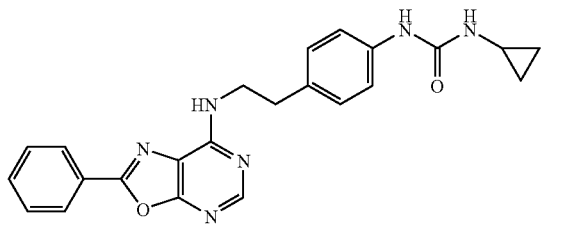

-continued
Compound 239
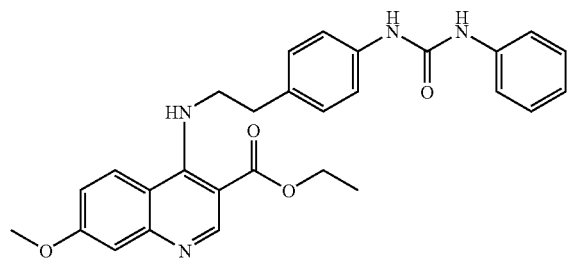
Compound 240
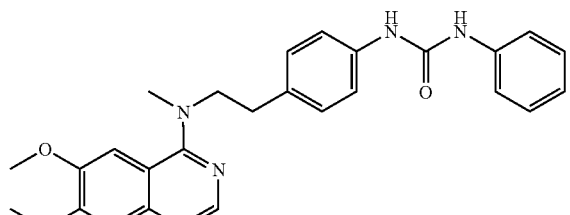
Compound 241
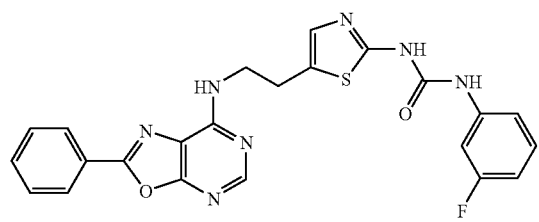
Compound 242
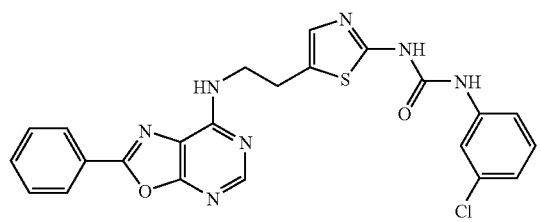
Compound 243
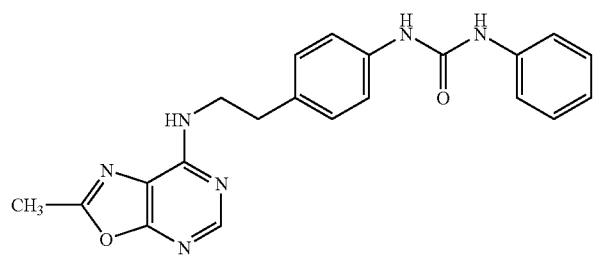
Compound 244
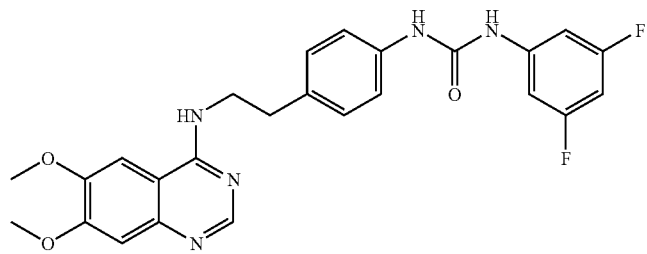
Compound 245
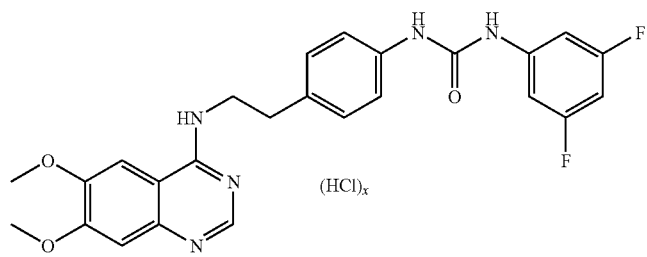
(HCl)$_x$
Compound 246
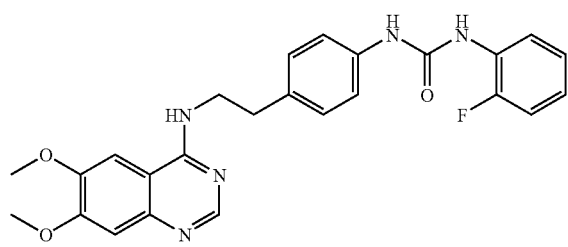

-continued
Compound 247
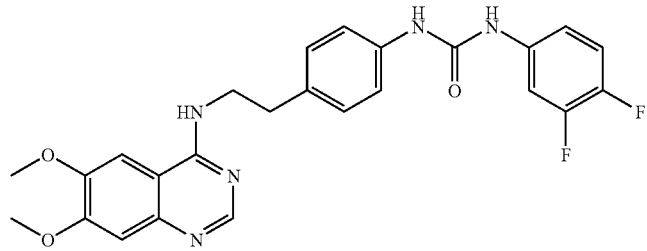
Compound 248
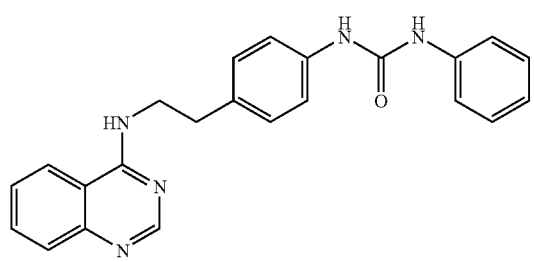
compound 249
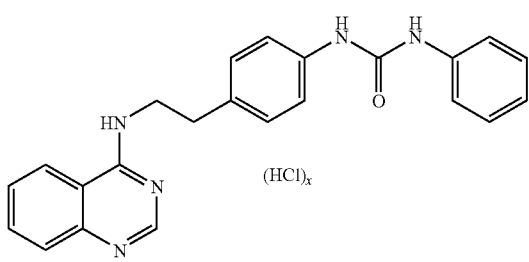
Compound 250
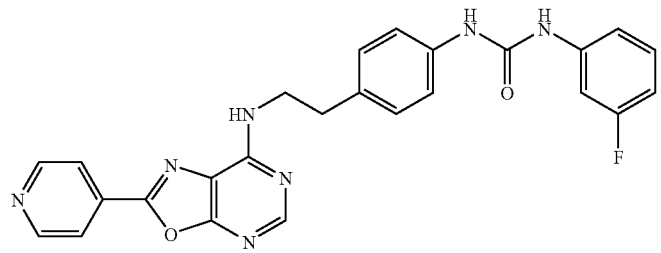
Compound 251
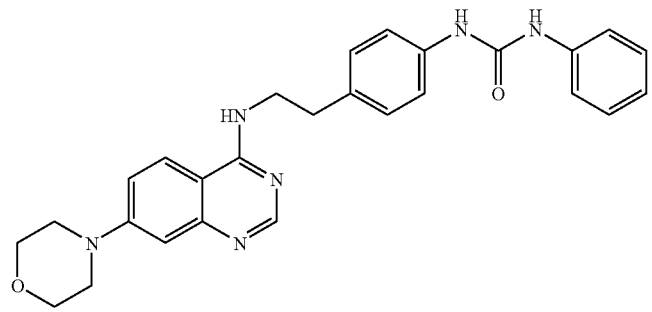
Compound 252
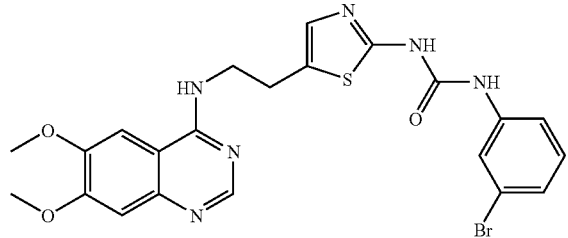
Compound 253
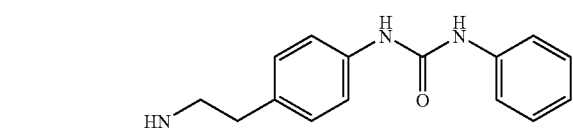
Compound 254

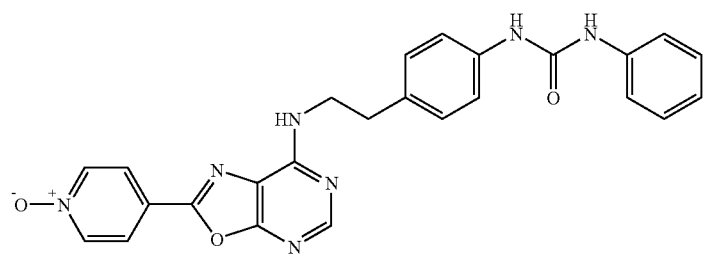

Compound 255

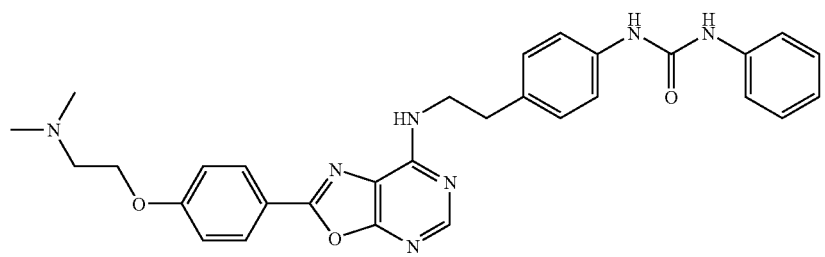

Compound 256

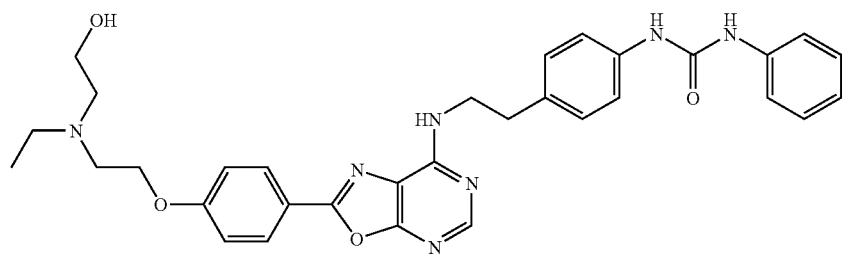

Compound 257

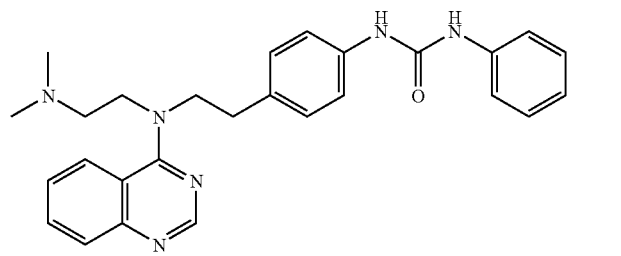

Compound 258

As shown above, certain fused multicyclic compounds of this invention are salts of hydrochloric acid, e.g., Compound 201, in which and similar HCl salts, x ranges from 0.1 to 3.0.

The fused multicyclic compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1 and 2 below show transformations for synthesizing compounds of this invention.

The route shown in Scheme 1 exemplifies synthesis of certain fused multicyclic compounds (VI) of the present invention. A mixture of chloro-substituted heterocycle (I) and amine (II) in ethanol is refluxed for 16 h to provide compound (III). Reaction of (III) with appropriately substituted isocyanate (IV) gives the desired compound (VI). Alternatively, reaction of amine (III) first with 1,1'-carbonyldiimidazole (CDI) in dichloromethane, followed by reaction with the appropriate amine or aniline forms the desired compound (VI). Pure compounds can be acquired after purification by silica gel column chromatography.

Scheme 1

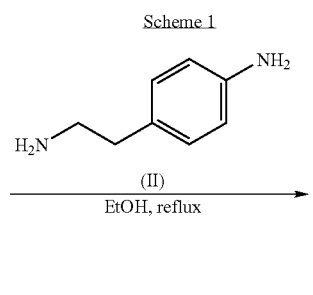

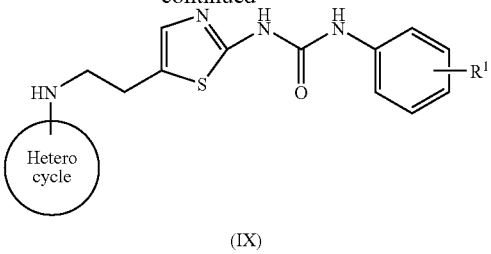

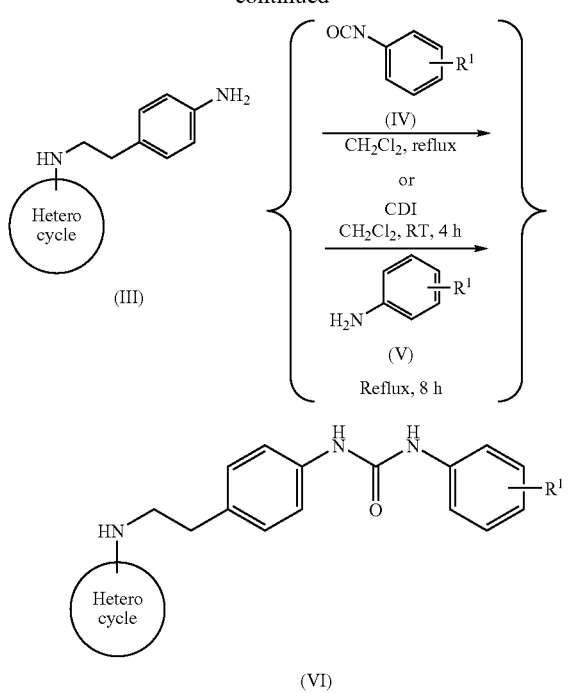

Scheme 2 below exemplifies a synthetic route of other fused multicyclic compounds (IX) of the present invention. Compounds (IX) can be prepared by using the appropriate amine (VII) and following a similar sequence of reactions as discussed above. The amine (VII) can be prepared by the method described in, e.g., Journal of Medicinal Chemistry, 1992, 35, 3239-3246.

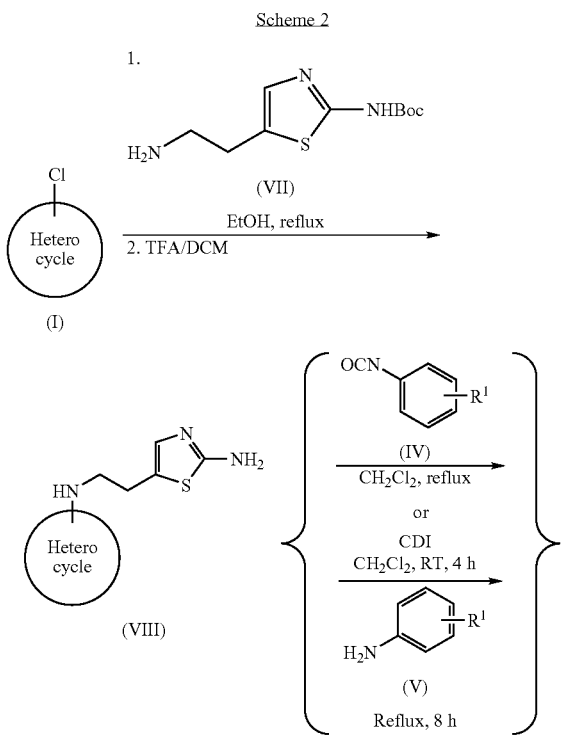

The fused multicyclic compounds of this invention can also be synthesized in manners similar to those outlined in Schemes 1 and 2 with necessary modifications as recognized by those skilled in the art.

A fused multicyclic compound thus synthesized can be further purified by flash column chromatography, high performance liquid chromatography, crystallization, or any other suitable methods.

Also within the scope of this invention are (1) a pharmaceutical composition that contains an effective amount of at least one of the fused multicyclic compounds of this invention and a pharmaceutically acceptable carrier, and (2) a method for treating a protein kinase (e.g., Aurora kinase) mediated disorder such as cancer by administering to a subject in need of this treatment an effective amount of such a fused multicyclic compound.

As used herein, the term "treating" refers to administering a fused multicyclic compound to a subject that has a protein kinase mediated disorder such as cancer, or has a symptom of or a predisposition toward it, with the purpose to prevent, cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

Deregulation of many of the protein kinases are implicated in a number of diseases. Thus targeted inhibition of protein kinases has become an attractive therapeutic strategy for treating various protein kinase mediated disorders. Protein kinases that can be inhibited by the compounds of the invention include but are not limited to AURORA, BCR-ABL, VEGFR, PDGFR, EGFR, FLT3, JAK2, C-ABL, PDK1, CDK, CHK1, LCK, FGFR, C-KIT, C-MET, EPH, SRC, MEK1, cRAF, AKT, PI3K, MTOR, PLK, RET, TIE2, AXL, IKK, PIM, ROCK kinase, AKT1 (PKB alpha), ALK, AMPK A1/B1/G1, CDC42 BPA (MRCKA), CDK2/cyclin A, CHEK1, ERBB2 (HER2), FRAP1 (mTOR), IGF1R, IKBKE (IKK epsilon), MAP2K1 (MEK1), CHEK2, MST1R(RON), NTRK1(TRKA), and RPS6 KB1 (p70S6K). Other target protein kinases are described by, e.g., Manning et al., Science 2002, 298, 1912 and Noble et al., Science 2004, 303, 1800. Diseases that are associated with protein kinases and can be treated by the methods of the invention include but are not limited to cancer, diabetes, inflammation, allergy/asthma, immune diseases, central nervous system diseases, and angiogenesis disorders.

Cancer that can be treated by the methods of the invention include both solid and haematological tumours of various organs. Examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. Other cancer types, in which Aurora kinase activity is upregulated/dysregulated, are described in WO 2006/003440 A1, WO 2004/058781, US Patent Publication 2007/0149561, EP 1771450, and Cancer treatment reviews 34, 175-182 (2008).

The compounds of this invention can be administered in conjunction with a therapeutic agent selected from the group consisting of cytotoxic agents, radiotherapy, and immunotherapy. Non-limiting examples of cytotoxic agents suitable for use in combination with the protein kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide and related analogs, including, e.g., CC-5013 and CC-4047; protein tyrosine kinase inhibitors, including, e.g., imatinib mesylate and gefitinib; antibodies, including, e.g., trastuzumab, rituximab, cetuximab, and bevacizumab; mitoxantrone; dexamethasone; prednisone; and temozolomide.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A fused multicyclic compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the fused multicyclic compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the fused multicyclic compounds of this invention in inhibiting activity of protein kinase (e.g., Aurora kinase). The compounds can further be examined for their efficacy in treating cancer in vitro and/or in vivo. For example, a compound can be tested for its efficacy in inhibiting cancer cell growth (e.g., a growth inhibition assay of HCT-116 colon carcinoma cell line) or it can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Example 1

Synthesis of 1-(4-(2-(6,7-dimethoxyquinazolin-4-ylamino)ethyl)phenyl)-3-phenylurea (Compound 1)

[2-(4-Amino-phenyl)-ethyl]-(6,7-dimethoxy-quinazolin-4-yl)-amine

A solution of 4-chloro-6,7-dimethoxy-quinazoline (2 g, 8.92 mmol) and 4-(2-amino-ethyl)-phenyl amine (1.3 g, 9.82 mmol) in 1-butanol (20 mL) was heated at 80° C. overnight. After the solution was cooled to room temperature, the solvent was removed and the residue was purified by silica gel column chromatography (eluted by 5% methanol in $CH_2Cl_2$) to get the title compound (2.3 g, 68%). $^1$H-NMR (300 MHz $CDCl_3$) δ 8.57 (s, 1H), 7.19 (s, 1H), 7.48 (d, 2H, J=8.1 Hz), 6.66 (d, 3H, J=7.8 Hz), 5.36 (t, 1H, NH), 4.00 (s, 3H), 3.93 (s, 1H), 3.85 (q, 2H, J=6.6 Hz), 3.62 (s, 1H), 2.92 (t, 2H, J=6.6 Hz).

1-{4-[2-(6,7-Dimethoxy-quinazolin-4-ylamino)-ethyl]-phenyl}-3-phenyl-urea (Compound 1)

Phenyl isocyante (550 mg, 4.62 mmol) was added slowly dropwise to a solution of [2-(4-amino-phenyl)-ethyl]-(6,7-dimethoxy-quinazolin-4-yl)-amine (1 g, 3.08 mmol) $CH_2Cl_2$ (20 mL). The reaction mixture was stirred overnight at room temperature. The precipitated product was filtered and washed thoroughly with dichloromethane to provide compound 1 (1.1 g, 85%). $^1$H-NMR (300 MHz DMSO-$d_6$) δ 8.63 (s, 1H), 8.60 (s, 1H), 8.34 (s, 1H), 8.01 (t, 2H, J=5.7 Hz), 7.56 (s, 1H), 7.43-7.35 (m, 4H), 7.25 (t, 2H, J=7.5 Hz), 7.16 (d, 2H, J=8.4 Hz), 7.06 (s, 1H), 6.93 (t, 1H, J=7.5 Hz), 3.87 (s, 3H), 3.86 (s, 1H), 3.68 (q, 2H, J=8 Hz), 2.88 (t, 2H, J=8 Hz). LC-MS (ESI) m/z: 444.0 (M+1).

Example 2

Synthesis of 1-{4-[2-(6,7-Dimethoxy-quinazolin-4-ylamino)-ethyl]-phenyl}-3-pyridin-3-yl-urea (Compound 2)

1,1'-Carbonyldiimidazole (CDI) (0.46 mmol) was added to a solution of [2-(4-amino-phenyl)-ethyl]-(6,7-dimethoxy-quinazolin-4-yl)-amine (50 mg, 0.15 mmol) in THF (5 mL). The mixture was stirred for 6 h at room temperature. Pyridin-3-ylamine (0.46 mmol) was then added and then the reaction mixture was refluxed overnight. After the solvent was removed, the residue was partitioned between water and EtOAc. The organic layer was separated, washed with brine, and concentrated. The residue was purified by silica gel column chromatography to provide pure compound 2. $^1$H-NMR (300 MHz DMSO-$d_6$) δ 8.85 (s, 1H), 8.78 (s, 1H), 8.57 (d, 1H, J=2.1 Hz), 8.35 (s, 1H), 8.16 (dd, 1H, J=1.5 Hz, 4.5 Hz), 8.00 (t, 1H, J=5.4 Hz), 7.93-7.89 (m, 1H), 7.56 (s, 1H), 7.38 (d, 2H, J=8.4 Hz), 7.30-7.20 (m, 1H), 7.17 (d, 2H), 7.06 (s, 1H), 3.87 (s, 3H), 3.86 (s, 3H), 3.69 (q, 2H), 2.88 (t, 2H, J=8.4 Hz). LC-MS (ESI) m/z: 445.0 (M+1).

Example 3

Synthesis of 1-{4-[2-(6,7-Dimethoxy-quinazolin-4-ylamino)-ethyl]-phenyl}-3-(2-dimethylaminomethyl-phenyl)-urea (Compound 3)

Compound 3 was prepared in a manner similar to that described in Example 2.

$^1$H-NMR (300 MHz $CDCl_3$) δ 9.89 (s, 1H), 8.58 (s, 1H), 7.99 (d, 1H, J=6.3 Hz), 7.55 (s, 1H), 7.52-7.26 (m, 2H), 7.25-7.18 (m, 2H), 7.09 (s, 1H), 7.053 (d, 1H, J=5.4 Hz), 6.96 (t, 1H), 6.59 (s, 1H), 6.57 (s, 1H), 5.85 (s, 1H), 3.99 (s, 3H), 3.90 (s, 3H), 3.87 (q, 2H, J=5.0 Hz), 3.49 (s, 2H), 3.02 (t, 2H, J=5.1 Hz), 2.06 (s, 6H). LC-MS (ESI) m/z: 501.0 (M+1).

Example 4

Synthesis of 1-(4-{2-[7-(3-Dimethylamino-propoxy)-quinazolin-4-ylamino]-ethyl}-phenyl)-3-phenyl-urea (Compound 4)

[2-(4-Amino-phenyl)-ethyl]-[7-(3-chloro-propoxy)-quinazolin-4-yl]-amine

A solution of 4-chloro-7-(3-chloro-propoxy)-quinazoline (synthesized as reported in *J. Med. Chem.* 2007, 50, 2213-2224) (100 mg, 0.389 mmol), 2-(4-aminophenyl)ethyl amine (63.6 mg, 0.467 mmol) and triethylamine (118.1 mg, 1.167 mmol) in ethanol (3 mL) was heated at 120° C. for 3 hours. The solution was cooled and the solid formed was filtered, washed with ethanol and then with dichloromethane to give the title compound as light yellow solid product (34 mg, 25%). $^1$H-NMR (300 MHz, $CD_3OD$): 7.93-8.37 (s, 1H), 7.96 (d, J=9.0 Hz, 1H), 7.07-7.13 (m, 2H), 7.00-7.03 (d, J=8.1 Hz, 2H), 6.66-6.69 (d, J=8.4 Hz, 2H), 4.24-4.28 (t, 2H), 3.71-3.81 (m, 4H), 2.84-2.89 (t, 2H), 2.27-2.31 (m, 2H). LC-MS (ESI) m/z 357.3 (M+1).

1-(4-{2-[7-(3-Chloro-propoxy)-quinazolin-4-ylamino]-ethyl}-phenyl)-3-phenyl-urea (Compound 6)

A solution of [2-(4-amino-phenyl)-ethyl]-[7-(3-chloro-propoxy)-quinazolin-4-yl]-amine (34 mg, 0.095 mmol) and phenyl isocyanate (17.0 mg, 0.143 mmol) in methylene chloride (8 mL) was stirred under nitrogen at room temperature overnight. The solid product formed was filtered to give the title compound as a solid (42 mg, 93%). $^1$H-NMR (300 MHz, $d_6$-DMSO): δ 8.66 (s, 1H), 8.63 (s, 1H), 8.42 (s, 1H), 8.20 (t, 1H), 8.13 (d, J=9.0 Hz, 1H), 7.42-7.46 (m, 2H), 7.37 (d, J=8.4 Hz, 2H), 7.24-7.29 (m, 2H), 7.08-7.18 (m, 4H), 6.96 (t, 1H), 4.23 (t, 2H), 3.83 (t, 2H), 3.70 (q, 2H), 2.89 (t, 2H), 2.18-2.27 (m, 2H). LC-MS (ESI) m/z: 476.4 (M+1).

1-(4-{2-[7-(3-Dimethylamino-propoxy)-quinazolin-4-ylamino]-ethyl}-phenyl)-3-phenyl-urea (Compound 4)

A solution of 1-(4-{2-[7-(3-chloro-propoxy)-quinazolin-4-ylamino]-ethyl}-phenyl)-3-phenyl-urea (20 mg, 0.042 mmol) and dimethylamine (94.7 mg, 0.840 mmol) in DMF (1 mL) was heated at 150° C. in CEM microwave for 10 min. The reaction mixture was purified using silica gel preparative thin layer chromatography to provide the title compound (10 mg, 49%). $^1$H-NMR (400 MHz, DMSO-$d_6$): δ 8.69 (s, 1H), 8.66 (s, 1H), 8.41 (s, 1H), 8.19 (t, 1H, NH), 8.10-8.12 (m, 1H), 7.43-7.45 (m, 2H), 7.36-7.38 (m, 2H), 7.26 (t, 2H), 7.17 (d, J=8.8 Hz, 2H), 7.08-7.11 (m, 1H), 7.05 (d, J=2.4 Hz, 1H), 6.95 (t, 1H), 4.13 (t, 2H), 3.69 (q, 2H), 2.89 (t, 2H), 2.44 (t, 2H), 2.20 (s, 6H), 1.89-1.93 (m, 2H). LC-MS (ESI) m/z 485.3 (M+1).

Example 5

Synthesis of 1-{4-[2-(6,7-Dimethoxy-quinazolin-4-ylamino)-ethyl]-phenyl}-3-(3-fluoro-phenyl)-urea (Compound 5)

Compound 5 was prepared in a manner similar to that described in Example 2.

¹H-NMR (DMSO d₆) δ 8.56 (s, 1H), 7.80 (s, 1H), 7.67 (s, 1H), 7.48 (s, 1H), 7.33-7.27 (m, 1H), 7.25-7.24 (m, 4H), 7.18-7.17 (m, 2H), 6.95 (s, 1H), 6.72 (t, 1H), 5.99 (t, 1H), 3.95 (s, 1H), 3.88 (s, 1H), 3.79 (q, 2H, J=4.5 Hz), 2.96 (t, 3H, J=5.1 Hz). LC-MS (ESI) m/z: 462.0 (M+1).

Example 6

Synthesis of 1-(4-{2-[7-(3-Chloro-propoxy)-quinazolin-4-ylamino]-ethyl}-phenyl)-3-phenyl-urea (Compound 6)

Compound 6 was prepared in a manner described in Example 4.
¹H-NMR (300 MHz, d₆-DMSO): δ 8.66 (s, 1H), 8.63 (s, 1H), 8.42 (s, 1H), 8.20 (t, 1H), 8.13 (d, J=9.0 Hz, 1H), 7.42-7.46 (m, 2H), 7.37 (d, J=8.4 Hz, 2H), 7.24-7.29 (m, 2H), 7.08-7.18 (m, 4H), 6.96 (t, 1H), 4.23 (t, 2H), 3.83 (t, 2H), 3.70 (q, 2H), 2.89 (t, 2H), 2.18-2.27 (m, 2H). LC-MS (ESI) m/z: 476.4 (M+1).

Example 7

Synthesis of 1-Phenyl-3-{4-[2-(2-phenyl-oxazolo[5,4-d]pyrimidin-7-ylamino)-ethyl]-phenyl}-urea (Compound 7)

2-Phenyl-oxazolo[5,4-d]pyrimidin-7-ol

A mixture of benzoic anhydride (1.33 g, 5.9 mmol) and 4,6-dihydroxy-5-aminopyrimidine (0.5 g, 3.93 mmol) was heated at 140° C. under nitrogen for 5 hours. The reaction mixture was purified by silica gel column chromatography (EtOAc:hexanes=1:2, and then CH₂Cl₂:MeOH=9:1) to afford the title compound as a white solid (0.19 g, 22%): LC-MS (ESI) m/z 214.0 (M+1).

7-Chloro-2-phenyl-oxazolo[5,4-d]pyrimidine

2-Phenyl-oxazolo[5,4-d]pyrimidin-7-ol (0.10 g, 0.43 mmol) was dissolved in 3 mL POCl₃, and the mixture was refluxed under nitrogen for 6 hours. The reaction mixture was cooled to room temperature and poured onto ice water. The resulting mixture was extracted by CH₂Cl₂. The combined organic layers were concentrated and the residue was purified by column chromatography (EtOAc:hexanes=1:10) to afford the title compound as a white solid (73 mg, 67%). ¹H NMR 400 MHz (CDCl₃) δ 8.82 (s, 1H), 7.35-7.32 (m, 2H), 7.68-7.57 (m, 3H). LC-MS (ESI) m/z 232.0 (M+1).

1-Phenyl-3-{4-[2-(2-phenyl-oxazolo[5,4-d]pyrimidin-7-ylamino)-ethyl]-phenyl}-urea (Compound 7): A solution of 7-Chloro-2-phenyl-oxazolo[5,4-d]pyrimidine (60 mg, 0.26 mmol), 2-(4-aminophenyl)ethylamine (71 mg, 0.52 mmol) and triethylamine (0.11 mL, 0.78 mmol) in 3 mL EtOH was refluxed for 9 hours. After removal of EtOH, the residue was passed through a short silica column using CH₂Cl₂:MeOH=20:1 as eluent to remove unreacted 2-(4-aminophenyl)ethylamine. The intermediate obtained was reacted with phenylisocyanate (0.033 mL, 0.52 mmol) in CH₂Cl₂ under ambient temperature for 12 hours. Precipitate formed was filtered, washed with CH₂Cl₂ to provide compound 7 as a white solid (110 mg, 94% from two steps). ¹H NMR 400 MHz (CDCl₃) δ 8.60 (s, 1H), 8.57 (s, 1H), 8.38 (brs, 1H), 8.34 (s, 1H), 7.71-7.58 (m, 3H), 7.42 (d, J=8.0 Hz, 2H), 7.36 (d, J=8.0 Hz, 2H), 7.26 (d, J=8.0 Hz, 2H), 7.24 (d, J=8.0 Hz, 2H), 7.17 (d, J=8.0 Hz, 2H), 6.94 (t, J=8.0 Hz, 2H), 3.71 (td, J=7.2, 7.2 Hz, 2H), 2.88 (t, J=7.2 Hz, 2H). LC-MS (ESI) m/z 451.0 (M+H).

Example 8

Synthesis of 1-(3-chlorophenyl)-3-(5-(2-(6-cyanothieno[3,2-b]pyridin-7-ylamino)ethyl)thiazol-2-yl)urea (Compound 190)

3-(Dimethylamino-methyleneamino)-thiophene-2-carboxylic acid methyl ester

A mixture of methyl 3-amino-2-thiophenecarboxylate (1.572 g, 10 mmol) in 5 ml of N,N-dimethylformamide dimethyl acetal (DMF-DMA) was heated at reflux for 2 h and then allowed to cool to room temperature. The resulting mixture was evaporated to give 2.019 g (95%) of orange residue.
¹H NMR (400 MHz, DMSO-d₆) δ 7.75 (s, 1H), 7.63 (d, J=5.6 Hz, 1H), 6.81 (d, J=5.2 Hz, 1H), 3.67 (m, 3H), 3.00 (s, 3H), 2.93 (s, 3H); LC-MS (ESI) m/z 213.1 (M+1).

7-Oxo-4,7-dihydro-thieno[3,2-b]pyridine-6-carbonitrile

A solution of 1.04 ml (20 mmol) of acetonitrile in 7 ml of tetrahydrofuran was added to a solution of 12.5 ml of 1.6 M n-butyl lithium in hexane (20 mmol) in 25 ml of tetrahydrofuran at −78° C. After 15 minutes, a solution of 2.019 g (9.5 mmol) of 3-(dimethylamino-methyleneamino)-thiophene-2-carboxylic acid methyl ester in 25 ml of tetrahydrofuran was added dropwise over 1 h. The reaction mixture was stirred at −78° C. for 30 minutes, and then allowed to warm to room temperature. After stirring at room temperature for 1 h, the reaction mixture was cooled to −50° C. and 1.4 ml of acetic acid was added. The resulting mixture was partitioned between ethyl acetate and water. The organic layer was dried over Na₂SO₄, filtered, and concentrated under reduced pressure. The residue was recrystallized from acetone and hexanes to give 0.668 g (40%) of red-brown solid. ¹H NMR (300 MHz, DMSO-d₆) δ 8.38 (s, 1H), 7.94 (d, J=5.4 Hz, 1H), 7.25 (d, J=6 Hz, 1H); LC-MS (ESI) m/z 177.0 (M+1).

7-Chloro-thieno[3,2-b]pyridine-6-carbonitrile

A stirred mixture of 7-oxo-4,7-dihydro-thieno[3,2-b]pyridine-6-carbonitrile (0.668 g, 3.8 mmol) and 6 ml of phosphorus oxychloride was heated to reflux for 2 h, and then cooled to room temperature. The residue was added to ice water and dichloromethane, and the resulting mixture was neutralized by addition of solid NaHCO₃ carefully. The organic layer was separated, washed with H₂O, dried over MgSO₄, and concentrated in vacuum to give 0.526 g (71%) of a red-brown solid. ¹H NMR (300 MHz, DMSO-d₆) δ 9.12 (s, 1H), 8.60 (d, J=5.4 Hz, 1H), 7.82 (d, J=6 Hz, 1H); LC-MS (ESI) m/z 195.0 (M+1).

{5-[2-(6-Cyano-thieno[3,2-b]pyridin-7-ylamino)-ethyl]-thiazol-2-yl}-carbamic acid tert-butyl ester A stirred mixture of 7-chloro-thieno[3,2-b]pyridine-6-carbonitrile (47.8 mg, 0.25 mmol), [5-(2-amino-ethyl)-thiazol-2-yl]-carbamic acid tert-butyl ester (J Med Chem, 1992, 35, 3239-3246) (54.6 mg, 0.22 mmol), and triethylamine (0.04 ml, 0.28 mmol) in 3 ml of ethanol was heated to reflux for 17 hr. Ethanol was evaporated, and the residue was partitioned between dichloromethane and aqueous NaHCO₃. The organic layer was washed with H₂O, dried over MgSO₄, filtered, and concentrated in vacuum. The resulting residue was purified by silica gel chromatography (MeOH/CH₂Cl₂/NH₃=1/20/0.1) to give 36.1 mg (40%) of yellow solid. $^1$H NMR (300 MHz, CDCl₃) δ 8.49 (s, 1H), 7.82 (d, J=5.4 Hz, 1H), 7.52 (d, J=5.4 Hz, 1H), 7.18 (s, 1H), 5.32 (m, 1H), 4.08 (q, J=7.2 Hz, 2H), 3.20 (t, J=7.2 Hz, 2H), 1.55 (s, 9H); LC-MS (ESI) m/z 402.1 (M+1).

7-[2-(2-Amino-thiazol-5-yl)-ethylamino]-thieno[3,2-b]pyridine-6-carbonitrile

A mixture of {5-[2-(6-cyano-thieno[3,2-b]pyridin-7-ylamino)-ethyl]-thiazol-2-yl}-carbamic acid tert-butyl ester (36.1 mg, 0.09 mmol) and trifluoroacetic acid (1 ml) in 4 ml of dichloromethane was stirred at room temperature for 16 hr. Dichloromethane was evaporated, and the residue obtained was dissolved in ethyl acetate, washed with aqueous sodium bicarbonate solution, dried over MgSO₄, filtered, and concentrated in vacuum to give a yellow crude product 24 mg. (89%). $^1$H NMR (300 MHz, CD₃OD) δ 8.85 (s, 1H), 8.46 (d, J=5.4 Hz, 1H), 7.59 (d, J=5.7 Hz, 1H), 7.14 (s, 1H), 4.19 (t, J=7.2 Hz, 2H), 3.22 (t, J=7.2 Hz, 2H); LC-MS (ESI) m/z 302.0 (M+1).

1-(3-Chloro-phenyl)-3-{5-[2-(6-cyano-thieno[3,2-b]pyridin-7-ylamino)-ethyl]-thiazol-2-yl}-urea (Compound 190)

To a solution of 7-[2-(2-amino-thiazol-5-yl)-ethylamino]-thieno[3,2-b]pyridine-6-carbonitrile (27.1 mg, 0.09 mmol) in 2 ml of dichloromethane was added 3-chloro phenyl isocyanate (0.02 ml, 0.16 mmol). The resulting mixture was stirred at room temperature for 16 hr and filtered. Solids were washed with CH₂Cl₂, and the combined organics were concentrated. The residue was purified by chromatography on TLC plate with MeOH/CH₂Cl₂/NH₃$_{(aq)}$=1/20/0.1 to give 5.6 mg (14%) of a white solid. $^1$H NMR (400 MHz, CD₃OD) δ 8.41 (s, 1H), 8.06 (d, J=5.6 Hz, 1H), 7.62-7.66 (m, 1H), 7.43 (d, J=5.2 Hz, 1H), 7.25-7.31 (m, 2H), 7.16 (s, 1H), 7.00-7.07 (m, 1H), 4.06 (t, J=7.2 Hz, 2H), 3.20 (t, J=7.2 Hz, 2H). LC-MS (ESI) m/z 455.0 (M+1).

Examples 9-69

Syntheses of Compounds 20, 22, 47, 56, 72, 81, 140, and 201-254

Compounds 20, 22, 47, 56, 72, 81, 140, and 201-254 were prepared in a manner similar to that described in Example 2, 4, 7, or 8. $^1$H NMR and MS data of these compounds are listed below.

Compound 20: $^1$H-NMR (400 MHz, CD₃OD): δ 8.39 (s, 1H), 7.97-7.95 (d, J=9.2 Hz, 1H), 7.42-7.40 (m, 2H), 7.36-7.33 (m, 2H), 7.30-7.26 (m, 2H), 7.22-7.20 (d, J=8.4 Hz, 2H), 7.13-7.10 (dd, J=8.8, 2.4 Hz, 1H), 7.08-7.07 (d, J=2.4 Hz, 1H), 7.03-7.01 (t, 1H), 4.20 (t, 2H), 3.82 (t, 2H), 3.69 (t, 2H), 2.99 (t, 2H), 2.84 (t, 2H), 2.74-2.71 (m, 3H), 2.06-2.03 (m, 2H), 1.13 (t, 2H). LC-MS (ESI) m/z: 529.4 (M+1).

Compound 22: $^1$H-NMR (400 MHz, d₆-DMSO): δ 8.93 (s, 1H, NH), 8.72 (s, 1H, NH), 8.41 (s, 1H), 8.20 (t, 1H, NH), 8.12-8.10 (d, J=9.2 Hz, 1H), 7.50-7.46 (m, 1H), 7.37-7.36 (d, J=8.8 Hz, 2H), 7.32-7.26 (m, 1H), 7.19-7.16 (d, J=8.4 Hz, 2H), 7.11-7.08 (m, 2H), 7.05-7.04 (d, J=2.4 Hz, 1H), 6.79-6.74 (m, 1H), 4.15 (t, 2H), 3.72-3.67 (m, 2H), 3.46 (t, 2H), 2.91 (t, 2H), 2.62 (t, 2H), 2.55-2.51 (m, 4H), 1.90-1.85 (m, 2H), 0.98 (t, 2H). LC-MS (ESI) m/z 547.3 (M+1).

Compound 47: $^1$H-NMR (300 MHz CDCl₃): δ 8.49 (s, 1H), 7.46 (d, J=7.2 Hz, 2H), 7.34 (d, J=7.2 Hz, 2H), 7.16 (s, 1H), 7.14 (s, 1H), 7.10 (t, J=7.2 Hz, 1H), 7.06 (s, 1H), 4.02 (s, 3 h), 4.00 (s, 3H), 3.87 (t, J=6.6 Hz, 2H), 3.18 (t, J=6.6 Hz, 2H), LC-MS (ESI) m/z: 451.1 (M+1).

Compound 56: $^1$H-NMR (400 MHz, d₆-DMSO): δ 9.23 (s, 1H, NH), 8.36 (s, 1H), 8.12 (t, 1H), 7.59 (s, 1H), 7.49-7.47 (m, 1H), 7.34-7.31 (m, 1H), 7.14-7.09 (m, 3H), 6.84-6.83 (m, 1H), 3.90 (s, 3H), 3.89 (s, 3H), 3.73 (m, 2H), 3.08 (t, 2H). LC-MS (ESI) m/z 469.1 (M+1).

Compound 72: $^1$H-NMR (400 MHz, CDCl₃) δ 9.92 (s, 1H), 8.42 (brs, 1H), 8.17 (d, 2H), 8.02 (d, 1H), 7.49-7.56 (m, 3H), 7.22-7.34 (m, 5H), 7.03 (dd, 1H), 6.95 (td, 1H), 6.46 (s, 1H), 5.79 (t, 1H), 3.95 (brs, 2H), 3.38 (s, 2H), 3.01 (t, 2H), 2.02 (s, 6H). LC-MS (ESI): m/z: 508.2 (M+1).

Compound 81: $^1$H-NMR (400 MHz DMSO-d₆): δ 8.94 (s, 1H), 8.48-8.11 (m, 5H), 7.61-7.27 (m, 6H), 7.14 (s, 1H), 7.01 (t, J=7.2 Hz, 1H), 3.74 (m, 2H), 3.07 (t, J=6.8 Hz, 2H). LC-MS (ESI) m/z: 458.1 (M+1).

Compound 140: $^1$H NMR (300 MHz CD₃OD): δ 8.33 (s, 1H), 7.43-7.19 (m, 10H), 7.03-6.98 (m, 1H), 4.08 (t, J=7.2 Hz, 2H), 3.96 (s, 3H), 3.94 (s, 3H), 3.05 (t, J=7.8 Hz, 2H). LCMS-ESI (m/z): 468.2 (M+1).

Compound 201: $^1$H-NMR δ 9.95 (s, 1H), 8.91 (s, 1H), 8.80 (s, 1H), 7.92 (s, 1H), 7.43-7.35 (m, 4H), 7.26-7.15 (m, 4H), 6.92 (t, 2H, J=7.5 Hz), 3.94 (s, 3H), 3.92 (s, 1H), 3.87 (q, 2H, J=7.2 Hz), 2.93 (t, 2H, J=7.8 Hz).

Compound 202: $^1$H-NMR (300 MHz, d₆-DMSO): δ 10.37 (t, 1H), 9.34 (s, 1H, NH), 9.32 (s, 1H, NH), 8.84 (s, 1H), 8.54 (d, J=9.0 Hz, 2H), 7.45-7.14 (m, 10H), 6.95-6.90 (m, 1H), 4.28 (t, 2H), 3.92-3.80 (m, 2H), 3.27-3.20 (m, 2H), 2.97 (t, 2H), 2.78 (s, 3H), 2.77 (s, 3H), 2.26-2.21 (m, 2H). LC-MS (ESI) m/z: 485.1 (M+1).

Compound 203: $^1$H-NMR (300 MHz, d₆-DMSO): δ 10.38 (br, 1H, NH), 10.21 (br, 1H), 9.33 (m, 2H), 8.84 (s, 1H), 8.55 (d, J=9.0 Hz, 2H), 7.45-7.14 (m, 10H), 6.95-6.90 (m, 1H), 4.29 (t, 2H), 3.90-3.88 (m, 2H), 3.80-3.77 (m, 2H), 3.45-3.20 (m, 6H), 2.97 (t, 2H), 2.27-2.23 (m, 2H), 1.28 (t, 2H). LC-MS (ESI) m/z: 529.2 (M+1).

Compound 204: $^1$H NMR (400 MHz, d₆-DMSO) δ 9.01 (s, 1H), 8.72 (s, 1H), 8.35 (s, 1H), 8.00 (br. s, 2H), 7.49-7.56 (m, 3H), 7.38 (d, 2H), 7.29 (d, 1H), 7.19 (d, 2H), 7.07 (s, 1H), 3.88 (s, 3H), 3.86 (s, 3H), 3.69 (td, 2H), 2.89 (t, 2H). LC-MS (ESI) m/z 512.3 (M+1).

Compound 205: $^1$H NMR (300 MHz, CDCl₃) δ 8.52 (s, 1H), 7.87 (s, 1H), 7.62 (s, 1H), 7.09-7.17 (m, 4H), 7.02 (d, 2H), 6.84-6.89 (m, 3H), 6.58 (dd, 1H), 6.52 (t, 1H), 3.86 (s, 3H), 3.82 (s, 3H), 3.72 (s, 3H), 3.64 (td, 2H), 2.84 (t, 2H). LC-MS (ESI) m/z 474.2 (M+1).

Compound 206: $^1$H-NMR (400 MHz, d₆-DMSO) δ 8.61 (s, 1H), 8.58 (s, 1H), 8.31 (s, 1H), 8.27 (br, 1H), 8.04 (d, J=8.8 Hz, 2H), 7.43 (t, J=7.6 Hz, 2H), 7.37 (d, J=8.4 Hz, 2H), 7.27-7.12 (m, 6H), 6.94 (t, J=7.6 Hz, 1H), 3.84 (s, 3H), 3.70 (br, 2H), 2.88 (t, J=7.2 Hz, 2H). LC-MS (ESI) m/z: 481.3 (M+1).

Compound 207: $^1$H-NMR (400 MHz, d₆-DMSO): δ 8.93 (s, 1H, NH), 8.72 (s, 1H, NH), 8.41 (s, 1H), 8.20 (t, 1H, NH), 8.12-8.10 (d, J=8.8 Hz, 1H), 7.50-7.46 (m, 1H), 7.38-7.36 (d, J=8.4 Hz, 2H), 7.32-7.26 (m, 1H), 7.18-7.16 (d, J=8.8 Hz, 2H), 7.11-7.08 (m, 2H), 7.05-7.04 (d, J=2.8 Hz, 1H), 6.77-6.76 (m, 1H), 4.15 (t, 2H), 3.72-3.67 (q, 2H), 2.91 (t, 2H), 2.45 (t, 2H), 2.21 (s, 6H), 1.93-1.89 (m, 2H). LC-MS (ESI) m/z 503.3 (M+1).

Compound 208: $^1$H-NMR (300 MHz, d₆-DMSO): δ 10.67 (br, 1H), 10.34 (br, 1H, NH), 9.67 (br, 1H, NH), 9.38 (br, 1H, NH), 8.84 (s, 1H), 8.53 (d, J=9.3 Hz, 2H), 7.50-7.06 (m, 9H), 6.77-6.71 (m, 1H), 4.28 (t, 2H), 3.90-3.88 (m, 2H), 3.23-3.22

(m, 2H), 2.97 (t, 2H), 2.79 (s, 3H), 2.77 (s, 3H), 2.26-2.21 (m, 2H). LC-MS (ESI) m/z 503.1 (M+1).

Compound 209: $^1$H-NMR (300 MHz, d$_6$-DMSO): δ 10.38 (br, 1H, NH), 10.21 (br, 1H), 9.72 (s, 1H, NH), 9.42 (s, 1H, NH), 8.84 (s, 1H), 8.55 (d, J=9.3 Hz, 2H), 7.50-7.06 (m, 10H), 6.76-6.70 (m, 1H), 4.28 (t, 2H), 3.89-3.88 (m, 2H), 3.79-3.77 (m, 2H), 3.34-3.20 (m, 6H), 2.97 (t, 2H), 2.27-2.22 (m, 2H), 1.28 (t, 2H). LC-MS (ESI) m/z 547.2 (M+1).

Compound 210: $^1$H NMR (300 MHz, d$_6$-DMSO) δ 8.64 (s, 1H), 8.57 (s, 1H), 8.35 (s, 1H), 8.02 (t, 1H), 7.56 (s, 1H), 7.41-7.46 (m, 2H), 7.36 (d, 2H), 7.17 (d, 2H), 7.11 (d, 1H), 7.07 (s, 1H), 3.87 (s, 3H), 3.86 (s, 3H), 3.68 (td, 2H), 2.88 (t, 2H). LC-MS (ESI) m/z 462.2 (M+1).

Compound 211: $^1$H NMR (400 MHz, d$_6$-DMSO) δ 8.75 (s, 2H), 8.68 (s, 1H), 7.81 (s, 1H), 7.41-7.45 (m, 2H), 7.37 (d, 2H), 7.18 (s, 1H), 7.15 (d, 1H), 7.10 (t, 2H), 3.94 (s, 3H), 3.91 (s, 3H), 3.85 (dd, 2H), 2.92 (t, 2H).

Compound 212: $^1$H NMR (CD$_3$OD): δ 8.39 (s, 1H), 8.02 (d, J=9.3 Hz, 1H), 7.34-7.12 (m, 13H), 7.02-6.98 (m, 1H), 4.06 (t, J=7.5 Hz, 2H), 3.93 (s, 3H), 3.04 (t, J=7.5 Hz, 2H). LCMS-ESI (m/z): 460.1 (M+1).

Compound 213: $^1$H NMR (CD$_3$OD): δ 8.39 (s, 1H), 8.02 (d, J=9.3 Hz, 1H), 7.34 (d, J=8.7 Hz, 2H), 7.26-7.12 (m, 10H), 7.02-6.98 (m, 1H), 4.06 (t, J=7.5 Hz, 2H), 3.93 (s, 3H), 3.04 (t, J=7.5 Hz, 2H). LCMS-ESI (m/z): 472.1 (M+1).

Compound 214: $^1$H NMR (CD$_3$OD): δ 8.31 (s, 1H), 7.98 (d, J=5.4 Hz, 1H), 7.37-7.29 (m, 6H), 7.25-7.16 (m, 6H), 6.95 (t, J=7.5 Hz, 1H), 3.94 (dt, J=7.5, 6.6 Hz, 2H), 2.94 (t, J=6.6 Hz, 2H). LCMS-ESI (m/z): 414.1 (M+1).

Compound 215: $^1$H NMR (CD$_3$OD): δ 8.38 (s, 1H), 8.04 (d, J=4.2 Hz, 1H), 7.41 (d, J=4.2 Hz, 1H), 7.36-7.34 (m, 6H), 7.27-7.23 (m, 4H), 7.02-6.99 (m, 1H), 4.02 (d, J=5.4 Hz, 2H), 3.00 (d, J=5.4 Hz, 2H). LCMS-ESI (m/z): 448.0 (M+1).

Compound 216: $^1$H NMR (CD$_3$OD): δ 8.29 (s, 1H), 7.62-7.60 (m, 1H), 7.56-7.55 (m, 2H), 7.36-7.33 (m, 2H), 7.25-7.22 (m, 6H), 7.01-6.98 (m, 1H), 4.01 (t, J=5.4 Hz, 2H), 3.02 (t, J=5.4 Hz, 2H). LCMS-ESI (m/z): 448.0 (M+1).

Compound 217: $^1$H-NMR (400 MHz, d$_6$-DMSO): δ 8.69 (s, 1H, NH), 8.66 (s, 1H, NH), 8.39 (s, 1H), 8.25 (t, 1H, NH), 7.63-7.60 (m, 2H), 7.46-7.36 (m, 5H), 7.27 (t, 2H), 7.19-7.17 (d, J=8.4 Hz, 2H), 6.97 (t, 1H), 4.11 (t, 2H), 3.75-3.70 (m, 2H), 2.93 (t, 2H), 2.42 (t, 2H), 1.95-1.89 (m, 2H). LC-MS (ESI) m/z 485.2 (M+1).

Compound 218: $^1$H NMR (400 MHz, CD$_3$OD) δ 8.34 (s, 1H), 7.63 (m, 1H), 7.43 (s, 1H), 7.34 (d, J=8.4 Hz, 2H), 7.23-7.25 (m, 4H), 7.21 (s, 1H), 6.99-7.01 (m, 1H), 4.09 (t, J=7.6 Hz, 2H), 3.97 (s, 3H), 3.96 (s, 3H), 3.06 (t, J=7.6 Hz, 2H). LC-MS (ESI) m/z 502.1 (M+1).

Compound 219: $^1$H NMR (400 MHz, CD$_3$OD) δ 8.34 (s, 1H), 7.43 (m, 1H), 7.34 (d, J=8.4 Hz, 2H), 7.22-7.24 (m, 3H), 7.21 (s, 1H), 7.19 (m, 1H), 7.16 (t, J=7.2 Hz, 1H), 6.85 (d, J=7.2 Hz, 1H), 4.09 (t, J=7.6 Hz, 2H), 3.97 (s, 3H), 3.95 (s, 3H), 3.06 (t, J=7.6 Hz, 2H), 2.32 (s, 3H). LC-MS (ESI) m/z 482.2 (M+1).

Compound 220: $^1$H-NMR (400 MHz, d$_6$-DMSO) δ 10.35 (s, 1H), 8.62 (s, 1H), 8.59 (s, 1H), 8.30 (s, 1H), 8.24 (br, 1H), 7.96 (d, J=8.4 Hz, 2H), 7.43 (d, J=8.0 Hz, 2H), 7.37 (d, J=8.4 Hz, 2H), 7.26 (t, J=8.0 Hz, 2H), 7.16 (d, J=8.0 Hz, 2H), 6.97-6.92 (m, 3H), 3.69 (br, 2H), 2.87 (t, J=7.2 Hz, 2H). LC-MS (ESI) m/z 467.1 (M+1).

Compound 221: $^1$H NMR (400 MHz, d$_6$-DMSO) δ 10.20 (s, 1H), 8.41 (t, J=6.4 Hz, 1H), 8.35 (s, 1H), 8.12-8.10 (m, 2H), 7.93 (d, J=7.2 Hz, 2H), 7.70 (d, J=8.0 Hz, 2H), 7.61-7.49 (m, 6H), 7.24 (t, J=8.0 Hz, 2H), 3.73 (q, J=6.4 Hz, 2H), 2.92 (t, J=6.4 Hz, 2H). LC-MS (ESI) m/z: 436.1 (M+1).

Compound 222: $^1$H NMR (400 MHz, d$_6$-DMSO) δ 9.26 (s, 1H), 8.77 (d, J=3.6 Hz, 1H), 8.61 (s, 1H), 8.58 (s, 1H), 8.49 (t, J=6.8 Hz, 1H), 8.42 (d, J=8.0 Hz, 1H), 8.37 (s, 1H), 7.63 (dd, J=8.0, 3.6 Hz, 1H), 7.43 (d, J=8.0 Hz, 2H), 7.37 (d, J=8.0 Hz, 2H), 7.25 (t, J=8.0 Hz, 2H), 7.16 (d, J=8.0 Hz, 2H), 6.94 (t, J=8.0 Hz, 1H), 3.71 (q, J=6.8 Hz, 2H), 2.88 (t, J=6.8 Hz, 2H). LC-MS (ESI) m/z: 452.1 (M+1).

Compound 223: $^1$H NMR (400 MHz, d6-DMSO) δ 9.29 (s, 1H), 8.91 (s, 1H), 8.88 (s, 1H), 8.82 (d, J=4.8 Hz, 1H), 8.54-8.47 (m, 2H), 8.38 (s, 1H), 7.77-7.71 (m, 1H), 7.42 (d, J=7.6 Hz, 2H), 7.36 (d, J=8.4 Hz, 2H), 7.24 (t, J=8.0 Hz, 2H), 7.15 (d, J=8.0 Hz, 2H), 6.92 (t, J=8.0 Hz, 1H), 3.71 (m, 2H), 2.87 (t, J=7.0 Hz, 2H). LC-MS (ESI) m/z: 452.1 (M+1).

Compound 224: $^1$H NMR (400 MHz, CD$_3$OD) δ 8.34 (s, 1H), 7.45 (s, 1H), 7.39 (dd, 2H), 7.24-7.28 (m, 4H), 7.07 (s, 1H), 7.02 (dd, 2H), 3.95 (s, 3H), 3.93 (s, 3H), 3.82 (t, 2H), 2.99 (t, 2H). LC-MS (ESI) m/z 441.2 (M+1).

Compound 225: $^1$H NMR (400 MHz, CD$_3$OD) δ 8.34 (s, 1H), 7.43 (s, 1H), 7.40 (t, J=2.4 Hz, 1H), 7.35 (d, J=8.4 Hz, 2H), 7.23-7.29 (m, 3H), 7.21 (s, 1H), 7.07 (dd, J=8, 2 Hz, 1H), 6.73 (m, 1H), 4.09 (t, J=7.6 Hz, 2H), 3.98 (s, 3H), 3.96 (s, 3H), 3.06 (t, J=7.6 Hz, 2H). LC-MS (ESI) m/z 486.2

Compound 226: $^1$H NMR (CDCl$_3$, 400 MHz) δ 8.49 (s, 1H), 7.65 (s, 1H), 7.41 (d, J=8.4 Hz, 1H), 7.23 (d, J=8 Hz, 1H), 7.11 (s, 1H), 6.66 (s, 1H), 5.32 (t, J=4.8 Hz, 1H), 4.157 (q, J=6.4 Hz, 2H), 4.00 (s, 3H, OCH$_3$), 3.90 (s, 3H), 3.08 (t, J=6.4 Hz, 2H), 2.59-2.62 (m, 1H), 0.82-0.89 (m, 2H), 0.67-0.71 (m, 2H). LC-MS (ESI) m/z 432.2 (M+1).

Compound 227: $^1$H NMR (400 MHz, CD$_3$OD+CDCl$_3$) δ 8.43 (s, 1H), 7.46 (d, J=8.4 Hz, 2H), 7.31-7.35 (m, 2H), 7.26 (s, 1H), 7.18 (s, 1H), 7.04-7.13 (m, 3H), 4.13 (t, J=6.8 Hz, 2H), 4.02 (s, 3H), 4.01 (s, 3H), 3.25 (t, J=6.8 Hz, 2H). LC-MS (ESI) m/z 475 (M+1).

Compound 228: $^1$H-NMR (400 MHz, d$_6$-DMSO): δ 9.20 (s, 1H, NH), 8.39 (s, 1H), 8.16-8.15 (m, 1H), 7.71 (s, 1H), 7.60 (s, 1H), 7.32-7.31 (m, 2H), 7.15-7.06 (m, 3H), 3.90 (s, 3H), 3.89 (s, 3H), 3.74-3.73 (m, 2H), 3.09 (t, 2H). LC-MS (ESI) m/z 485.1 (M+1).

Compound 229: $^1$H NMR (400 MHz, CD$_3$OD) δ 8.33 (s, 1H), 7.96 (d, 1H), 7.24-7.39 (m, 9H), 7.01-7.08 (m, 3H), 4.04 (t, 2H), 3.03 (t, 2H). LC-MS (ESI) m/z 424.2 (M+1).

Compound 230: $^1$H NMR (400 MHz, d$_6$-DMSO) δ 12.01 (br s, 1H), 8.34 (s, 1H), 8.19 (s, 1H), 8.01 (t, 1H), 7.56 (s, 1H), 7.31 (d, 2H), 7.11 (d, 2H), 7.07 (s, 1H), 6.32 (d, 1H), 3.87 (s, 3H), 3.86 (s, 3H), 3.67 (td, 2H), 2.85 (t, 2H), 0.58-0.62 (m, 2H). 0.35-0.39 (m, 2H). LC-MS (ESI) m/z 408.2 (M+1).

Compound 231: $^1$H NMR (300 MHz, CD$_3$OD) δ 8.35 (s, 1H), 7.76 (d, J=9 Hz, 1H), 7.49 (d, J=2.4 Hz, 1H), 7.23-7.43 (m, 9H), 6.99-7.04 (m, 1H), 4.12 (t, J=7.5 Hz, 2H), 3.93 (s, 3H), 3.08 (t, J=7.5 Hz, 2H). LC-MS (ESI) m/z 438.2 (M+1).

Compound 232: $^1$H-NMR (400 MHz, DMSO-d$_6$) δ 8.65 (s, 1H), 8.62-8.60 (m, 2H), 7.45-7.39 (m, 4H), 7.30-7.25 (m, 6H), 6.96 (t, 1H, J=7.2 Hz), 4.67 (t, 1H, J=6.4 Hz), 3.95 (s, 3H), 3.92 (s, 3H), 3.10 (t, 1H, J=6.4 Hz). LC-MS (ESI) m/z: 445.2 (M+1).

Compound 233: $^1$H NMR (CD$_3$OD): δ 8.28 (s, 1H), 7.57 (d, J=9.3 Hz, 1H), 7.43-7.19 (m, 11H), 7.07 (dd, J=9.3, 2.4 Hz, 1H), 7.01 (d, J=2.4 Hz), 6.72 (d, J=2.4 Hz, 1H), 3.75 (t, J=7.8 Hz), 3.10 (s, 6H), 2.93 (t, J=7.8 Hz). LCMS-ESI (m/z): 427.2 [M+H$^+$].

Compound 234: $^1$H NMR (400 MHz, d$_6$-DMSO) δ 13.90 (s, 1H), 9.73 (t, J=5.4 Hz, 1H), 9.06 (d, J=8.0 Hz, 2H), 8.68 (s, 1H), 8.23 (d, J=9.6 Hz, 1H), 7.44 (d, J=8.0 Hz, 2H), 7.37 (d, J=8.4 Hz, 2H), 7.28-7.22 (m, 3H), 7.15 (d, J=8.4 Hz, 2H), 6.94 (t, J=7.4 Hz, 1H), 6.64 (d, J=2.0 Hz, 1H), 3.84 (dd, J=9.8 Hz, 6.8 Hz, 2H), 3.11 (s, 6H), 2.92 (t, J=7.2 Hz, 2H). LC-MS (ESI) m/z 427.1 (M+1).

Compound 235: $^1$H NMR (400 MHz, d$_6$-DMSO) δ 8.82 (d, J=6.0 Hz, 2H), 8.62 (s, 1H), 8.59 (s, 1H), 8.40 (s, 1H), 8.00 (d, J=6.0 Hz, 2H), 7.43 (d, J=8.0 Hz, 2H), 7.36 (d, J=8.0 Hz, 2H), 7.27-7.23 (m, 3H), 7.17 (d, J=8.0 Hz, 2H), 6.94 (t, J=7.2 Hz, 1H), 3.72 (q, J=7.2 Hz, 2H), 2.88 (t, J=7.2 Hz, 2H). LC-MS (ESI) m/z: 452.2 (M+1).

Compound 236: $^1$H NMR (300 MHz, d$_6$-DMSO) δ 8.93 (d, J=6.0 Hz, 2H), 8.91 (s, 1H), 8.88 (s, 1H), 8.70-8.68 (m, 1H), 8.43 (s, 1H), 8.22 (d, J=6.0 Hz, 2H), 7.43 (d, J=7.5 Hz, 2H), 7.37 (d, J=8.4 Hz, 2H), 7.26 (t, J=8.0 Hz, 2H), 7.17 (d, J=8.1 Hz, 2H), 6.94 (t, J=7.2 Hz, 1H), 4.01 (s, 1H), 3.75-3.71 (m, 2H), 2.89 (t, J=7.2 Hz, 2H). LC-MS (ESI) m/z: 452.1 (M+1).

Compound 237: $^1$H NMR (400 MHz, d$_6$-DMSO) δ 8.77 (d, J=4.0 Hz, 1H), 8.62 (s, 1H), 8.58 (s, 1H), 8.58-8.51 (m, 1H), 8.38 (s, 1H), 8.21 (d, J=7.6 Hz, 1H), 8.04 (t, J=7.6 Hz, 1H), 7.60 (t, J=6.8 Hz, 1H), 7.43 (d, J=8.0 Hz, 2H), 7.37 (d, J=7.2 Hz, 2H), 7.26 (t, J=7.2 Hz, 2H), 7.17 (d, J=8.0 Hz, 2H), 6.94 (t, J=7.2 Hz, 1H), 3.72 (q, J=6.8 Hz, 2H), 2.89 (t, J=6.8 Hz, 2H). (FAB) m/z: 452 (M+1).

Compound 238: $^1$H NMR (400 MHz, d$_6$-DMSO) δ 8.38 (br, 1H), 8.33 (s, 1H), 8.19 (s, 1H), 8.12-8.10 (m, 2H), 7.64-7.60 (m, 3H), 7.31 (d, J=8.0 Hz, 2H), 7.11 (d, J=8.0 Hz, 2H), 6.32 (d, J=1.2 Hz, 1H), 3.69 (q, J=6.8 Hz, 2H), 2.85 (t, J=6.8 Hz, 2H), 2.52-2.50 (m, 1H), 0.63-0.58 (m, 2H), 0.39-0.35 (m, 2H). LC-MS (ESI) m/z: 415.2 (M+1).

Compound 239: $^1$H NMR (CD$_3$OD): δ 8.82 (s, 1H), 8.27 (d, J=9.6 Hz, 1H), 7.41-7.16 (m, 12H), 7.07 (dd, J=9.6, 2.7 Hz, 1H), 7.00 (t, J=7.2 Hz), 4.35 (q, J=7.2 Hz, 2H), 4.09 (t, J=6.6 Hz, 2H), 2.99 (t, J=6.6 Hz, 2H), 1.39 (t, J=7.2 Hz, 3H). LCMS-ESI (m/z): 485.2 [M+H$^+$].

Compound 240: $^1$H-NMR (400 MHz, DMSO-d$_6$) δ 8.76 (s, 1H), 8.73 (s, 1H), 7.44 (d, 2H, J=8.0 Hz), 7.37 (d, 2H, J=8.0 Hz), 7.28-7.24 (m, 3H), 7.20-7.15 (m, 3H), 6.95 (t, 1H, J=7.2 Hz), 3.91 (s, 3H), 3.86-3.80 (m, 8H), 2.99 (t, 1H, J=7.2 Hz). LC-MS (ESI) m/z: 458.2 (M+1).

Compound 241: $^1$H-NMR (300 MHz, d$_6$-DMSO): δ 9.16 (s, 1H, NH), 8.49 (br, 1H, NH), 8.36 (s, 1H), 8.13 (br, 1H), 7.64-7.62 (m, 3H), 7.49-7.45 (m, 1H), 7.36-7.31 (m, 1H), 7.17-7.15 (m, 2H), 6.85-6.80 (m, 1H), 3.76-3.67 (m, 2H), 3.10 (t, 2H). LC-MS (ESI) m/z 476.1 (M+1).

Compound 242: $^1$H-NMR (300 MHz, d$_6$-DMSO): δ 9.16 (s, 1H, NH), 8.48 (br, 1H, NH), 8.36 (s, 1H), 8.13 (br, 1H), 7.69 (s, 1H), 7.63 (br, 3H), 7.30 (br, 2H), 7.15 (s, 1H), 7.05 (br, 1H), 3.75-3.74 (m, 2H), 3.09 (t, 2H). LC-MS (ESI) m/z 492.1 (M+1).

Compound 243: $^1$H NMR (400 MHz, d$_6$-DMSO) δ 8.61 (s, 1H), 8.57 (s, 1H), 8.26 (s, 1H), 8.13 (br, 1H), 7.43 (d, J=8.0 Hz, 2H), 7.35 (d, J=8.0 Hz, 2H), 7.26 (t, J=8.0 Hz, 2H), 7.14 (d, J=8.0 Hz, 2H), 6.94 (d, J=8.0 Hz, 1H), 3.65 (br, 2H), 2.83 (t, J=7.2 Hz, 2H), 2.56 (s, 3H). LC-MS (ESI) m/z: 389.1 (M+1).

Compound 244: $^1$H NMR (300 MHz, d$_6$-DMSO δ 9.47 (s, 1H), 9.16 (s, 1H), 8.35 (s, 1H), 8.01 (t, 1H), 7.62 (s, 1H), 7.56 (s, 1H), 7.40 (d, 2H), 7.14-7.22 (m, 3H), 7.07 (s, 1H), 6.73 (tt, 1H), 3.87 (s, 3H), 3.86 (s, 3H), 3.79 (td, 2H), 2.88 (t, 2H). LC-MS (ESI) m/z: 480.2 (M+1).

Compound 245: $^1$H NMR (300 MHz, d$_6$-DMSO) δ 9.86 (brt, 1H), 9.46 (s, 1H), 9.07 (s, 1H), 8.79 (s, 1H), 7.90 (s, 1H), 7.37 (d, 2H), 7.13-7.20 (m, 5H), 6.76 (tt, 1H), 3.95 (s, 3H), 3.93 (s, 3H), 3.85 (td, 2H), 2.94 (t, 2H).

Compound 246: $^1$H NMR (400 MHz, d$_6$-DMSO) δ 9.01 (s 1H), 8.51 (s, 1H), 8.35 (s, 1H), 8.14 (t, 1H), 8.02 (s, 1H), 7.37 (d, 2H), 7.17-7.24 (m, 3H), 7.11 (t, 2H), 6.97-6.99 (m, 2H), 3.87 (s, 3H), 3.86 (s, 3H), 3.69 (dt, 2H), 2.89 (t, 2H). LC-MS (ESI) m/z 462.2 (M+1).

Compound 247: $^1$H NMR (400 MHz, d$_6$-DMSO) δ 8.89 (s, 1H), 8.70 (s, 1H), 8.36 (s, 1H), 8.03 (brt, 1H), 7.57 (s, 1H), 7.38 (d, 2H), 7.30 (t, 1H), 7.17 (d, 2H), 7.06-7.09 (m, 3H), 3.71 (s, 3H), 3.68 (s, 3H), 3.69 (dt, 2H), 2.89 (t, 2H). LC-MS (ESI) m/z 480.2 (M+1).

Compound 248: $^1$H NMR (300 MHz, d$_6$-DMSO) δ 8.64 (s, 1H), 8.60 (s, 1H), 8.48 (s, 1H), 8.37 (br. t, 1H), 8.19 (dd, 1H), 7.74 (td, 1H), 7.66 (d, 1H), 7.51 (tt, 1H), 7.42 (d, 2H), 7.35 (d, 2H), 7.25 (t, 2H), 7.17 (d, 2H), 6.94 (tt, 1H), 3.72 (td, 2H), 2.89 (t, 2H). LC-MS (ESI) m/z 484.3 (M+1).

Compound 249: $^1$H NMR (400 MHz, d$_6$-DMSO) δ 10.36 (t, 2H), 8.95 (s, 1H), 8.93 (s, 1H), 8.92 (s, 1H), 8.49 (d, 1H), 8.03 (t, 1H), 7.76-7.83 (m, 2H), 7.42 (d, 2H), 7.39 (d, 2H), 7.24 (d, 2H), 7.17 (d, 2H), 6.93 (tt, 1H), 3.91 (td, 2H), 2.95 (t, 2H).

Compound 250: $^1$H-NMR (400 MHz, DMSO-d$_6$) δ 8.91 (s, 1H), 8.85 (s, 1H), 8.83 (s, 1H), 8.71 (s, 1H), 8.60 (m, 2H), 8.41 (s, 1H), 8.02~8.01 (m, 2H), 7.48 (dt, 1H, J=11.6, 2.0 Hz), 7.39-7.37 (m, 2H), 7.28 (m, 2H), 7.20-7.18 (m, 2H), 7.09 (d, 1H, J=8.4 Hz), 6.76 (td, 1H, J=8.4, 2.0 Hz), 4.00-3.72 (m, 2H), 2.90 (t, 1H, J=7.2 Hz). LC-MS (ESI) m/z: 470.2 (M+1).

Compound 251: $^1$H NMR (300 MHz, DMSO-d$_6$) δ 8.61 (s, 1H), 8.58 (s, 1H), 8.35 (s, 1H), 8.03-8.07 (m, 2H), 7.44 (d, J=7.8 Hz, 2H), 7.37 (d, J=8.7 Hz, 2H), 7.24-7.29 (m, 3H), 7.16 (d, J=8.4 Hz, 2H), 6.95 (t, J=7.5 Hz, 1H), 6.91 (d, J=2.1 Hz, 1H), 3.76 (t, J=5.1 Hz, 4H), 3.65-3.72 (m, 2H), 3.28-3.38 (m, 4H), 2.88 (t, J=7.5 Hz, 2H). LC-MS (ESI) m/z 469.1 (M+1).

Compound 252: $^1$H NMR (300 MHz, DMSO-d$_6$) δ 10.48 (br s, 1H), 9.14 (s, 1H), 8.37 (s, 1H), 8.12 (t, J=5.4 Hz, 1H), 7.85 (s, 1H), 7.59 (s, 1H), 7.14-7.26 (m, 4H), 7.10 (s, 1H), 3.89 (s, 6H), 3.74 (q, J=6.9 Hz, 2H), 3.078 (t, J=6.9 Hz, 2H). LC-MS (ESI) m/z 530.9 (M+1).

Compound 253: $^1$H NMR (300 MHz, DMSO-d$_6$) δ 8.61 (s, 1H), 8.58 (s, 1H), 8.48 (m, 2H), 8.29-8.34 (m, 1H), 7.36-7.45 (m, 6H), 7.27 (t, J=7.8 Hz, 2H), 7.17 (d, J=8.4 Hz, 2H), 6.95 (t, J=7.2 Hz, 1H), 3.73 (q, J=7.5 Hz, 2H), 2.90 (t, J=7.5 Hz, 2H). LC-MS (ESI) m/z 402.1 (M+1).

Compound 254: $^1$H NMR (300 MHz, DMSO-d$_6$) δ 10.24 (br s, 1H), 8.91 (s, 1H), 8.81 (s, 1H), 8.79 (s, 1H), 8.57 (dd, J=9.3, 5.4 Hz, 1H), 7.73 (td, J=9, 2.7 Hz, 1H), 7.57 (dd, J=9, 2.7 Hz, 1H), 7.43 (d, J=8.4 Hz, 2H), 7.38 (d, J=8.1 Hz, 2H), 7.26 (t, J=7.8 Hz, 2H), 7.18 (d, J=8.7 Hz, 2H), 6.95 (t, J=7.2 Hz, 1H), 3.91 (q, J=7.5 Hz, 2H), 2.95 (t, J=7.2 Hz, 2H). MS (ESI) m/z 402.1 (M+1).

Example 70

Inhibiting Aurora A Activity

Aurora Kinase A Protein Purification:

The GST-tAurora A (123-401aa) fusion protein was produced by baculovirus expression system. The Aurora A catalytic domain with an N-terminal GST tag was constructed in pBacPAK8 plasmid and expressed in sf9 cells. Recombinant baculovirus infected sf9 cells were harvested by centrifugation, and the pellets were resuspended in PBS buffer (PBS, pH 7.3, 0.2 mM PMSF, 0.5 mM Na$_3$VO$_4$, 0.5 mM EDTA, 2 mM DTT, Complete Protease Inhibitor Cocktail table (1125700, Roche). Cells were lysed by sonication, and lysates were cleared by centrifugation at 15,000 rpm for 30 min. The supernatants were loaded into 1 ml of GST Sepharose 4 Fast Flow (17-5132-01, GE healthcare) column previously washed with PBS buffer. The column were washed with 30 volumes of PBS buffer, and then eluted by elution buffer (50 mM Tris (pH 8.0), 10 mM glutathione). To concentrate GST-tAurora A, buffer was replaced with Tris buffer (100 mM Tris (pH 7.5), 300 mM NaCl, 1 mM EDTA, 4 mM DTT) using Amicon ultra-15 (MWCO:30K, Millipore)

to 2.4 mg/ml. After the addition of equal volume of glycerol and 0.04% Triton X-100, the proteins were stored aliquoted at −80° C.

Aurora Kinase A Luminescent Kinase Assay:

The inhibitory activity of the compounds of this invention against Aurora kinase was assessed using GST-tAurora A (123-401aa) fusion protein obtained above, according to a modified method described in Koresawa, M.; Okabe, T. *Assay Drug Dev Technol* 2004, 2, 153. Briefly, a test compound, enzyme, substrate-tetra(LRRWSLG), DTT and ATP were dissolved in Aur buffer (50 mM Tris-HCl pH 7.4, 10 mM NaCl, 10 mM $MgCl_2$, and 100 µg/ml BSA) individually before the assay. Test compounds were consecutively diluted from 10 mM stock (for single dose: compounds were diluted from 10 mM stock to 100 µM and 20 µM; for $IC_{50}$: 5× serial dilution was made from 100 µM to 0.16 µM) in Aur buffer. Diluted compounds (25 µl) were pre-incubated with purified 105 ng (10 µl) of GST-tAurora A (123-401aa) fusion protein at 25° C. for 15 min into 96 well U-bottomed plates (268152, NUNC). 5 µM ATP (5 µl), 1 mM DTT (5 µl) and 0.1 mM tetra(LRRWSLG) peptide substrate (5 µl) were added into the reactions of test compounds and GST-tAurora A. The reactions were incubated at 37° C. for 90 min. 50 µl of Kinase-Glo Plus Reagent (V3771, Promega) was added into the reactions, followed by the incubation at 25° C. for 20 min. 70 µl of reaction solutions were transferred to 96 well black plates (237108, NUNC) to quantify the ATP remaining in the solutions, which inversely relates to kinase activity. The luminescence was recorded by $vector^2$ (V-1420 multilabel HTS counter, Perkin Elmer).

Compounds 1-7, 20, 22, 47, 56, 72, 81, 140, 190, and 201-254 were tested in this assay. Unexpectedly, Compounds 1-7, 20, 22, 47, 56, 72, 81, 140, 190, 201-212, 214, 218-220, 222-228, 230-237, 240-242, and 244-254 showed $IC_{50}$ values (i.e., the concentration of a test compound at which activity of 50% of Aurora A is inhibited) lower than 1 µM. Among them, Compounds 2-7, 56, 72, 81, 140, 190, 202, 203, 205-208, 212, 222, 223, 225-227, 231, 233, 234, 236, 240-242, 246, 248, 250, 253, and 254 showed $IC_{50}$ values between 51 nM and 450 nM; and Compounds 1, 20, 22, 47, 201, 204, 209-211, 218-220, 224, 228, 232, 235, 237, 244, 245, 247, 249, 251, and 252 showed $IC_{50}$ values between 1 nM and 50 nM.

Example 71

In Vitro Anticancer Activity

HCT-116 cell viability was examined by the MTS assay (Promega, Madison, Wis., USA). 2000 HCT-116 cells in 100 µL McCoy's 5a medium were seeded in each well of a 96-well plate. After 96-h incubation with a test compound, the cells were incubated with 20 µL of a MTS/PMS mixture (MTS/PMS ratio: 20:1) for 2 h at 37° C. in a humidified incubator with 5% $CO_2$ to allow viable cells to convert the tetrazolium salt (MTS) into formazan. The amount/concentration of formazan, which indicates the number of live cells, was determined by measuring the absorbance at 490 nm using a PerkinElmer Victor2 plate reader (PerkinElmer, Shelton, Conn., USA).

Compounds 1-7, 20, 22, 47, 56, 72, 81, 140, 190, and 201-254 were tested in this assay. Unexpectedly, 2, 7, 22, 47, 56, 204-207, 212, 213, 217-220, 222-225, 229, 231, 232, 236, 237, 245-247, 250, and 252 showed $IC_{50}$ values between 101 nM and 850 nM; and Compounds 1, 3-5, 20, 201-203, 208-211, 228, 233-235, 240, 244, 248, 249, 251, 253, and 254 showed $IC_{50}$ values lower than 100 nM.

Example 72

Co-Crystallization of a Fused Multicyclic Compound and Aurora Kinase

Expression and Purification of Aurora A:

Aurora A catalytic domain (residues 123-401) with one mutation at residue 288 (T288D) and six His as the tag at the N-terminus was cloned into the pET-28a vector and expressed in BL21 DE3 *E. coli*. The protein was then purified by nickel column following the procedures as suggested by the suppliers (Amersham Biosciences, Piscataway, N.J.). The bound protein was washed with 10% of buffer solution (40 mmol HEPES (pH 7.5), 50 mmol NaCl and 500 mmol imidazole) and eluted with 100% of buffer solution. The fractions containing Aurora A catalytic domain was then treated with TEV protease (Invitrogen) overnight at 4° C. to remove the His tag and concentrated to 8 mg/mL in a buffer containing 40 mmol HEPES pH 7.5, 50 mmol NaCl, 1 mmol DTT.

Crystallization and Structure Determination:

The hanging drop method was used to obtain the crystals of Aurora A in complex with test compounds. A drop of 1.5 µl protein pre-incubated with a test compound for half hour on ice was mixed with the equal volume of reservoir solution (22% PEG400 and 0.1 mmol ammonia sulfate). The crystals were grown at 18° C. for 3-7 days. Before being flash-frozen in liquid nitrogen, the crystal was immersed briefly in a cryo-protectant containing 37% PEG400. Diffraction data were collected on beamline SP12B2 at the SPring-8 (Japan) and beamlines, BL13B1 and BL13C1, at the NSRRC (Taiwan). The data were processed by DENZO (see Otwinowski, Z.; Minor, W. Processing of x-ray diffraction data collected in oscillation mode. *Methods in Enzymology* 1997, 276, 307-326) and reduced with SCALEPACK. The structure was solved by molecular replacement in MOLREP (see Vagin A, T. A. MOLREP: an automated program for molecular replacement. *J. Appl. Cryst.* 1997, 30, 1022-1025) using the published Aurora A structure (PDB code: 1MQ4) as the search model. The refinement calculation were performed by REFMAC5 (see Murshudov G N, V. A., Dodson E J. Refinement of macromolecular structures by the maximum-likelihood method. *Acta Crystallogr* 1997, D, 240-255) and model building was carried out with the program 09.0 (see Jones T A, Z. J., Cowan S W, Kjeldgaard. Improved methods for building protein models in electron density maps and the location of errors in these models. *Acta Crystallogr* 1991, A, 110-119).

Compound 1 was co-crystallized with Aurora A. The complex structure was solved by x-ray crystallography.

Example 73

In Vivo Anticancer Activity

In vivo anticancer efficacy of the compounds of this invention was assessed using colon tumor xenograft mice (injected with HCT-116), as described in Cancer Research 2004, 64, 4621-4628.

(i) Anticancer Activity of Compound 3

HCT-116 cells were injected via s.c. in nude mice to form colon tumor xenograft mice. Mice bearing tumors with a size of ~100 $mm^3$ were randomly assigned to three groups: a vehicle control group (10 mice), a positive control group (10 mice), and a treatment group (21 mice). Of the treated mice, ten received Compound 3 at a daily dosage of 25 mg/kg via IV injection through the tail veins for 5 days/week for 2 consecutive weeks (days 1-5 and 8-12) and eleven received the same compound at a daily dosage of 50 mg/kg via IV injection through the tail veins for 5 consecutive days (days 1-5). The positive control mice received VX-680 (a known anti-cancer drug) at a daily dosage of 50 mg/kg, also via IV injection through the tail veins for 5 days/week for 2 consecutive weeks (days 1-5 and 8-12).

Unexpectedly, at the dosages of 25 and 50 mg/kg, Compound 3 suppressed tumor growth significantly and better than VX-680 at a dosage of 50 mg/kg, indicating its potent in vivo anti-cancer activity. Upon treatment with Compound 3, the tumor size was 35% (25 mg/kg) or 36% (50 mg/kg) of that in the vehicle control group at the end of the observation period on the $22^{nd}$ day post treatment. In comparison, the tumor size in the VX-680-treated group was 50% of that in the vehicle control animals.

(ii) Anticancer Activity of Compound 4

HCT-116 cells were injected via s.c. in nude mice to form colon tumor xenograft mice. Mice bearing tumors with a size of ~100 mm³ were randomly assigned to three groups: a vehicle control group (10 mice), a positive control group (10 mice), and a treatment group (21 mice). Of the treated mice, ten received Compound 4 at a daily dosage of 5 mg/kg and eleven received the same compound at a daily dosage of 15 mg/kg via IV injection through the tail veins for 5 days/week for 2 consecutive weeks (days 1-5 and 8-12). The positive control mice received VX-680 at a daily dosage of 50 mg/kg, also via IV injection through the tail veins for 5 days/week for 2 consecutive weeks (days 1-5 and 8-12).

Unexpectedly, at the dosage of 15 mg/kg, Compound 4 suppressed tumor growth significantly and better than VX-680 at a dosage of 50 mg/kg, indicating its potent in vivo anti-cancer activity. Upon treatment with Compound 4, the tumor size was 67% (5 mg/kg) or 37% (15 mg/kg) of that in the vehicle control group at the end of the observation period on the $22^{nd}$ day post treatment. In comparison, the tumor size in the VX-680-treated group was 50% of that in the vehicle control animals.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

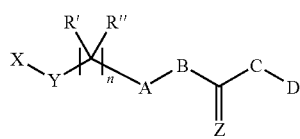

wherein
X is

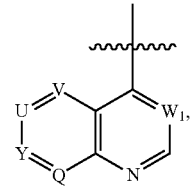

in which each of Q, T, U, and V is, independently, $CR_3$, $R_3$ being H, alkyl, alkenyl, alkynyl, aryl, heteroaryl, cycloalkyl, cycloalkenyl, heterocycloalkyl, heterocycloalkenyl, halo, cyano, $OR_a$, $OC(O)R_a$, $C(O)R_a$, $C(O)OR_a$, $C(O)NR_aR_b$, $NR_aR_b$, $NHC(O)R_a$, $NHC(O)NR_aR_b$, $NHC(S)R_a$, $NHC(O)OR_a$, $SO_3R_a$, or $SO_2NR_aR_b$, in which each of $R_a$ and $R_b$, independently, is H, alkyl, alkenyl, alkynyl, aryl, heteroaryl, cycloalkyl, cycloalkenyl, heterocycloalkyl, or heterocycloalkenyl; $W_1$ is N;

each of Y and Z, independently, is O, S, or $NR_c$, in which $R_c$ is a bond, H, alkyl, alkenyl, alkynyl, aryl, heteroaryl, cycloalkyl, cycloalkenyl, heterocycloalkyl, heterocycloalkenyl, cyano, or $NO_2$;

each of R' and R", independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl;

A is arylene or heteroarylene;

B is O, S, or $NR_d$, in which $R_d$ is H, alkyl, alkenyl, or alkynyl;

C is O, S, or $NR_e$, in which $R_e$ is H, alkyl, alkenyl, or alkynyl; or B and C, together with the carbon atom to which they are bonded, are heterocycloalkyl or heterocycloalkenyl;

D is alkyl, alkenyl, alkynyl, aryl, monocyclic heteroaryl, cycloalkyl, cycloalkenyl, heterocycloalkyl, or heterocycloalkenyl; or C and D together are heterocycloalkyl, heterocycloalkenyl, aryl, or heteroaryl; or C, D, and Z together with the carbon atom to which they are bonded are bicyclic or tricyclic heteroaryl; and n is 2, 3, or 4.

2. The compound of claim 1, wherein Z is O and each of B and C is NH.

3. The compound of claim 2, wherein each of the $R_3$ groups, independently, is H, alkyl, alkynyl, halo, cyano, $OR_a$, or $NR_aR_b$.

4. The compound of claim 3, wherein each of the $R_3$ groups, independently, is H, $OR_a$, or $NR_aR_b$, in which each of $R_a$ and $R_b$, independently, is H, alkyl, alkenyl, alkynyl, cycloalkyl, aryl, or heteroaryl.

5. The compound of claim 4, wherein Y is NH and n is 2.

6. The compound of claim 5, wherein A is phenyl or thiazolyl; D is alkyl, aryl, monocyclic heteroaryl, or cycloalkyl; and each of R' and R" is H.

7. The compound of claim 2, wherein Y is NH and n is 2.

8. The compound of claim 7, wherein A is phenyl or thiazolyl; D is alkyl, aryl, monocyclic heteroaryl, or cycloalkyl; and each of R' and R" is H.

9. A pharmaceutical composition, comprising a compound of claim 1 and a pharmaceutically acceptable carrier.

10. The compound of claim 7, wherein each of the $R_3$ groups, independently, is H, alkyl, alkynyl, halo, cyano, $OR_a$, or $NR_aR_b$.

11. The compound of claim 1, wherein each of the $R_3$ groups, independently, is H, alkyl, alkynyl, halo, cyano, $OR_a$, or $NR_aR_b$.

12. The compound of claim 1, wherein n is 2; and D is 6 membered heteroaryl having one or more N, or C, D, and Z together with the carbon atom to which they are bonded are bicyclic heteroaryl.

13. The compound of claim 1, wherein n is 2; and D is 5 membered heteroaryl having one or more N, S, or O, or C, D, and Z together with the carbon atom to which they are bonded are bicyclic heteroaryl.

14. The compound of claim 1, wherein n is 2; and D is phenyl, pyridyl, or cyclopropyl, or C, D, and Z together with the carbon atom to which they are bonded are benzimidazolyl.

15. The compound of claim 6, wherein n is 2; and D is 6 membered heteroaryl having one or more N, or C, D, and Z together with the carbon atom to which they are bonded are bicyclic heteroaryl.

16. The compound of claim 6, wherein n is 2; and D is 5 membered heteroaryl having one or more N, S, or O, or C, D, and Z together with the carbon atom to which they are bonded are bicyclic heteroaryl.

17. The compound of claim 6, wherein n is 2; and D is phenyl, pyridyl, or cyclopropyl, or C, D, and Z together with the carbon atom to which they are bonded are benzimidazolyl.

18. The compound of claim 8, wherein n is 2; and D is 6 membered heteroaryl having one or more N, or C, D, and Z together with the carbon atom to which they are bonded are bicyclic heteroaryl.

19. The compound of claim 8, wherein n is 2; and D is 5 membered heteroaryl having one or more N, S, or O, or C, D, and Z together with the carbon atom to which they are bonded are bicyclic heteroaryl.

20. The compound of claim 8, wherein n is 2; and D is phenyl, pyridyl, or cyclopropyl, or C, D, and Z together with the carbon atom to which they are bonded are benzimidazolyl.

21. A compound, wherein the compound is:

Compound 1

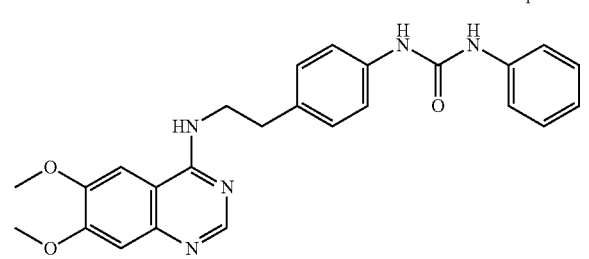

-continued

Compound 3

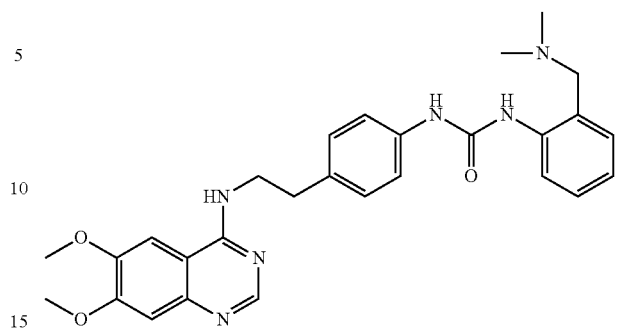

Compound 4

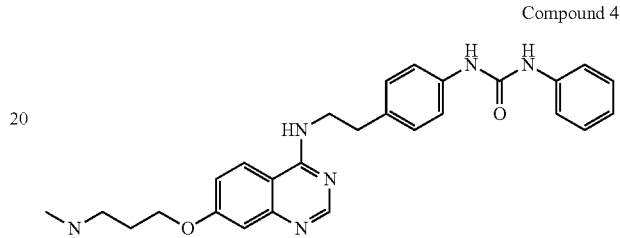

Compound 20

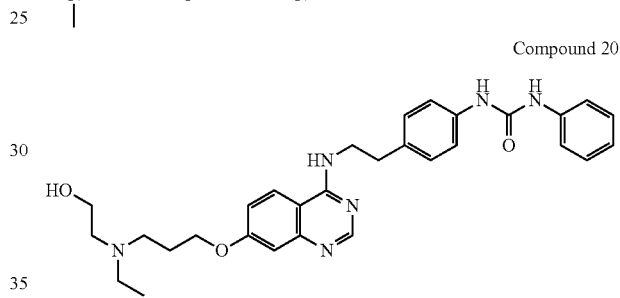

Compound 22

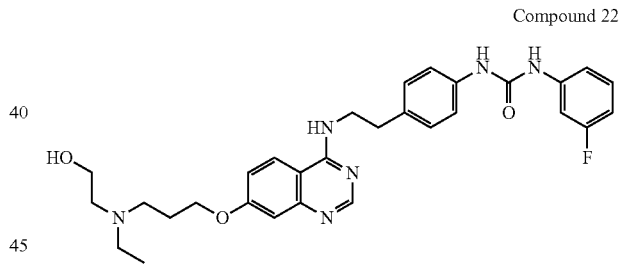

Compound 207

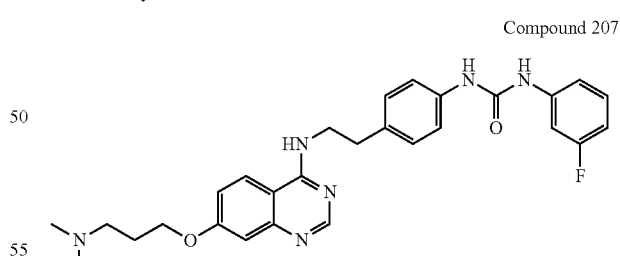

Compound 224

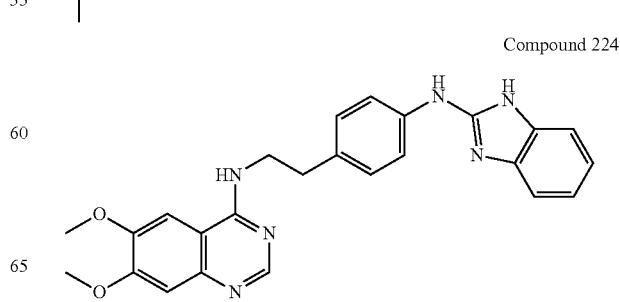

-continued
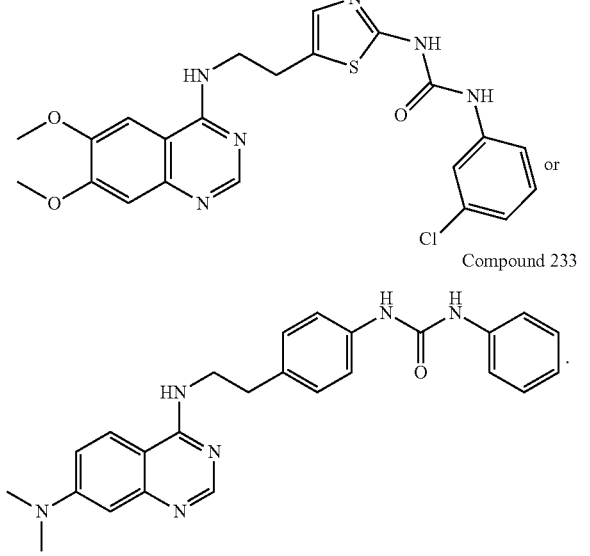
Compound 228
Compound 233
22. The compound of claim 6, wherein each of the $R_3$ groups, independently, is H or $OR_a$, in which $R_a$ is alkyl; A is thiazolyl; and D is phenyl.
23. The compound of claim 22, wherein the compound is
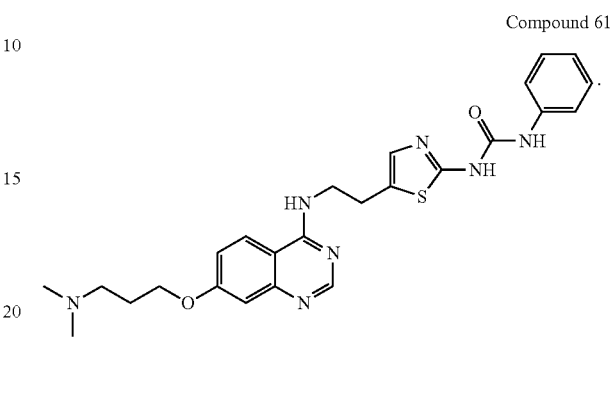
Compound 61
\* \* \* \* \*